(12) United States Patent
Luo et al.

(10) Patent No.: US 6,586,000 B2
(45) Date of Patent: *Jul. 1, 2003

(54) HYDROXIDE-RELEASING AGENTS AS SKIN PERMEATION ENHANCERS

(75) Inventors: Eric C. Luo, Plano, TX (US); Eric C. Jacobson, San Diego, CA (US); Tsung-Min Hsu, San Diego, CA (US)

(73) Assignee: Dermatrends, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/738,410

(22) Filed: Dec. 14, 2000

(65) Prior Publication Data

US 2001/0051166 A1 Dec. 13, 2001

Related U.S. Application Data

(63) Continuation-in-part of application No. 09/569,889, filed on May 11, 2000, which is a continuation-in-part of application No. 09/465,098, filed on Dec. 16, 1999, now abandoned.

(51) Int. Cl.[7] .......................... A61F 13/00; A61L 15/00
(52) U.S. Cl. .................. 424/449; 424/443; 424/445; 424/447; 424/448; 514/946; 514/947; 514/944
(58) Field of Search ................. 424/449, 443, 424/445; 514/946, 947

(56) References Cited

U.S. PATENT DOCUMENTS

| 4,704,282 A | 11/1987 | Campbell et al. |
|---|---|---|
| 4,789,547 A | 12/1988 | Song et al. |
| 4,837,027 A | 6/1989 | Lee et al. |
| 5,071,657 A | 12/1991 | Oloff et al. |
| 5,152,997 A | 10/1992 | Ebert et al. |
| 5,318,960 A | 6/1994 | Toppo |
| 5,432,192 A | 7/1995 | Sawanishi et al. |
| 5,446,070 A | 8/1995 | Mantelle |

(List continued on next page.)

FOREIGN PATENT DOCUMENTS

| EP | 0 276 561 A1 | * 8/1988 |
|---|---|---|
| EP | 0276561 | 8/1988 |
| EP | 0316065 | 5/1989 |
| EP | 0709088 | 5/1996 |
| EP | 0842662 | 5/1998 |
| FR | 2692145 | * 5/1992 |
| FR | 2692145 | 12/1993 |
| JP | 2180835 | * 7/1990 |
| JP | 6092843 | 4/1994 |
| JP | WO 99/49844 | 10/1999 |
| KR | 9507098 | 6/1995 |
| WO | WO 94/21271 | 9/1994 |

OTHER PUBLICATIONS

U.S. patent application Ser. No. 09/465,098, Luo et al., filed Dec. 16, 1999.
U.S. patent application Ser. No. 09/569,889, Luo et al., filed May 11, 2000.
Aungst et al. (1990), "Contributions of Drug Solubilization, Partitioning, Barrier Disruption, and Solvent Permeation to the Enhancement of Skin Permeation of Various Compounds with Fatty Acids and Amines," *Pharmaceutical Research* 7(7):712–718.

Primary Examiner—Thurman K. Page
Assistant Examiner—Isis Ghali
(74) Attorney, Agent, or Firm—Dianne E. Reed; Shelley P. Eberle; Reed & Eberle LLP

(57) ABSTRACT

A method is provided for increasing the permeability of skin or mucosal tissue to topically or transdermally administered pharmacologically or cosmeceutically active agents. The method involves use of a specified amount of a hydroxide-releasing agent, the amount optimized to increase the flux of the active agent through a body surface while minimizing the likelihood of skin damage, irritation or sensitization. Topically applied formulations and drug delivery devices employing hydroxide-releasing agents as permeation enhancers are provided as well.

41 Claims, 14 Drawing Sheets

U.S. PATENT DOCUMENTS

| | | | |
|---|---|---|---|
| 5,460,820 A | 10/1995 | Ebert et al. | |
| 5,462,744 A | 10/1995 | Gupte et al. | |
| 5,462,746 A | 10/1995 | Wolter et al. | |
| 5,474,783 A | 12/1995 | Miranda et al. | |
| 5,498,417 A | 3/1996 | Lhila et al. | |
| 5,500,222 A | 3/1996 | Lee et al. | |
| 5,527,832 A | 6/1996 | Chi et al. | |
| 5,532,278 A | 6/1996 | Chi et al. | |
| 5,534,496 A | 7/1996 | Lee et al. | |
| 5,562,917 A | 10/1996 | Durif et al. | |
| 5,573,778 A | 11/1996 | Therriault et al. | |
| 5,599,554 A | 2/1997 | Majeti | |
| 5,614,211 A | 3/1997 | Gale et al. | |
| 5,674,895 A | 10/1997 | Guittard et al. | |
| 5,807,568 A | 9/1998 | Cody et al. | |
| 5,817,332 A | 10/1998 | Urtti et al. | |
| 5,830,497 A * | 11/1998 | Yamanaka et al. | 424/448 |
| 5,834,513 A | 11/1998 | Ptchelintsev et al. | |
| 5,847,003 A | 12/1998 | Ptchelintsev et al. | |
| 5,879,690 A | 3/1999 | Perricone | |
| 5,939,094 A | 8/1999 | Durif et al. | |
| 5,952,000 A * | 9/1999 | Venkateshwaran et al. | 424/448 |
| 5,962,018 A | 10/1999 | Curtis et al. | |
| 5,976,566 A * | 11/1999 | Samour et al. | 424/449 |
| 5,985,317 A | 11/1999 | Venkateshwaran et al. | |
| 5,985,860 A | 11/1999 | Toppo | |
| 5,989,586 A | 11/1999 | Hsu et al. | |
| 5,990,113 A | 11/1999 | Yamazaki et al. | |
| 5,990,179 A * | 11/1999 | Gyory et al. | 514/329 |
| 5,993,851 A | 11/1999 | Foldvari | |
| 6,004,577 A | 12/1999 | Murdock | |
| 6,019,988 A * | 2/2000 | Parab et al. | 424/400 |
| 6,019,997 A | 2/2000 | Scholz et al. | |
| 6,123,961 A | 9/2000 | Aberg | |
| 6,132,760 A | 10/2000 | Hedenstrom et al. | |
| 6,139,866 A | 10/2000 | Chono et al. | |
| 6,174,546 B1 | 1/2001 | Therriault et al. | |
| 6,204,268 B1 | 3/2001 | Scarborough et al. | |
| 6,214,374 B1 | 4/2001 | Schmirler et al. | |

* cited by examiner

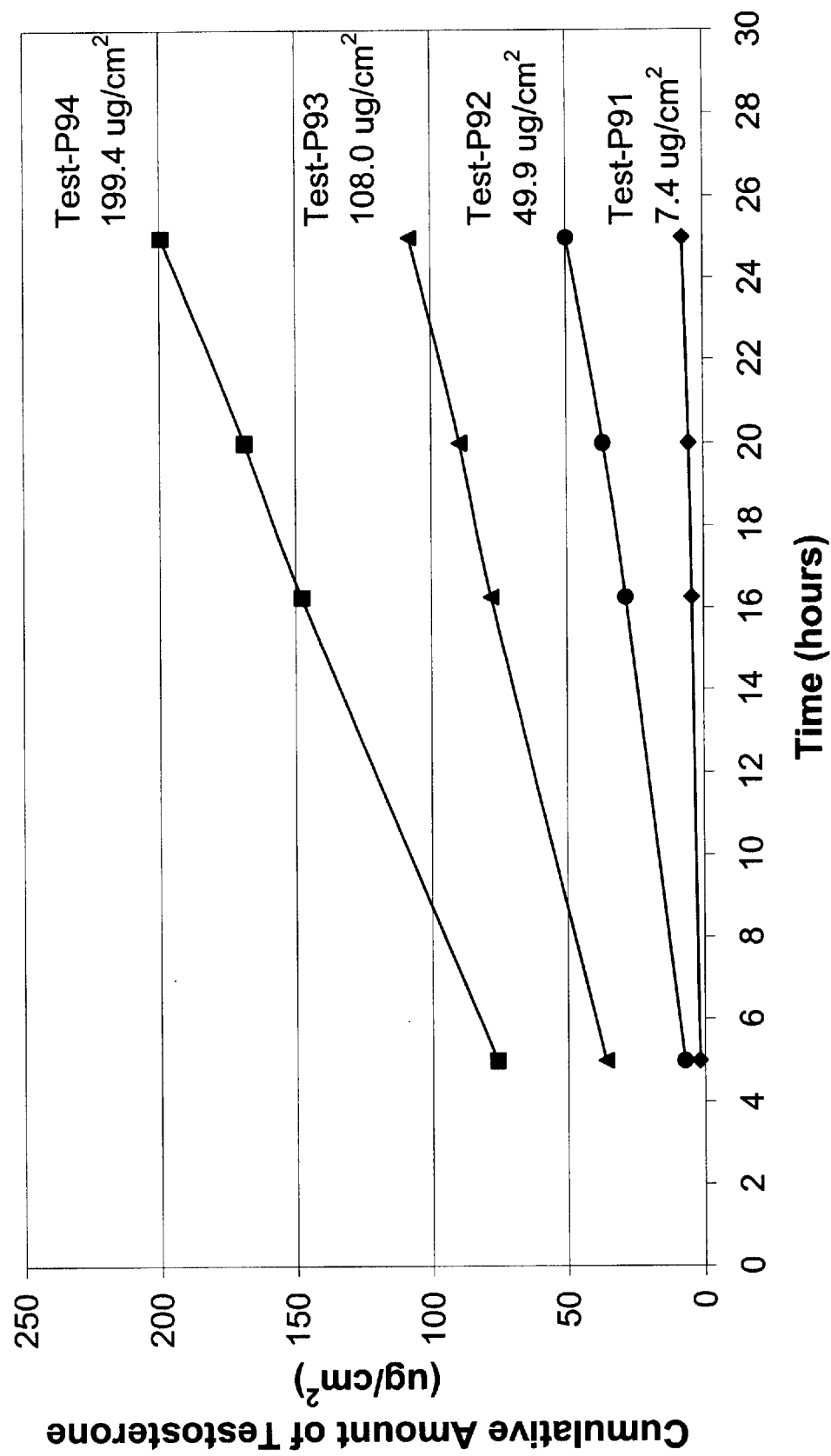

HYDROXIDE-RELEASING AGENTS AS SKIN PERMEATION ENHANCERS

CROSS-REFERENCE TO RELATED APPLICATIONS

This is a continuation-in-part of U.S. Ser. No. 09/569,889, filed May 11, 2000, which was a continuation-in-part of U.S. Ser. No. 09/465,098, filed Dec. 16, 1999, now abandoned the disclosures of which are incorporated by reference.

TECHNICAL FIELD

This invention relates generally to the topical and transdermal administration of pharmacologically active agents, and more particularly relates to methods and compositions for enhancing the permeability of skin or mucosal tissue to topically applied pharmacologically active agents.

BACKGROUND ART

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration. With many drugs, the rate of permeation through the skin is extremely low without the use of some means to enhance the permeability of the skin.

In order to increase the rate at which a drug penetrates through the skin, then, various approaches have been followed, each of which involves the use of either a chemical penetration enhancer or a physical penetration enhancer. Physical enhancement of skin permeation include, for example, electrophoretic techniques such as iontophoresis. The use of ultrasound (or "phonophoresis) as a physical penetration enhancer has also been researched. Chemical enhancers are compounds that are administered along with the drug (or in some cases the skin may be pretreated with a chemical enhancer) in order to increase the permeability of the stratum corneum, and thereby provide for enhanced penetration of the drug through the skin. Ideally, such chemical penetration enhancers (or "permeation enhancers," as the compounds are referred to herein) are compounds that innocuous and serve merely to facilitate diffusion of the drug through the stratum corneum.

Various compounds for enhancing the permeability of skin are known in the art and described in the pertinent texts and literature. Compounds that have been used to enhance skin permeability include: sulfoxides such as dimethylsulfoxide (DMSO) and decylmethylsulfoxide ($C_{10}$MSO); ethers such as diethylene glycol monoethyl ether (available commercially as Transcutol® ) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly salicylic acid and salicylates, citric acid and succinic acid. *Percutaneous Penetration Enhancers,* eds. Smith et al. (CRC Press, 1995) provides an excellent overview of the field and further background information on a number of chemical and physical enhancers.

Although many chemical permeation enhancers are known, there is an ongoing need for enhancers that are highly effective in increasing the rate at which a drug permeates the skin, do not result in skin damage, irritation, sensitization, or the like, and can be used to effect transdermal delivery of even high molecular weight drugs such as peptides, proteins, and nucleic acids. It has now been discovered that hydroxide-releasing agents are highly effective permeation enhancers, even when used without co-enhancers, provide all of the aforementioned advantages relative to known permeation enhancers. Furthermore, in contrast to conventional enhancers, transdermal administration of drugs with hydroxide-releasing agents as permeation enhancers, employed at the appropriate levels, does not result in systemic toxicity.

SUMMARY OF THE INVENTION

It is thus a primary object of the invention to address the above-described need in the art by providing a novel method for enhancing the rate at which an active agent administered to a patient's body surface permeates into and/or through the body surface.

It is another object of the invention to provide such a method wherein a hydroxide-releasing agent is employed as a permeation enhancer to increase the flux of an active agent through a patient's skin or mucosal tissue.

It is still another object of the invention to provide such a method wherein the amount of hydroxide-releasing agent employed is optimized to enhance permeation while minimizing or eliminating the possibility of skin damage, irritation or sensitization.

It is yet another object of the invention to provide such a method wherein the active agent is a pharmacologically active agent selected from free acids, free bases, basic addition salts of free acids, acid addition salts of free bases, nonionizable drugs, peptides and proteins.

It is a further object of the invention to provide such a method wherein the active agent is a cosmeceutically effective agent.

It is still a further object of the invention to provide such a method wherein the active agent is intended for local delivery, and drug administration is topical.

It is yet a further object of the invention to provide such a method wherein the active agent is intended for systemic delivery, and drug administration is transdermal.

It is an additional object of the invention to provide formulations and drug delivery systems for carrying out the aforementioned methods.

Additional objects, advantages and novel features of the invention will be set forth in part in the description that follows, and in part will become apparent to those skilled in the art upon examination of the following, or may be learned by practice of the invention.

In one aspect of the invention, then, a method is provided for increasing the rate at which an active agent permeates through the body surface of a patient. The method involves administering the agent to a predetermined area of the patient's body surface in combination with a hydroxide-releasing agent in a predetermined amount effective to enhance the flux of the agent through the body surface without causing damage thereto. The predetermined amount of the hydroxide-releasing enhancer is preferably an amount effective to provide a pH at the body surface, i.e., during drug administration, in the range of about 8.0 to 13, preferably about 8.0 to 11.5, most preferably about 8.5 to 11.5. If a skin patch is used, this is the preferred pH at the interface between the basal surface of the patch (i.e., the skin-contacting or mucosa-contacting surface of the patch) and the body surface. The optimal amount (or concentration) of any one hydroxide-releasing agent will, however, depend on the specific hydroxide-releasing agent, i.e., on the strength or weakness of the base, its molecular weight, and other factors as will be appreciated by those of ordinary skill in the art of transdermal drug delivery. This optimal amount may be determined using routine experimentation to ensure that the pH at the body surface is within the aforementioned ranges, i.e., in the range of about 8.0 to 13, preferably about 8.0 to 11.5, most preferably about 8.5 to 11.5. A conventional transdermal drug delivery device or "patch" may be used to administer the active agent, in which case the drug and hydroxide-releasing agent are generally present in a drug reservoir or reservoirs. However, the drug and hydroxide-releasing agent may also be administered to the body surface using a liquid or semisolid formulation. Alternatively, or in addition, the body surface may be pretreated with the enhancer, e.g., treated with a dilute solution of the hydroxide-releasing agent prior to transdermal drug administration. Such a solution will generally be comprised of a protic solvent (e.g., water or alcohol) and have a pH in the range of about 8.0 to 13, preferably 8.0 to 11.5, more preferably 8.5 to 11.5.

In a related aspect of the invention, a composition of matter is provided for delivering a drug through a body surface using a hydroxide-releasing agent as a permeation enhancer. Generally, the formulation comprises (a) a therapeutically effective amount of a drug, (b) a hydroxide-releasing agent in an amount effective to enhance the flux of the drug through the body surface without causing damage thereto, and (c) a pharmaceutically acceptable carrier suitable for topical or transdermal drug administration. The composition may be in any form suitable for application to the body surface, and may comprise, for example, a cream, lotion, solution, gel, ointment, paste or the like, and/or may be prepared so as to contain liposomes, micelles, and/or microspheres. The composition may be directly applied to the body surface or may involve use of a drug delivery device. In either case, it is preferred although not essential that water be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration.

In another aspect of the invention, a drug delivery system is provided for the topical or transdermal administration of a drug using a hydroxide-releasing agent as a permeation enhancer. The system will generally comprise: at least one drug reservoir containing the drug and the hydroxide-releasing agent in an amount effective to enhance the flux of the drug through the body surface without causing damage thereto; a means for maintaining the system in drug and enhancer transmitting relationship to the body surface; and a backing layer that serves as the outer surface of the device during use. The backing layer may be occlusive or nonocclusive, although it is preferably occlusive. The drug reservoir may be comprised of a polymeric adhesive, which may serve as the basal surface of the system during use and thus function as the means for maintaining the system in drug and enhancer transmitting relationship to the body surface. The drug reservoir may also be comprised of a hydrogel, or it may be a sealed pouch within a "patch"-type structure wherein the drug and hydroxide-releasing agent are present in the pouch as a liquid or semi-solid formulation.

BRIEF DESCRIPTION OF THE FIGURES

FIG. 14 is a graph illustrating the cumulative amount of testosterone from a matrix patch as described in Example 18.

DETAILED DESCRIPTION OF THE INVENTION

I. Definitions and Overview

Figure 1:
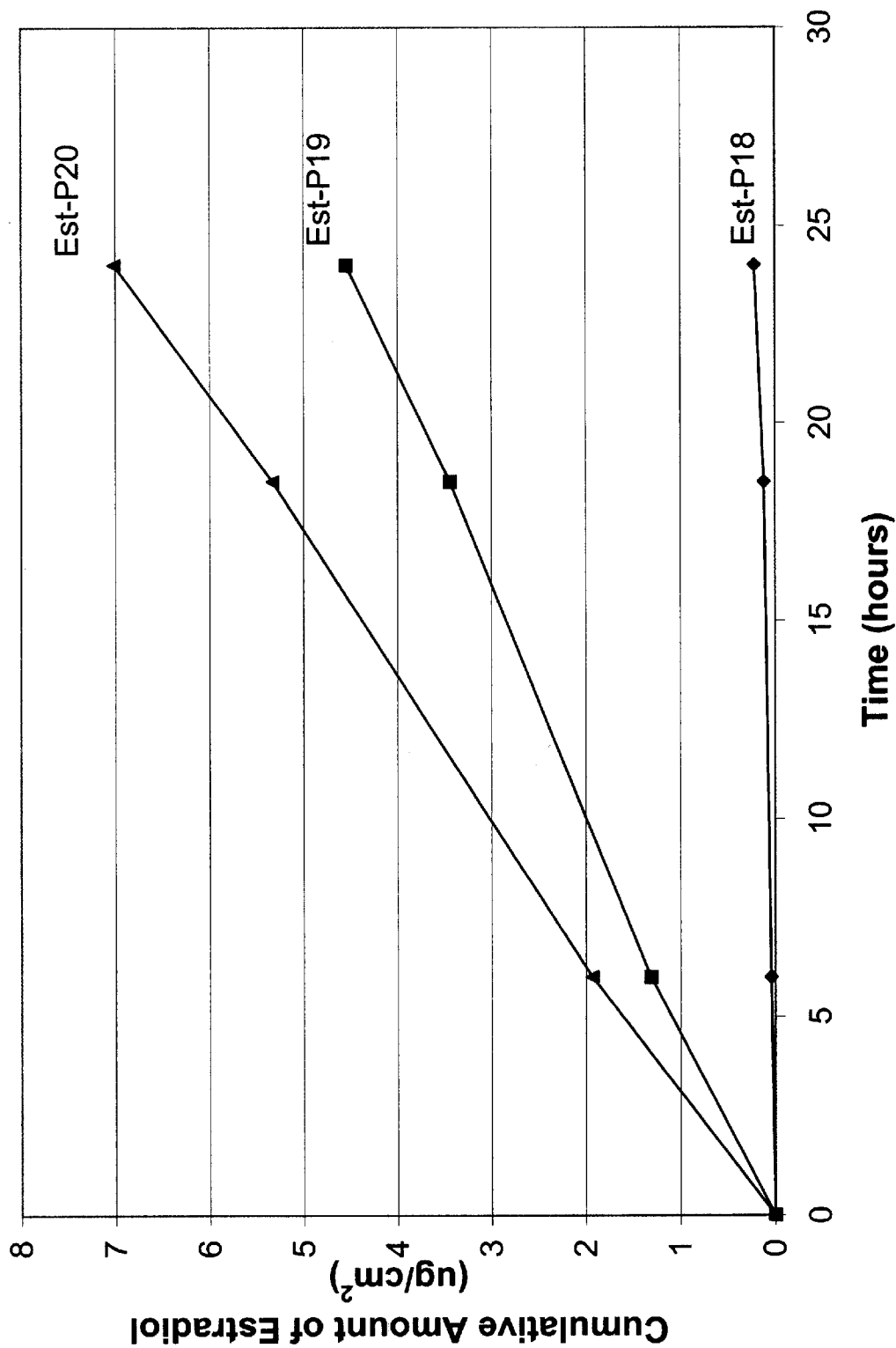
FIG. 1 is a graph illustrating the cumulative amount of estradiol from a matrix patch as described in Example 1.

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a pharmacologically active agent" includes a mixture of two or more such compounds, reference to "a hydroxide-releasing agent" includes mixtures of two or more hydroxide-releasing agents, and the like.

In describing and claiming the present invention, the following terminology will be used in accordance with the definitions set out below.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "hydroxide-releasing agent" as used herein is intended to mean an agent that releases free hydroxide ions in an aqueous environment. The agent may contain hydroxide ions and thus release the ions directly (e.g., an alkali metal hydroxide), or the agent may be on that is acted upon chemically in an aqueous environment to generate hydroxide ions (e.g., a metal carbonate).

The terms "active agent," "drug" and "pharmacologically active agent" are used interchangeably herein to refer to a chemical material or compound that induces a desired effect, and include agents that are therapeutically effective, prophylactically effective, or cosmeceutically effective. Also included are derivatives and analogs of those compounds or classes of compounds specifically mentioned which also induce the desired effect.

By "therapeutically effective" amount is meant a nontoxic but sufficient amount of an active agent to provide the desired therapeutic effect.

By "transdermal" drug delivery is meant administration of a drug to the skin surface of an individual so that the drug passes through the skin tissue and into the individual's blood stream, thereby providing a systemic effect. The term "transdermal" is intended to include "transmucosal" drug administration, i.e., administration of a drug to the mucosal (e.g., sublingual, buccal, vaginal, rectal) surface of an individual so that the drug passes through the mucosal tissue and into the individual's blood stream.

The term "topical administration" is used in its conventional sense to mean delivery of a topical drug or pharmacologically active agent to the skin or mucosa, as in, for example, the treatment of various skin disorders. Topical administration, in contrast to transdermal administration, provides a local rather than a systemic effect. Unless otherwise stated or implied, the terms "topical drug administration" and "transdermal drug administration" are used interchangeably.

The term "body surface" is used to refer to skin or mucosal tissue.

By "predetermined area" of skin or mucosal tissue, which refers to the area of skin or mucosal tissue through which a drug-enhancer formulation is delivered, is intended a defined area of intact unbroken living skin or mucosal tissue. That area will usually be in the range of about 5 cm$^2$ to about 200 cm$^2$, more usually in the range of about 5 cm$^2$ to about 100 cm$^2$, preferably in the range of about 20 cm$^2$ to about 60 cm$^2$. However, it will be appreciated by those skilled in the art of drug delivery that the area of skin or mucosal tissue through which drug is administered may vary significantly, depending on patch configuration, dose, and the like.

"Penetration enhancement" or "permeation enhancement" as used herein relates to an increase in the permeability of the skin or mucosal tissue to the selected pharmacologically active agent, i.e., so that the rate at which the agent permeates therethrough (i.e., the "flux" of the agent through the body surface) is increased relative to the rate that would be obtained in the absence of permeation enhancement. The enhanced permeation effected through the use of such enhancers can be observed by measuring the rate of diffusion of drug through animal or human skin using, for example a Franz diffusion apparatus as known in the art and as employed in the Examples herein.

An "effective" amount of a permeation enhancer is meant a nontoxic, nondamaging but sufficient amount of the enhancer to provide the desired increase in skin permeability and, correspondingly, the desired depth of penetration, rate of administration, and amount of drug delivered.

"Carriers" or "vehicles" as used herein refer to carrier materials suitable for transdermal drug administration. Carriers and vehicles useful herein include any such materials known in the art which are nontoxic and does not interact with other components of the composition in a deleterious manner.

The term "aqueous" refers to a formulation or drug delivery system that contains water or that becomes water-containing following application to the skin or mucosal tissue.

A "peptidyl drug" as used herein is an active agent, drug or pharmacologically active agent that comprises a peptide, polypeptide or protein. Pharmacologically active derivatives and fragments of peptidyl drugs are included as well. For ease of discussion, a "peptidyl drug" will also include a single amino acid and derivatives thereof.

A "peptide" refers to a polymer in which the monomers are amino acids linked together through amide bonds. "Peptides" are generally smaller than proteins, i.e., about two to about ten amino acids in length. The term "peptide" includes "dipeptides" comprised of two amino acids and "tripeptides" comprised of three consecutively linked amino acids, and so forth.

A "polypeptide" refers to a polymer of amino acids generally comprised of about ten to about fifty amino acids.

A "protein" as used herein refers to a polymer of amino acids conventionally comprised of over fifty amino acids. The proteins that may be used as peptidyl drugs in the present invention may be naturally occurring proteins, modified naturally occurring proteins, or chemically synthesized proteins that may or may not be identical to naturally occurring proteins.

Accordingly, the invention pertains to a method, composition and drug delivery system for increasing the rate at which an active agent permeates through the body surface of a patient, wherein the method involves administering the agent to a predetermined area of the patient's body surface in combination with a hydroxide-releasing agent in an amount effective to enhance the flux of the agent through the body surface without causing damage thereto.

II. The Hydroxide-Releasing Agent

The "hydroxide-releasing agent" is a chemical compound that releases free hydroxide ions in the presence of an aqueous fluid. The aqueous fluid may be natural moisture at the skin surface, or a patch or composition that is used may contain added water, and/or be used in connection with an occlusive backing. Similarly, any liquid or semisolid formulation that is used is preferably aqueous or used in conjunction with an overlayer of an occlusive material.

Any hydroxide-releasing agent may be used provided that the compound releases free hydroxide ions in the presence of an aqueous fluid. Examples of suitable hydroxide-releasing agents include, but are not limited to, inorganic hydroxides, inorganic oxides, and alkali metal or alkaline earth metal salts of weak acids. Inorganic hydroxides include, for example, ammonium hydroxide, alkali metal hydroxide and alkaline earth metal hydroxides, such as sodium hydroxide, calcium hydroxide, potassium hydroxide, magnesium hydroxide, and the like. Inorganic oxides include, for example, magnesium oxide, calcium oxide, and the like. Metal salts of weak acids include, for example, sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), ammonium phosphate (dibasic), and the like. Preferred hydroxide-releasing agents are metal hydroxides such as sodium hydroxide and potassium hydroxide.

It is important that the amount of hydroxide-releasing agent in any patch or formulation is optimized so as to increase the flux of the drug through the body surface while minimizing any possibility of skin damage. In general, this means that the pH at the body surface in contact with a formulation or drug delivery system of the invention (i.e., the interface between the body surface and the formulation or delivery system) should be in the range of approximately 8.0 to 13, preferably about 8.0 to 11.5, more preferably about 8.5 to 11.5. This will typically although not necessarily mean that the pH of the formulation or the drug composition contained within a delivery system will be in the range of approximately 8.0 to 13, preferably about 8.0 to 11.5, more preferably about 8.5 to 11.5.

For inorganic hydroxides, the amount of hydroxide-releasing agent will typically represent about 0.5 wt. % to 4.0 wt. %, preferably about 0.5 wt. % to 3.0 wt. %, more preferably about 0.75 wt. % to 2.0 wt. % and optimally about 1.0 wt. %, of a topically applied formulation or of a drug reservoir of a drug delivery system, or "patch." The aforementioned amount applies to formulations and patches in which the active agent is (1) an uncharged molecule, i.e., the phenylpropanolamine is in nonionized, free base form, and (2) there are no additional species in the formulation or patch that could react with or be neutralized by the inorganic hydroxide. For formulations and patches in which the phenylpropanolamine is in the form of an acid addition salt, and/or wherein there are additional species in the formulations or systems that can be neutralized by or react with the hydroxide-releasing agent (i.e., acidic inactive ingredients), the amount of inorganic hydroxide will be the total of (1) the amount necessary to neutralize the acid addition salt and/or other base-neutralizable species, plus (2) about 0.5 wt. % to 4.0 wt. %, preferably about 0.5 wt. % to 3.0 wt. %, more preferably about 0.75 wt. % to 2.0 wt. % and optimally about 1.0 wt. %, of the formulation or drug reservoir. That is, for an acid addition salt of phenylpropanolamine, the inorganic hydroxide should be present in an amount just sufficient to neutralize the salt, plus an additional amount (i.e., about 0.5 wt. % to 4.0 wt. %, preferably about 0.5 wt. % to 3.0 wt. %, more preferably about 0.75 wt. % to 2.0 wt. % and optimally about 1.0 wt. %) to enhance the flux of the drug through the skin or mucosal tissue. For patches, the aforementioned percentages are given relative to the total dry weight of the formulation components and the adhesive, gel or liquid reservoir.

For other hydroxide-releasing agents such as inorganic oxides and metal salts of weak acids, the amount of hydroxide-releasing agent in the formulation or drug delivery system may be substantially higher, as high as 20 wt. %, in some cases as high as 25 wt. % or higher, but will generally be in the range of approximately 2 wt. % to 20 wt. %.

Still greater amounts of hydroxide-releasing agent may be used by controlling the rate and/or quantity of release of the hydroxide-releasing agent preferably during the drug delivery period itself.

However, for all hydroxide-releasing agents herein, the optimum amount of any particular agent will depend on the strength or weakness of the base, the molecular weight of the base, and other factors such as the number of ionizable sites in the drug administered and any other acidic species in the formulation or patch. One skilled in the art may readily determine the optimum amount for any particular agent by ensuring that a formulation or drug delivery system III. The Active Agent The active agent administered may be any compound that is suitable for topical, transdermal or transmucosal delivery and induces a desired local or systemic effect. Such substances include the broad classes of compounds normally delivered through body surfaces and membranes, including skin. In general, this includes: analgesic agents; anesthetic agents; antiarthritic agents; respiratory drugs, including anti-asthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and anti-arrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; and vasodilators including general coronary, peripheral and cerebral.

The amount of active agent administered will depend on a number of factors and will vary from subject to subject and depend on the particular drug administered, the particular disorder or condition being treated, the severity of the symptoms, the subject's age, weight and general condition, and the judgment of the prescribing physician. Other factors, specific to transdermal drug delivery, include the solubility and permeability of the carrier and adhesive layer in a drug delivery device, if one is used, and the period of time for which such a device will be fixed to the skin or other body surface. The minimum amount of drug is determined by the requirement that sufficient quantities of drug must be present in a device or composition to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

Preferred classes of active agents are described in the following sections.

A. Pharmacologically Active Amines

The active agent may be a pharmacologically active nitrogen-containing base, for example, a primary amine, a secondary amine, or a tertiary amine, or it may be an aromatic or non-aromatic nitrogen-containing heterocycle, an azo compound, an imine, or a combination of any of the foregoing.

Examples of specific primary amines include, but are not limited to, amphetamine, norepinephrine, phenylpropanolamine (including any of the four isomers, individually or in combination, i.e., (+)-norephedrine, (−)-norephedrine, (+)-norpseudoephedrine, and (−)-norpseudoephedrine), and pyrithiamine.

Examples of secondary and tertiary amines include, but are not limited to, amiodarone, amitryptyline, azithromycin, benzphetamine, bromopheniramine, chlorambucil, chloroprocaine, chloroquine, chlorpheniramine, chlorothen, chlorpromazine, cinnarizine, clarthromycin, clomiphene, cyclobenzaprine, cyclopentolate, cyclophosphamide, dacarbazine, demeclocycline, dibucaine, dicyclomine, diethylproprion, diltiazem, dimenhydrinate, diphenhydramine, diphenylpyraline, disopyramide, doxepin, doxycycline, doxylamine, dypyridame, ephedrine, epinephrine, ethylene diamine tetraacetic acid (EDTA), erythromycin, flurazepam, gentian violet, hydroxychloroquine, imipramine, isoproterenol, isothipendyl, levomethadyl, lidocaine, loxarine, mechlorethamine, melphalan, methadone, methafurylene, methapheniline, methapyrilene, methdilazine, methotimeperazine, methotrexate, metoclopramide, minocycline, naftifine, nicardipine, nicotine, nizatidine, orphenadrine, oxybutynin, oxytetracycline, phenindamine, pheniramine, phenoxybenzamine, phentolamine, phenylephrine, phenyltoloxamine, procainamide, procaine, promazine, promethazine, proparacaine, propoxycaine, propoxyphene, pyrilamine, ranitidine, scopolamine, tamoxifen, terbinafine, tetracaine, tetracycline, thonzylamine, tranadol, triflupromazine, trimeprazine, trimethylbenzamide, trimipramine, trlpelennamine, troleandomycin, uracil mustard, verapamil and vonedrine.

Examples of non-aromatic heterocyclic amines include, but are not limited to, alprazolam, amoxapine, arecoline, astemizole, atropine, azithromycin, benzapril, benztropine, beperiden, bupracaine, buprenorphine, buspirone, butorphanol, caffeine, capriomycin, ceftriaxone, chlorazepate, chlorcyclizine, chlordiazepoxide, chlorpromazine, chlorthiazide, ciprofloxacin, cladarabine, clemastine, clemizole, clindamycin, clofazamine, clonazepam, clonidine, clozapine, cocaine, codeine, cyclizine, cyproheptadine, dacarbzine, dactinomycin, desipramine, diazoxide, dihydroergotamine, diphenidol, diphenoxylate, dipyridamole, doxapram, ergotamine, estazolam, famciclovir, fentanyl, flavoxate, fludarabine, fluphenazine, flurazepam, fluvastin, folic acid, ganciclovir, granisetron, guanethidine, halazepam, haloperidol, homatropine, hydrocodone, hydromorphone, hydroxyzine, hyoscyamine, imipramine, itraconazole, keterolac, ketoconazole, levocarbustine, levorphone, lincomycin, lomefloxacin, loperamide, lorazepam, losartan, loxapine, mazindol, meclizine, meperidine, mepivacaine, mesoridazine, methdilazine, methenamine, methimazole, methotrimeperazine, methysergide, metronidazole, midazolam, minoxidil, mitomycin c, molindone, morphine, nafzodone, nalbuphine, naldixic acid, nalmefene, naloxone, naltrexone, naphazoline, nedocromil, nicotine, norfloxacin, ofloxacin, ondansetron, oxazepam, oxycodone, oxymetazoline, oxymorphone, pemoline, pentazocine, pentostatin, pentoxyfylline, perphenazine, phentolamine, physostigmine, pilocarpine, pimozide, pramoxine, prazosin, prochlorperazine, promazine, promethazine, pyrrobutamine, quazepam, quinidine, quinine, rauwolfia alkaloids, riboflavin, rifabutin, risperidone, rocuronium, scopalamine, sufentanil, tacrine, temazepam, terazosin, terconazole, terfenadine, tetrahydrazoline, thiordazine, thiothixene, ticlodipine, timolol, tolazoline, tolazamide, tolmetin, trazodone, triazolam, triethylperazine, trifluopromazine, trihexylphenidyl, trimeprazine, trimipramine, tubocurarine, vecuronium, vidarabine, vinblastine, vincristine, vinorelbine and xylometazoline.

Examples of aromatic heterocyclic amines include, but are not limited to, acetazolamide, acyclovir, adenosine phosphate, allopurinal, alprazolam, amoxapine, amrinone, apraclonidine, azatadine, aztreonam, bisacodyl, bleomycin, brompheniramine, buspirone, butoconazole, carbinoxamine, cefamandole, cefazole, cefixime, cefmetazole, cefonicid, cefoperazone, cefotaxime, cefotetan, cefpodoxime, ceftriaxone, cephapirin, chloroquine, chlorpheniramine, cimetidine, cladarabine, clotrimazole, cloxacillin, didanosine, dipyridamole, doxazosin, doxylamine, econazole, enoxacin, estazolam, ethionamide, famciclovir, famotidine, fluconazole, fludarabine, folic acid, ganciclovir, hydroxychloroquine, iodoquinol, isoniazid, isothipendyl, itraconazole, ketoconazole, lamotrigine, lansoprazole, lorcetadine, losartan, mebendazole, mercaptopurine, methafurylene, methapyriline, methotrexate, metronidazole, miconazole, midazolam, minoxidil, nafzodone, naldixic acid, niacin, nicotine, nifedipine, nizatidine, omeperazole, oxaprozin, oxiconazole, papaverine, pentostatin, phenazopyridine, pheniramine, pilocarpine, piroxicam, prazosin, primaquine, pyrazinamide, pyrilamine, pyrimethamine, pyrithiamine, pyroxidine, quinidine, quinine, ribaverin, rifampin, sulfadiazine, sulfamethizole, sulfamethoxazole, sulfasalazine, sulfasoxazole, terazosin, thiabendazole, thiamine, thioguanine, thonzylamine, timolol, trazodone, triampterene, triazolam, trimethadione, trimethoprim, trimetrexate, triplenamine, tropicamide and vidarabine.

Examples of azo compounds are phenazopyridine and sulfasalazine, while examples of imines include cefixime, cimetidine, clofazimine, clonidine, dantrolene, famotidine, furazolidone, nitrofurantoin, nitrofurazone and oxiconazole.

Combinations of the aforementioned drugs and/or combinations of one or more of the aforementioned drugs with different type of active agent may also be delivered using the methodology of the present invention.

Examples of particularly preferred nitrogen-containing drugs that may be administered using the methods, compositions and systems of the invention are phenylpropanolamine and oxybutynin.

Phenylpropanolamine, or 2-amino-1-phenyl-1-propanol, is described, for example, by Kanfer et al., in *Analytical Profiles of Drug Substances,* vol. 12, K. Florey, Ed. (New York: Academic Press, 1983). Phenylpropanolamine is a sympathomimetic agent that has been used as an anorectic agent, a decongestant, an anxiolytic agent, and as a drug for decreasing fatigue and confusion. See, for example, U.S. Pat. Nos. 5,019,594 to Wurtman et al., U.S. Pat. No. 5,260,073 to Phipps, and U.S. Pat. No. 5,096,712 to Wurtman. Phenylpropanolamine has two chiral centers and thus exists as four different isomers, generally referred to as (+)-norephedrine, (−)-norephedrine, (+)-norpseudoephedrine, and (−)-norpseudoephedrine, respectively. Generally, (−)-norephedrine and (+)-norpseudoephedrine are recognized as the more active isomers for most physiological uses. Phenylpropanolamine may be transdermally herein as a racemate, i.e., as a mixture of any two or more of the four isomers of phenylpropanolamine, generally a racemic mixture of (−)-norephedrine and (+)-norephedrine, or any one of the four isomers may be administered individually. Phenylpropanolamine will usually be administered as an anorectic agent (i.e., for appetite suppression), or may be employed as a decongestant, as an anxiolytic agent, or to decrease fatigue and confusion. Most commonly, the drug is used as either an anorectic agent or a decongestant. Generally, a daily dosage of racemic phenylpropanolamine using the present formulations and delivery systems will be in the range of about 10 mg/day to about 250 mg/day, preferably about 25 mg/day to about 200 mg/day.

Oxybutynin is classified as an anticholinergic antispasmodic drug and is commonly used in treating individuals suffering from an overactive bladder, e.g., neurogenic bladder. See, for example, U.S. Pat. No. 5,674,895 to Guittard et al. Oxybutynin contains a chiral center, and may therefore be administered as either a racemate or a single isomer. There is some disagreement as to whether the activity of the racemate resides in the S enantiomer or the R enantiomer, it appears that the activity predominantly resides in the R enantiomer. See Noronha-Blob (1990) *J. Pharmacol. Exp. Ther.* 256(2):562–567 and Goldenberg (1999) *Clin Ther.* 21(4):634–642. U.K. Patent No. 940,540 describes the preparation of racemic oxybutynin. Synthesis of (S)-oxybutynin is also known. For example, the S enantiomer may be obtained by resolution of the intermediate mandelic acid followed by esterification. See Kachur et al. (1988) *J. Pharmacol. Exp. Ther.* 247(3):867–72. The R enantiomer may obtained by first preparing 4-diethylamino-2-butynyl chloride from dichlorobutyne followed by reacting the single R enantiomer of cyclohexylphenylglycolic acid with the prepared 4-diethylamino-2-butynyl chloride to yield the R enantiomer of 4-diethylamino-2-butynyl phenylcyclohexlglycolate, i.e., (R)-oxybutynin. See U.S. Pat. No. 6,123,961 to Aberg. Alternatively, the individual isomers may be isolated from a racemic mixture of oxybutynin using techniques known in the art such as chromatography-based methods that use a chiral substrate. Transdermal administration of oxybutynin is useful in a variety of contexts, as will be readily appreciated by those skilled in the art. For example, the transdermal administration of oxybutynin is useful in the treatment of urinary urgency, urinary frequency, urinary leakage, incontinence, and painful or difficult urination. Generally, although not necessarily, these disorders are caused by a neurogenic bladder. In addition, the present compositions and drug delivery systems are useful to administer oxybutynin to treat other conditions and disorders that are responsive to transdermal administration of oxybutynin. For example, oxybutynin may be administered transdermally to treat individuals suffering from detrusor hyperreflexia and detrusor instability. Generally, a daily dosage of racemic oxybutynin using the present formulations and delivery systems will be in the range of about 1 to 20 mg over a 24-hour period. The daily dose of an individual enantiomer of oxybutynin, i.e., (S)-oxybutynin or (R)-oxybutynin, using the present formulations and delivery systems is preferably lower than the corresponding racemate dose. Specifically, it is preferred that the enantiomer dose be in the range of about 0.5 to 15 mg over a 24-hour period.

As many amine drugs are commercially available only in the salt form, i.e., in the form of an acid addition salt, use of a hydroxide-releasing agent as a permeation enhancer eliminates the need to convert the drug to the free base form prior to patch manufacture. That is, the hydroxide-releasing agent may be incorporated during patch manufacture, along with the acid addition salt, thus neutralizing the drug during manufacture rather than after.

B. Nonsteroidal Antiinflammatory Agents (NSAIDS)

Suitable nonsteroidal antiinflammatory agents that may be used in the formulations of the present invention include, but are not limited to: propionic acid derivatives such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid; apazone; diclofenac; difenpiramide; diflunisal; etodolac; flufenamic acid; indomethacin; ketorolac; meclofenamate; mefenamic acid; nabumetone; phenylbutazone; piroxicam; salicylic acid; sulindac; tolmetin; and combinations of any of the foregoing. Preferred NSAIDs are ibuprofen, diclofenac sodium, ketoprofen, ketorolac and piroxicam.

The NSAID or NSAIDs may be co-administered with one or more additional active agents, e.g.: antihistaminic agents such as diphenhydramine and chlorpheniramine (particularly diphenhydramine hydrochloride and chlorpheniramine maleate); corticosteroids, including lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17, 21-dibutyrate, etc.), alclometasone, dexamethasone, flumethasone, prednisolone, and methylprednisolone, as well as higher potency corticosteroids such as clobetasol propionate, betamethasone benzoate, betamethasone diproprionate, diflorasone diacetate, fluocinonide, mometasone furoate, triamcinolone acetonide, and the like; local anesthetic agents such as phenol, benzocaine, lidocaine, prilocaine and dibucaine; topical analgesics such as glycol salicylate, methyl salicylate, 1-menthol, d,1-camphor and capsaicin; and antibiotics. Preferred additional agents are antibiotic agents, discussed in Section F, infra.

The aforementioned compounds may be administered transdermally using the method, composition and system of the invention to treat any patient with an NSAID-responsive condition or disorder. Typically, NSAIDs are employed as anti-inflammatory and/or analgesic agents, and accordingly may be used to treat individuals suffering from rheumatic or arthritic disorders, including, for example: rheumatoid arthritis (RA), degenerative joint disease (also known as DJD and "osteoarthritis"); juvenile rheumatoid arthritis (JRA); psoriatic arthritis; gouty arthritis; ankylosing spondylitis; and lupus erythematoses such as systemic lupus erythematosus and discoid lupus erythematosus.

Other potential uses of NSAIDs include, but are not limited to, treating fever (via the anti-pyretic property of NSAIDs) or myocardial infarction (MI), transient ischemic attacks, and acute superficial thrombophlebitis (via inhibition of platelet aggregation). Further non-limiting uses for NSAIDs include either single or adjuvant therapy for ankylosing spondylitis, bursitis, cancer-related pain, dysmenorrhea, gout, headaches, muscular pain, tendonitis, and pain associated with medical procedures such as dental, gynecological, oral, orthopedic, post-partum and urological procedures.

The amount of active agent administered will depend on a number of factors and will vary from subject to subject, as noted above. Generally, however, and by way of example, a daily dosage of ketorolac using the present formulations and systems will be in the range of approximately 10 mg to 40 mg, a daily dosage of piroxicam using the present formulations and systems will be in the range of approximately 10 mg to 40 mg, and a daily dosage of ibuprofen using the present formulations and systems will be in the range of approximately 200 mg/day to 1600 mg/day.

C. Estrogens and Progestins

Suitable estrogens that may be administered using the compositions and drug delivery systems of the invention include synthetic and natural estrogens such as: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. 17β-Estradiol, ethinylestradiol and mestranol are particularly preferred synthetic estrogenic agents for use in conjunction with the present invention.

Suitable progestins that can be delivered using the compositions and systems of the invention include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, medroxyprogesterone, norethindrone, norethynodrel, d,1-norgestrel and 1-norgestrel are particularly preferred progestins.

It is generally desirable to co-administer a progestin along with an estrogen in female HRT so that the estrogen is not "unopposed." As is well known, estrogen-based therapies are known to increase the risk of endometrial hyperplasia and cancer, as well as the risk of breast cancer, in treated individuals. Co-administration of estrogenic agents with a progestin has been found to decrease the aforementioned risks. Preferred such combinations include, without limitation: 17β-estradiol and medroxyprogesterone acetate; 17β-estradiol and norethindrone; 17β-estradiol and norethynodrel; ethinyl estradiol and d,1-norgestrel; ethinyl estradiol and 1-norgestrel; and megestrol and medroxyprogesterone acetate.

For female HRT, it may be desirable to co-administer a small amount of an androgenic agent along with the progestin and the estrogen, in order to reproduce the complete hormone profile of the premenopausal woman, since low levels of certain androgens are present in premenopausal women. Suitable androgenic agents are discussed in Section D, infra.

Any of the aforementioned steroid drugs may be naturally occurring steroids, synthetic steroids, or derivatives thereof.

As alluded to above, administration of a combination of steroidal active agents is useful in a variety of contexts, as will be readily appreciated by those skilled in the art. For example, the transdermal administration of a progestin with an estrogen may be used in female hormone replacement therapy, so that the symptoms or conditions resulting from altered hormone levels is mitigated or substantially prevented. The present compositions and drug delivery systems are in addition useful to administer progestins and estrogens to treat other conditions and disorders that are responsive to transdermal administration of the combination of active agents. For example, the aforementioned combination is useful to treat the symptoms of premenstrual stress and for female contraception, as noted above. For female hormone replacement therapy, the woman undergoing treatment will generally be of childbearing age or older, in whom ovarian estrogen, progesterone and androgen production has been interrupted either because of natural menopause, surgical procedures, radiation, chemical ovarian ablation or extirpation, or premature ovarian failure. For hormone replacement therapy, and for the other indications described herein including female contraception, the compositions or drug delivery systems are preferably used consecutively so that administration of the active agents is substantially continuous. Transdermal drug administration according to the invention provides highly effective female hormone replacement therapy. That is, the incidence and severity of hot flashes and night sweats are reduced, postmenopausal loss of calcium from bone is minimized, the risk of death from ischemic heart disease is reduced, and the vascularity and health of the Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties. However, preferred transdermal compositions and systems for hormone replacement therapy are capable of delivering about 0.5 to 10.0 mg progestin, e.g., norethindrone, norethindrone acetate or the like, and about 10 to 200 μg estrogen, e.g., 17β-estradiol, ethinyl estradiol, mestranol or the like, over a period of about 24 hours. However, it will be appreciated by those skilled in the art that the desired dose of each individual active agent will depend on the specific active agent as well as on other factors; the minimum effective dose of each active agent is of course preferred.

D. Androgenic Drugs

Suitable androgenic agents that may be used in the formulations of the present invention include, but are not limited to: the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, are particularly preferred androgenic agents for use in conjunction with the present invention. The aforementioned testosterone esters are commercially available or may be readily prepared using techniques known to those skilled in the art or described in the pertinent literature.

The aforementioned androgenic agents are selected from the group consisting of naturally occurring androgens, synthetic androgens, and derivatives thereof. The active agents may be incorporated into the present dosage units and thus administered in the form of a pharmaceutically acceptable derivative, analog, ester, salt, or amide, or the agents may be modified by appending one or more appropriate functionalities to enhance selected biological properties such as penetration through the mucosal tissue. In general, with regard to androgenic agents, esters are preferred relative to salts or other derivatives. Preparation of esters, as noted in the preceding section, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters can be reconverted to the free acids, if desired, by using conventional hydrogenolysis or hydrolysis procedures.

Androgenic drugs such as testosterone (17β-hydroxyandrost-4-en-3-one) are required for sperm production and promote general growth of body tissues. The primary clinical use of androgens is to replace or augment androgen secretion in hypogonadal men. Androgens may also be used to treat certain gynecologic disorders, such as to reduce breast engorgement during the postpartum period. Androgens may also be used to reduce protein loss after trauma, surgery, or prolonged immobilization, or in the treatment of anemia and hereditary angioedema. Androgens may additionally be used in the treatment of male osteoporosis or as metabolic growth stimulators in prepubertal boys.

Testosterone and its derivatives are compounds that are therapeutically effective at fairly low doses, generally in the range of approximately 5 to 10 mg/day.

E. Peptidyl Drugs

Peptidyl drugs that can be administered according to the invetnion include any pharmacologically active peptides, polypeptides or proteins. Once chosen, the peptidyl drug must be prepared or obtained from commercial suppliers for incorporation into a composition or delivery system. The peptidyl drug may be prepared using standard synthetic techniques, recombinant technology or extraction from natural sources.

Synthetic production of peptides, polypeptides and proteins generally employs techniques of standard solid phase peptide synthesis well known in the art. In such a method, the synthesis is sequentially carried out by incorporating the desired amino acid residues one at a time onto a growing peptide chain according to the general principles of solid phase synthesis as described, for example, by Merrifield (1963) *J. Amer. Chem. Soc.* 85:2149–2154. Common to chemical syntheses of peptides, polypeptides and proteins is the protection of reactive side chain groups of the various amino acid moieties with suitable protecting groups which will prevent a chemical reaction from occurring at that site until the protecting group is ultimately removed. It is also well known to protect the α-amino group on an amino acid while that entity reacts at the carboxyl group, followed by the selective removal of the α-amino protecting group to allow a subsequent reaction to take place at that site. Examples of suitable α-amino and side chain protecting groups are well known in the art.

Alternatively, the peptide, polypeptide or protein may be prepared by employing recombinant technology via techniques well known in the art. That is, conventional recombinant techniques may be used, which, as will be appreciated by those skilled in the art, involves constructing DNA encoding the desired amino acid sequence, cloning the DNA into an expression vector, transforming a host cell, e.g., a bacterial, yeast, or mammalian cell, and expressing the DNA to produce the desired peptide, polypeptide or protein.

Additionally, peptides, polypeptides or proteins can be obtained from natural sources such as a human or other animal, and may be extracted from either a living organism or from a cadaver. The material is separated and purified prior to incorporation into a drug delivery system or dosage form. Techniques of separation and purification are well known in the art and include, for example, centrifugation and Although any peptidyl drug may be incorporated into the delivery systems of the present invention, the drug is generally selected from coagulation factors, cytokines, endorphins, kinins, hormones, LHRH (luteinizing hormone-releasing hormone) analogs and other peptidyl drugs that provide a desired pharmacological activity. Of course, the categories provided are not intended to be limiting and simply serve as a means for organization. As will be appreciated, a peptidyl drug may fall into more than one category.

Many coagulation modulators are endogenous proteins that circulate in the blood and interact with other endogenous proteins to control blood coagulation. Preferred coagulation modulators include $\alpha_1$-antitrypsin, $\alpha_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, thrombomodulin and combinations thereof. When applicable, both the "active" and "inactive" versions of these proteins are included.

The cytokines are a large and heterogeneous group of proteins and have a role in the function of the immune system and the control of hematopoiesis, i.e., the production of blood or blood cells. Preferred cytokines include colony stimulating factor 4, heparin binding neurotrophic factor (HBNF), interferon-α, interferon α-2a, interferon α-2b, interferon α-n3, interferon-β, interferon-γ, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), thymopoietin and combinations thereof.

Endorphins are generally peptides or small-chain peptides that activate opiate receptors. Agonist and antagonist derivatives of the naturally-occurring endophins are also contemplated. Representative examples of endorphins or pharmacologically active derivatives include dermorphin, dynorphin, α-endorphin, β-endorphin, γ-endorphin, σ-endorphin [Leu$^5$]enkephalin, [Met$^5$]enkephalin, substance P, and combinations thereof.

Peptidyl hormones may be naturally occurring or may be pharmacologically active derivatives of known hormones. In addition, peptidyl hormones may be human or be derived from other animal sources. Examples of peptidyl hormones that can be administered using the method, composition and delivery system of the invention include, but are not limited to, activin, amylin, angiotensin, atrial natriuretic peptide (ANP), calcitonin (derived from chicken, eel, human, pig, rat, salmon, etc.), calcitonin gene-related peptide, calcitonin N-terminal flanking peptide, cholecystokinin (CCK), ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, ghrelin, glucogon, gonadotropin-releasing factor (GnRF or GNRH), growth hormone releasing factor (GRF, GRH), human chorionic gonadotropin (hCH), inhibin A, inhibin B, insulin (derived from beef, human, pig, etc.), leptin, lipotropin (LPH), luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, triiodothyronine, vasoactive intestinal peptide (VIP), vasopressin (antidiuretic hormone, ADH) and combinations thereof.

Particularly preferred analogues of LHRH include buserelin, deslorelin, fertirelin, goserelin, histrelin, leuprolide (leuprorelin), lutrelin, nafarelin, tryptorelin and combinations thereof.

In addition, the peptidyl drug may be a kinin. Particularly preferred kinins include bradykinin, potentiator B, bradykinin potentiator C, kallidin and combinations thereof.

Still other peptidyl drugs that provide a desired pharmacological activity can be incorporated into the delivery systems of the invention. Examples include abarelix, adenosine deaminase, anakinra, ancestim, alteplase, alglucerase, asparaginase, bivalirudin, bleomycin, bombesin, desmopressin acetate, des-Q14-ghrelin, dornase-α, enterostatin, erythropoeitin, exendin-4, fibroblast growth factor-2, filgrastim, β-glucocerebrosidase, gonadorelin, hyaluronidase, insulinotropin, lepirudin, magainin I, magainin II, nerve growth factor, pentigetide, thrombopoietin, thymosin α-1, thymidin kinase (TK), tissue plasminogen activator, tryptophan hydroxylase, urokinase, urotensin II and combinations thereof.

Particularly preferred systemically active agents that can be administered transdermally in conjunction with the present invention include oxytocin, insulin and LHRH analogues, such as leuprolide.

Preferred agents for local, topical administration are within the broad classes of compounds known to be topically administrable, including, but not limited to, topical antibiotics (e.g., magainin I and magainin II), anti-fungal agents, anti-psoriatic agents, antipruritic agents, antihistamines, antineoplastic agents (e.g., asparaginase and bleomycin), local anesthetics, anti-inflammatory agents and the like.

F. Locally Administered Active Agents

Preferred agents for local, topical administration are within the broad classes of compounds known to be topically administrable, including, but not limited to, topical antibiotics and other anti-acne agents, anti-fungal agents, anti-psoriatic agents, antipruritic agents, antihistamines, antineoplastic agents, local anesthetics, anti-inflammatory agents and the like. Suitable topical antibiotic agents include, but are not limited to, antibiotics of the lincomycin family (referring to a class of antibiotic agents originally recovered from *streptomyces lincolnensis*), antibiotics of the tetracycline family (referring to a class of antibiotic agents originally recovered from *streptomyces aureofaciens*), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl]amino]-1-thio-L-threo-α-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]-amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself (4-(dimethylamino)-1,4,4α,5,5α,6,11,12α-octahydro-3,6,12,12α-pentahydroxy-6-methyl-1,11-dioxo-2-naphthacene-carboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Topical anti-acne agents include keratolytics such as salicyclic acid, retinoic acid (Retin-A"), and organic peroxides, while topical antifungal agents include amphotericin B, benzoic acid, butoconazole, caprylic acid, econazole, fluconazole, itraconazole, ketoconazole, miconazole, nystatin, salicylic acid, and terconazole, and topical antipsoriatic agents include anthralin, azathioprine, calcipotriene, calcitriol, colchicine, cyclosporine, retinoids, and vitamin A. The active agent may also be a topical corticosteroid, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone diproprionate, diflorasone diacetate, fluocinonide, mometasone furoate, triamcinolone acetonide, or the like.

G. Other Active Agents and Analogs

Still other examples of systemically active agents for which the transdermal formulations and drug delivery systems of the invention are preferred include, but are not limited to, the following:

analgesic and anesthetic agents—hydrocodone, hydromorphone, levorphanol, oxycodone, oxymorphone, codeine, morphine, alfentanil, fentanyl, meperidine, sufentanil, buprenorphine, and nicomorphine;

antidepressant drugs—selective serotonin reuptake inhibitors such as sertraline, paroxetine, fluoxetine, fluvoxamine, citalopram, venlafaxine and nefazodone; tricyclic anti-depressants such as amitriptyline, doxepin, nortriptyline, imipramine, trimipramine, amoxapine, desipramine, protriptyline, clomipramine, mirtazapine and maprotiline; other antidepressants such as trazodone, buspirone and bupropion;

attention deficit disorder and attention deficit hyperactivity disorder drugs—methylphenidate and pemoline;

cardiovascular preparations—angiotensin converting enzyme (ACE) inhibitors such as enalapril, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1S-pentyl)amino-2,3,4,5-tetrahydro-2-oxo-3S-1H-1-benzazepine-1-acetic acid or 3-(1-ethoxycarbonyl-3-phenyl-(1S)-propylamino)-2,3,4,5-tetrahydro-2-oxo-(3S)-benzazepine-1-acetic acid monohydrochloride; diuretics; pre- and afterload reducers; cardiac glycosides such as digoxin and digitoxin; inotropes such as amrinone and milrinone; calcium channel blockers such as verapamil, nifedipine, nicardipene, felodipine, isradipine, nimodipine, bepridil, amlodipine and diltiazem; beta-blockers such as metoprolol; pindolol, propafenone, propranolol, esmolol, sotalol and acebutolol; antiarrhythmics such as moricizine, ibutilide, procainamide, quinidine, disopyramide, lidocaine, phenytoin, tocainide, mexiletine, flecainide, encainide, bretylium and amiodarone; cardioprotective agents such as dexrazoxane and leucovorin; vasodilators such as nitroglycerin; cholinergic agents such as arecoline;

CNS agents—bromocriptine, ±trans-1,3,4,4α,5,10β-hexahydro-4-propyl-2H-1-benzopyrano-3,4-bipyridine-9-ol monohydrochloride;

muscle relaxants—baclofen;

nicotine;

narcotic antagonists—naloxone, particularly naloxone hydrochloride;

peripheral vascular dilators—cyclandelate, isoxsuprine and papaverine;

ophthalmic drugs—physostigmine sulfate;

respiratory drugs—such as albuterol, formoterol, nikethamide, theophylline, terbutaline, oxytriphylline, aminophylline and other xanthine derivatives;

topoimerase inhibitors—topotecan and irinotecan.

Genetic material may also be delivered using the methods, formulations and transdermal systems of the invention, e.g., a nucleic acid, RNA, DNA, recombinant RNA, recombinant DNA, antisense RNA, antisense DNA, a ribooligonucleotide, a deooxyriboonucleotide, an antisense ribooligonucleotide, or an antisense deoxyriboooligonucleotide.

Particularly preferred systemically active agents that can be administered transdermally in conjunction with the present invention are as follows: buprenorphine, fentanyl, sufentanil, terbutaline, formoterol, albuterol, theophylline, estradiol, progesterone, scopolamine, enalapril, 1-carboxymethyl-3-1-carboxy-3-phenyl-(1S)-propylamino-2,3,4,5-tetrahydro-1H-(3S)1-benzazepine-2-one, 3-(5-amino-1-carboxy-1S-pentyl)amino-2,3,4,5-tetrahydro-2-oxo-3S-1H-1-benzazepine 1-acetic acid, 3-(1-ethoxycarbonyl-3-phenyl-(1S)-propylamino)-2,3,4,5-tetrahydro-2-oxo-(3S)-benzazepine-1-acetic acid monohydrochloride; nitroglycerin, triprolidine, tripelenamine, diphenhydramine, physostigmine, arecoline, and nicotine. Uncharged, nonionizable active agents are preferred, as are acid addition salts of basic drugs. Of the latter group, the hydrochloride salt is most preferred.

The active agent may be administered, if desired, in the form of a salt, ester, amide, prodrug, derivative, or the like, provided the salt, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

For example, acid addition salts are prepared from the free base—for example, an amine drug—using conventional methodology, and involves reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are halide salts, such as may be prepared using hydrochloric hydrobromic acids.

Conversely, preparation of basic salts of acid moieties which may be present on a phosphodiesterase inhibitor molecule are prepared in a similar manner using a pharmaceutically acceptable base such as sodium hydroxide, potassium hydroxide, ammonium hydroxide, calcium hydroxide, trimethylamine, or the like. Particularly preferred basic salts herein are alkali metal salts, e.g., the sodium salt, and copper salts.

Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety which results in a compound that is therapeutically inactive until modified by an individual's metabolic system.

For those active agents that are chiral in nature and can thus be in enantiomerically pure form or in a racemic mixture, the drug may be incorporated into the present dosage units either as the racemate or in enantiomerically pure form.

The active agent administered also may be one that is cosmetically or "cosmeceutically" effective rather than pharmacologically active. Such agents include, for example, compounds that can reduce the appearance of aging or photodamaged skin, e.g., alpha hydroxyacids, alpha ketoacids, polymeric hydroxyacids, moisturizers, collagen, marine extract, and antioxidants such as ascorbic acid (vitamin C), $\alpha$-tocopherol (Vitamin E), $\beta$-tocopherol, $\gamma$-tocopherol, $\delta$-tocopherol, $\epsilon$-tocopherol, $\zeta_1$-tocopherol, $\zeta_2$-tocopherol, $\eta$-tocopherol, and retinol (vitamin A), and/or cosmetically acceptable salts, esters, amides, or other derivatives thereof. A preferred tocopherol compound is $\alpha$-tocopherol. Additional cosmetic agents include those that are capable of improving oxygen supply in skin tissue, as described, for example, in International Patent Publication Nos. WO 94/00098 and WO 94/00109. Sunscreens may also be included.

Formulations

The method of delivery of the active agent may vary, but necessarily involves application of a formulation or drug delivery system containing a hydroxide-releasing agent to a predetermined area of the skin or other tissue for a period of time sufficient to provide the desired local or systemic effect. The method may involve direct application of the composition as an ointment, gel, cream, or the like, or may involve use of a drug delivery device. In either case, water must be present in order for the hydroxide-releasing agent to generate hydroxide ions and thus enhance the flux of the active agent through the patient's body surface. Thus, a formulation or drug reservoir may be aqueous, i.e., contain water, or may be nonaqueous and used in combination with an occlusive overlayer so that moisture evaporating from the body surface is maintained within the formulation or transdermal system during drug administration. In some cases, however, e.g., with an occlusive gel, a nonaqueous formulation may be used with or without an occlusive layer.

Suitable formulations include ointments, creams, gels, lotions, pastes, and the like. Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions, which are preferred for delivery of cosmetic agents, are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethyl-ammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethyl-ammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. They are generally although not necessarily formed from lipids, preferably charged lipids such as phospholipids. Preparation of lipidic microspheres is well known in the art and described in the pertinent texts and literature.

Various additives, known to those skilled in the art, may be included in the topical formulations. For example, solvents, including relatively small amounts of alcohol, may be used to solubilize certain drug substances. Other optional additives include opacifiers, antioxidants, fragrance, colorant, gelling agents, thickening agents, stabilizers, surfactants and the like. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

For those drugs having an unusually low rate of permeation through the skin or mucosal tissue, it may be desirable to include a second permeation enhancer in the formulation in addition to the hydroxide-releasing agent, although in a preferred embodiment the hydroxide-releasing agent is administered without any other permeation enhancers. Any other enhancers should, like the hydroxide-releasing agent itself, minimize the possibility of skin damage, irritation, and systemic toxicity. Examples of suitable secondary enhancers (or "co-enhancers") include, but are not limited to, ethers such as diethylene glycol monoethyl ether (available commercially as Transcutol[7]) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80) and lecithin (U.S. Pat. No. 4,783,450; see also ); alcohols such as ethanol, propanol, octanol, benzyl alcohol, and the like; fatty acids such as lauric acid, oleic acid and valeric acid; fatty acid esters such as isopropyl myristate, isopropyl palmitate, methylpropionate, and ethyl oleate; polyols and esters thereof such as polyethylene glycol, and polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}MSO$ may also be used, but are less preferred. As noted earlier herein, *Percutaneous Penetration Enhancers*, eds. Smith et al. (CRC Press, 1995) provides an excellent overview of the field and further information concerning possible secondary enhancers for use in conjunction with the present invention.

The formulation may also contain irritation-mitigating additives to minimize or eliminate the possibility of skin irritation or skin damage resulting from the drug, the enhancer, or other components of the formulation. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the formulations.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the patient and physician. Preferred formulations will typically contain on the order of about 0.5 wt. % to 50 wt. %, optimally about 10 wt. % to 30 wt. %, active agent.

Drug Delivery Systems

An alternative and preferred method involves the use of a drug delivery system, e.g., a topical or transdermal "patch," wherein the active agent is contained within a laminated structure that is to be affixed to the skin. In such a structure, the drug composition is contained in a layer, or "reservoir," underlying an upper backing layer. The laminated structure may contain a single reservoir, or it may contain multiple reservoirs.

In one embodiment, the reservoir comprises a polymeric matrix of a pharmaceutically acceptable adhesive material that serves to affix the system to the skin during drug delivery; typically, the adhesive material is a pressure-sensitive adhesive (PSA) that is suitable for long-term skin contact, and which should be physically and chemically compatible with the active agent, hydroxide-releasing agent, and any carriers, vehicles or other additives that are present. Examples of suitable adhesive materials include, but are not limited to, the following: polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene). Preferred adhesives are polyisobutylenes.

The backing layer functions as the primary structural element of the transdermal system and provides the device with flexibility and, preferably, occlusivity. The material used for the backing layer should be inert and incapable of absorbing drug, hydroxide-releasing agent or components of the formulation contained within the device. The backing is preferably comprised of a flexible elastomeric material that serves as a protective covering to prevent loss of drug and/or vehicle via transmission through the upper surface of the patch, and will preferably impart a degree of occlusivity to the system, such that the area of the body surface covered by the patch becomes hydrated during use. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. The materials used as the backing layer are either occlusive or permeable, as noted above, although occlusive backings are preferred, and are generally derived from synthetic polymers (e.g., polyester, polyethylene, polypropylene, polyurethane, polyvinylidine chloride, and polyether amide), natural polymers (e.g., cellulosic materials), or macroporous woven and nonwoven materials.

During storage and prior to use, the laminated structure includes a release liner. Immediately prior to use, this layer is removed from the device so that the system may be affixed to the skin. The release liner should be made from a drug/vehicle impermeable material, and is a disposable element which serves only to protect the device prior to application. Typically, the release liner is formed from a material impermeable to the pharmacologically active agent and the hydroxide-releasing agent, and which is easily stripped from the transdermal patch prior to use.

In an alternative embodiment, the drug-containing reservoir and skin contact adhesive are present as separate and distinct layers, with the adhesive underlying the reservoir. In such a case, the reservoir may be a polymeric matrix as described above. Alternatively, the reservoir may be comprised of a liquid or semisolid formulation contained in a closed compartment or "pouch," or it may be a hydrogel reservoir, or may take some other form. Hydrogel reservoirs are particularly preferred herein. As will be appreciated by those skilled in the art, hydrogels are macromolecular networks that absorb water and thus swell but do not dissolve in water. That is, hydrogels contain hydrophilic functional groups that provide for water absorption, but the hydrogels are comprised of crosslinked polymers that give rise to aqueous insolubility. Generally, then, hydrogels are comprised of crosslinked hydrophilic polymers such as a polyurethane, a polyvinyl alcohol, a polyacrylic acid, a polyoxyethylene, a polyvinylpyrrolidone, a poly (hydroxyethyl methacrylate) (poly(HEMA)), or a copolymer or mixture thereof. Particularly preferred hydrophilic polymers are copolymers of HEMA and polyvinylpyrrolidone.

Additional layers, e.g., intermediate fabric layers and/or rate-controlling membranes, may also be present in any of these drug delivery systems. Fabric layers may be used to facilitate fabrication of the device, while a rate-controlling membrane may be used to control the rate at which a component permeates out of the device. The component may be a drug, a hydroxide-releasing agent, an additional enhancer, or some other component contained in the drug delivery system.

A rate-controlling membrane, if present, will be included in the system on the skin side of one or more of the drug reservoirs. The materials used to form such a membrane are selected to limit the flux of one or more components contained in the drug formulation. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like.

Generally, the underlying surface of the transdermal device, i.e., the skin contact area, has an area in the range of about 5 $cm^2$ to 200 $cm^2$, preferably 5 $cm^2$ to 100 $cm^2$, more preferably 20 $cm^2$ to 60 $cm^2$. That area will vary, of course, with the amount of drug to be delivered and the flux of the drug through the body surface. Larger patches will necessary to accommodate larger quantities of drug, while smaller patches can be used for smaller quantities of drug and/or drugs that exhibit a relatively high permeation rate.

Such drug delivery systems may be fabricated using conventional coating and laminating techniques known in the art. For example, adhesive matrix systems can be prepared by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture. In general, transdermal systems of the invention are fabricated by solvent evaporation, film casting, melt extrusion, thin film lamination, die cutting, or the like. The hydroxide-releasing agent will generally be incorporated into the device during patch manufacture rather than subsequent to preparation of the device. Thus, for acid addition salts of basic drugs (e.g., hydrochloride salts of amine drugs, such as phenylpropanolamine hydrochloride), the hydroxide-releasing agent will neutralize the drug during manufacture of the drug delivery system, resulting in a final drug delivery system in which the drug is present in nonionized, neutral form along with an excess of hydroxide-releasing agent to serve as a permeation enhancer. For nonionized acidic drugs, the hydroxide-releasing agent will neutralize such drugs by converting them to the ionized drug in salt form.

In a preferred delivery system, an adhesive overlayer that also serves as a backing for the delivery system is used to better secure the patch to the body surface. This overlayer is sized such that it extends beyond the drug reservoir so that adhesive on the overlayer comes into contact with the body surface. The overlayer is useful because the adhesive/drug reservoir layer may lose its adhesion a few hours after application due to hydration. By incorporating such adhesive overlayer, the delivery system remains in place for the required period of time.

Other types and configurations of transdermal drug delivery systems may also be used in conjunction with the method of the present invention, i.e., the use of a hydroxide-releasing agent as a permeation enhancer, as will be appreciated by those skilled in the art of transdermal drug delivery. See, for example, Ghosh, *Transdermal and Topical Drug Delivery Systems* (Interpharm Press, 1997), particularly Chapters 2 and 8.

As with the topically applied formulations of the invention, the composition containing drug and hydroxide-releasing agent within the drug reservoir(s) of these laminated system may contain a number of components. In some cases, the drug and hydroxide-releasing agent may be delivered "neat," i.e., in the absence of additional liquid. In most cases, however, the drug will be dissolved, dispersed or suspended in a suitable pharmaceutically acceptable vehicle, typically a solvent or gel. Other components that may be present include preservatives, stabilizers, surfactants, and the like.

The invention accordingly provides a novel and highly effective means for increasing the flux of an active agent through the body surface (skin or mucosal tissue) of a human or animal. The hydroxide-releasing agents discussed herein, employed in specific amounts relative to a formulation or drug reservoir, may be used as permeation enhancers with a wide variety of drugs and drug types, including free acids, free bases, acid addition salts of basic drugs, basic addition salts of acidic drugs, nonionizable drugs, peptides and proteins. Surprisingly, the increase in permeation is not accompanied by any noticeable tissue damage, irritation, or sensitization. The invention thus represents an important advance in the field of drug delivery.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. Furthermore, the practice of the present invention will employ, unless otherwise indicated, conventional techniques of drug formulation, particularly topical and transdermal drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

All patents, patent applications, publications and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

An in vitro skin permeation study was conducted using three estradiol transdermal systems. The formulations used to prepare these systems are listed in Table 1, which includes weight and weight percent of each component of the formulations. The weight of sodium hydroxide was 0 g, 0.0155 g, and 0.025 g for formulation #Est-P18, #Est-P19 and #Est-P20 respectively. Each formulation was coated onto a release liner and dried in an oven at 55° C. for two hours to remove water and other solvents. The dried drug-in-adhesive/release liner film was laminated to a backing film. The backing/drug-in-adhesive/release liner laminate was then cut into discs with a diameter of $^{11}/_{16}$ inch. The theoretical percent weight for each ingredient after drying (calculated assuming all volatile ingredients were completely removed during drying) is set forth in Table 2.

The in vitro permeation of estradiol through human cadaver skin from these discs was performed using Franz-type diffusion cells with a diffusion area of 1 $cm^2$. The volume of receiver solution was 8 ml. Human cadaver skin was cut to a proper size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with 10% ethanol/90% water solution. The receiver solution was completely withdrawn and replaced with fresh ethanol/water solution at each time point. The samples taken were analyzed by HPLC to determine the concentration of estradiol in the receiver solution. The cumulative amount of estradiol that permeated through the human cadaver skin was calculated using the measured estradiol concentrations in the receiver solutions, which were plotted versus time and shown in FIG. 1.

The pH of the patch was measured using the following procedures. A 2.5 $cm^2$ circular patch was punched out. Ten ml of purified water was pipetted into a glass vial, and a stir bar was added; the liner was removed from the patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours. After 18 hours, the stir bar was removed from the vial and the pH of the solution determined using a calibrated pH meter.

The measured pHs for the estradiol transdermal systems are listed in Table 3.

TABLE 1

Weight and Weight Percent of Components
(Based on Total Solution Weight)
for Three Estradiol Transdermal Systems

|  | Est-P18 | Est-P19 | Est-P20 |
|---|---|---|---|
| Estradiol | 0.0313 g (0.5%) | 0.0322 g (0.5%) | 0.0308 g (0.5%) |
| NaOH | 0 | 0.0155 g (0.3%) | 0.025 g (0.4%) |
| DI water | 0 | 0.4155 g (6.9%) | 0.425 g (7.0%) |
| PIB* adhesive (30% solid) | 4 g (66.3%) | 4 g (66.0%) | 4 g (65.8%) |
| Methylal | 1.8 g (29.8%) | 1.4 g (23.1%) | 1.4 g (23.0%) |
| Ethanol | 0.2 g (3.3%) | 0.2 g (3.3%) | 0.2 g (3.3%) |

PIB = polyisobutylene

TABLE 2

Weight and Theoretical Weight Percent
of Components in the Dried Film
for Three Estradiol Transdermal Systems

|  | Est-P18 | Est-P19 | Est-P20 |
|---|---|---|---|
| Estradiol | 0.0313 g | 0.0322 g | 0.0308 g |
|  | (2.5%) | (2.6%) | (2.5%) |
| NaOH | 0 | 0.0155 g | 0.025 g |
|  |  | (1.2%) | (2.0%) |
| PIB adhesive | 1.2 g | 1.2 g | 1.2 g |
|  | (97.5%) | (96.2%) | (95.6%) |

TABLE 3 pH for Three Estradiol Transdermal Systems

|  | Est-P18 | Est-P19 | Est-P20 |
|---|---|---|---|
| pH | 7.22 | 8.75 | 8.90 |

The cumulative amount of estradiol that permeated across human cadaver skin at 24 hours increased from 0.22 µg/cm² to 7.01 µg/cm² when the calculated sodium hydroxide concentration in the dried patch was increased from 0% to 2.0%. The cumulative amount of estradiol that permeated across human cadaver skin at 24 hours from the system containing 1.2% NaOH (Est-P19) was 4.55 µg/cm², which was about 20 times higher than that from the formulation without NaOH (0.22 µg/cm², #Est-P18).

The pH of the estradiol patch measured using the procedures listed above increased from 7.22 to 8.90 when the calculated sodium hydroxide concentration in the dried patch was increased from 0% to 2.0%.

EXAMPLE 2

An in vitro skin permeation study was conducted using four ketoprofen transdermal systems. The formulations used to prepare these systems are listed in Table 4, which includes weight and weight percent of each component of the formulations. The weight of sodium hydroxide was 0 g, 0.19 g, 0.215 g, and 0.225 g for formulation #Keto-P3H16, -P3H17, P3H18, and -P3H19, respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into discs with a diameter of ¹¹⁄₁₆ inch. The theoretical percent weight for each ingredient after drying (calculated assuming all volatile ingredients were completely removed during drying) is set forth in Table 5.

The in vitro permeation of ketoprofen through human cadaver skin from these discs was performed using Franz diffusion cells with a diffusion area of 1 cm². Human cadaver skin was cut to a proper size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Five diffusion cells were used for each formulation.

Normal saline was used as the receiver solution. The volume of receiver solution was 8 ml. The entire receiver solution was collected and replaced with fresh saline at each time point. The receiver solution collected was analyzed by HPLC to determine the concentration of ketoprofen. The cumulative amount of ketoprofen that permeated across the human cadaver skin was calculated using the measured ketoprofen concentrations in the receiver solutions, which were plotted versus time and shown in FIG. 2.

Since ketoprofen is a free acid, it reacts with NaOH. The concentration of NaOH in the system after the reaction is completed depends on the amount of ketoprofen added. The remaining NaOH concentration after the reaction is completed is defined as "excess NaOH concentration," which is calculated by the following equation.

$$[NaOH_{excess}] = [NaOH_{total}] - [NaOH_{needed\ for\ neutralization}]$$

The excess NaOH concentrations for four ketoprofen systems, #Keto-P3H16, -P3H17, -P3H18, and -P3H19, were calculated and are set forth in Table 6.

The pH of each patch was measured using the procedures of Example 1. The results are also set forth in Table 6.

TABLE 4

Weight and Weight Percent of
Each Component (Based on Total Solution
Weight) for Four Ketoprofen Transdermal Systems

|  | Keto-P3H16 | Keto-P3H17 | Keto-P3H18 | Keto-P3H19 |
|---|---|---|---|---|
| Ketoprofen | 1.2 g | 1.2 g | 1.2 g | 1.2 g |
|  | (16.7%) | (15.8%) | (15.7%) | (15.7%) |
| NaOH | 0 | 0.19 g | 0.215 g | 0.225 g |
|  |  | (2.5%) | (2.8%) | (2.9%) |
| DI water | 0 | 0.19 g | 0.215 g | 0.225 g |
|  |  | (2.5%) | (2.8%) | (2.9%) |
| PIB adhesive | 4 g | 4 g | 4 g | 4 g |
| (30% solid) | (55.6%) | (52.8%) | (52.4%) | (52.3%) |
| Methylal | 2 g | 2 g | 2 g | 2 g |
|  | (27.8%) | (26.4%) | (26.2%) | (26.1%) |

TABLE 5

Weight and Theoretical Weight
Percent of Each Component in the Dried
Film for Four Ketoprofen Transdermal Systems

|  | Keto-P3H16 | Keto-P3H17 | Keto-P3H18 | Keto-P3H19 |
|---|---|---|---|---|
| Ketoprofen | 1.2 g | 1.2 g | 1.2 g | 1.2 g |
|  | (50%) | (45.9%) | (45.9%) | (45.7%) |
| NaOH | 0 | 0.19 g | 0.215 g | 0.225 g |
|  |  | (7.3%) | (8.2%) | (8.6%) |
| PIB adhesive | 1.2 g | 1.2 g | 1.2 g | 1.2 g |
|  | (50%) | (46.3%) | (45.9%) | (45.7%) |

TABLE 6

Excess NaOH Concentration and pH of Four
Ketoprofen Transdermal Systems

|  | Keto-P3H16 | Keto-P3H17 | Keto-P3H18 | Keto-P3H19 |
|---|---|---|---|---|
| Excess NaOH Concentration |  | 0.05% | 1.00% | 1.38% |
| pH | 3.68 | 8.60 | 10.10 | 10.57 |

Figure 2:
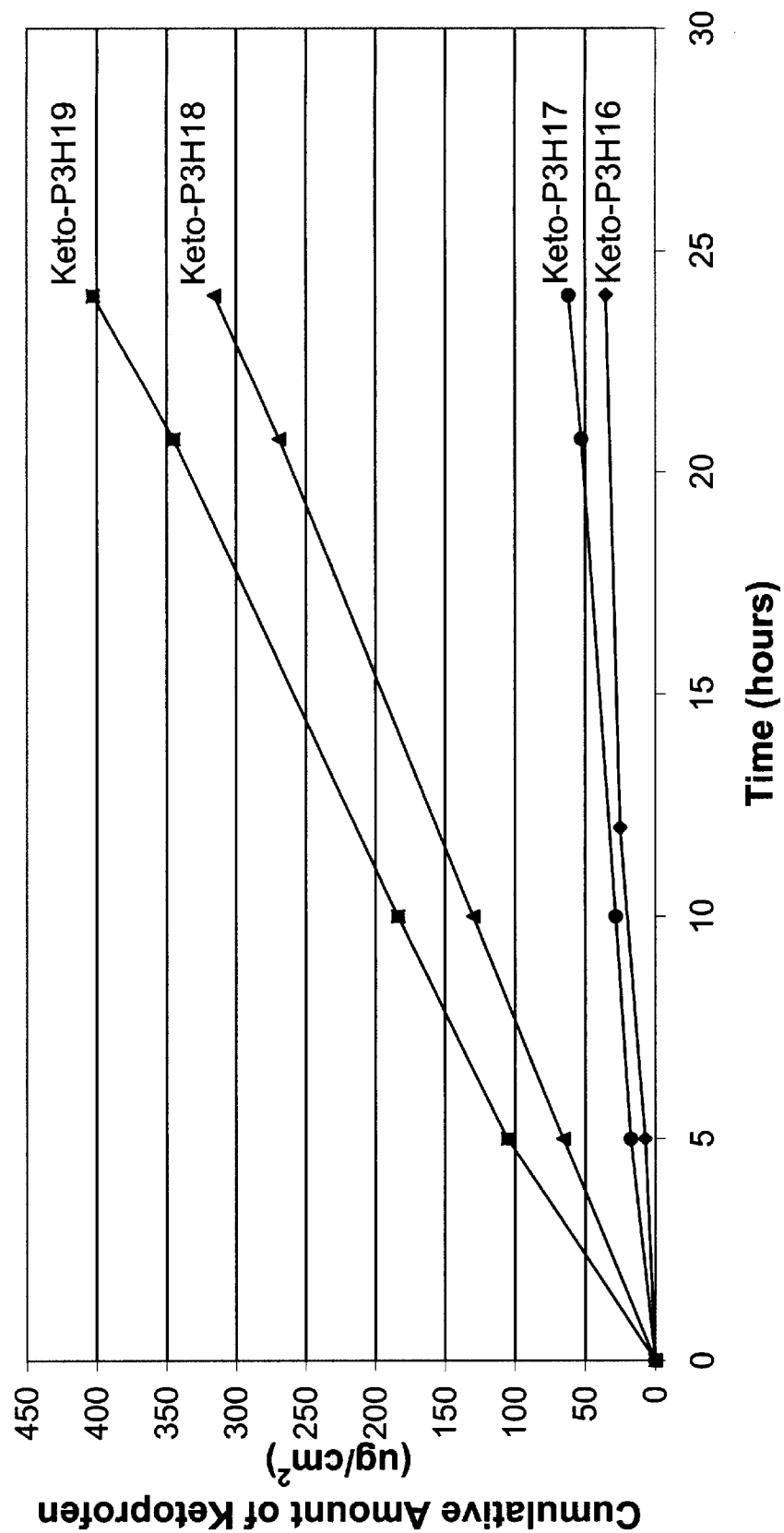
FIG. 2 is a graph illustrating the cumulative amount of ketoprofen from a matrix patch as described in Example 2.

Even though patch #Keto-P3H17 contained 7.3% NaOH (Table 5), the cumulative amount of ketoprofen that permeated across the human cadaver skin at 24 hours (61.7

µg/cm², FIG. 2) was only slightly higher than that from the formulation without NaOH (Keto-P3H16, 35.2 µg/cm²). This may be due to the consumption of NaOH by the reaction between NaOH and ketoprofen, which reduced the NaOH concentration to only 0.05% as the excess NaOH concentration (Table 6). This result indicated that the permeation of ketoprofen could be enhanced with an excess NaOH concentration as low as 0.05%.

The cumulative amount of ketoprofen that permeated across human cadaver skin at 24 hours increased from 61.7 µg/cm² to 402.7 µg/cm² when the calculated excess NaOH concentration in the dried patch was increased from 0.05% to 1.38%. The cumulative amount of ketoprofen that permeated across human cadaver skin at 24 hours from the formulation with an excess NaOH concentration of 1.00% (Keto-P3H18, 315.8 µg/cm²) is about 5 times higher than that from the formulation with an excess NaOH concentration of 0.05% (Keto-P3H17, 61.7 µg/cm²).

The pH of the ketoprofen patch determined using the procedure of Example 1 increased from 8.60 to 10.57 when the calculated excess NaOH concentration in the dried patch was increased from 0.05% to 1.38%.

EXAMPLE 3

An in vitro skin permeation study was conducted using four phenylpropanolamine hydrochloride (PPA-HCl) transdermal systems. The formulations used to prepare these systems are listed in Table 7, which includes weight and weight percent of each component in the formulations. The weight of sodium hydroxide was 0 g, 0.165 g, 0.195 g, and 0.23 g for formulation #PPA-N7, -N1, -N2, -and -N5, respectively. Each formulation was coated onto a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of 11/16 inch. The theoretical percent weight for each component after drying (calculated assuming all the volatile ingredients were completely removed during drying) is listed in Table 8.

The in vitro permeation of PPA-HCl through human cadaver skin from these discs was performed using Franz-type diffusion cells with a diffusion area of 1 cm². The volume of receiver solution was 8 ml. Human cadaver skin was cut to the desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

Figure 3:
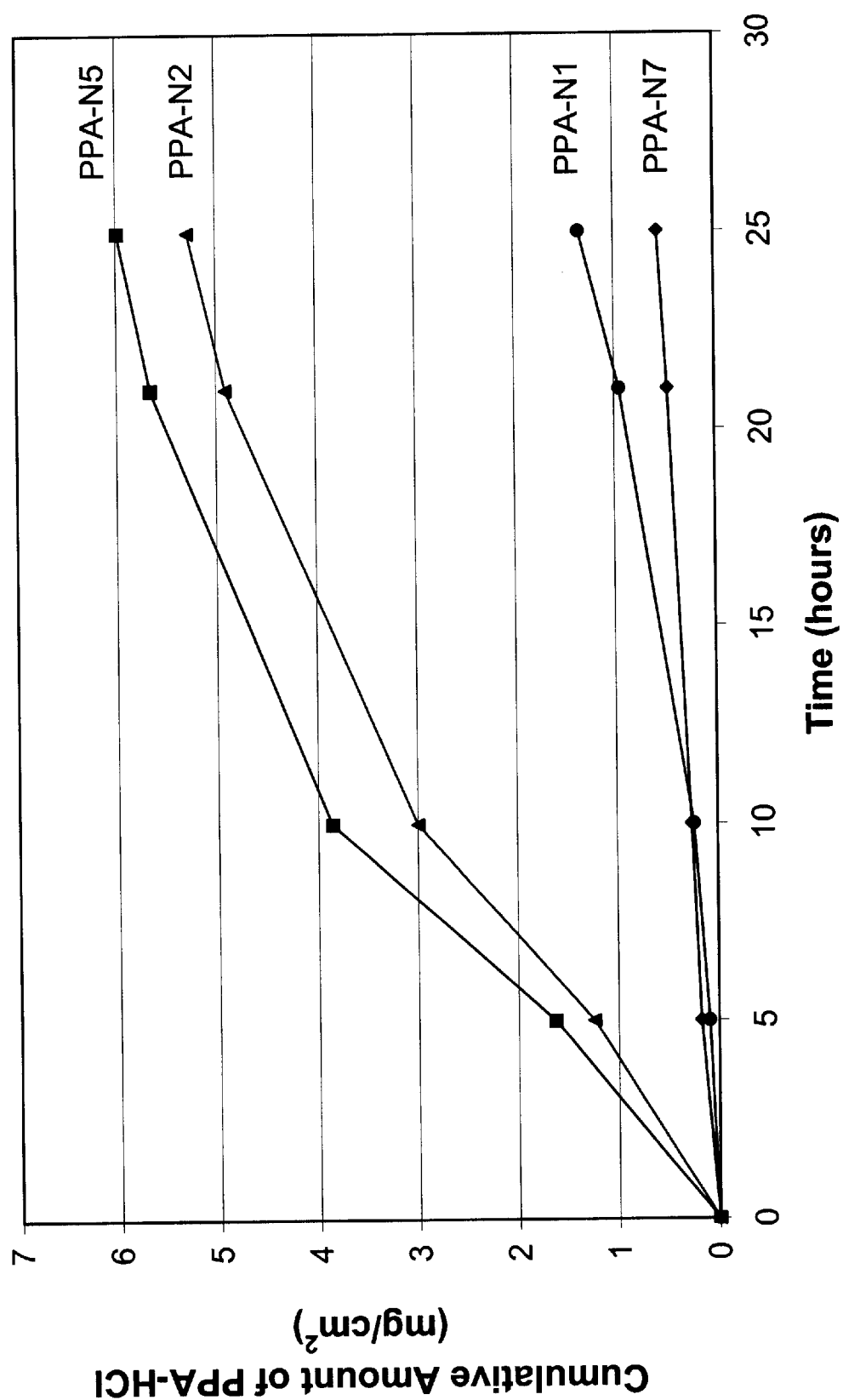
FIG. 3 is a graph illustrating the cumulative amount of phenylpropanolamine from a matrix patch as described in Example 3.

The cells were filled with DI water. The receiver solution was completely withdrawn and replaced with fresh DI water at each time point. The samples taken were analyzed by an HPLC for the concentration of PPA-HCl in the receiver solution. The cumulative amount of PPA-HCl that permeated across the human cadaver skin was calculated using the measured PPA-HCl concentrations in the receiver solutions, which were plotted versus time and shown in FIG. 3.

Since PPA-HCl is an acid addition salt of a free base, it reacts with NaOH. The concentration of NaOH in the system after the reaction is completed depends on the amount of PPA-HCl added. The remaining NaOH concentration after the reaction is completed is defined as "excess NaOH concentration," calculated as explained in the foregoing example. The excess NaOH concentration for three PPA-HCl systems, #PPA-N7, -N1, -N2, -and -N5, were calculated and listed in Table 9.

The pH of each patch was determined using the procedure of Example 1, and results are listed in Table 9.

TABLE 7

Weight and Weight Percent of Each Component
(Based on Total Solution Weight)
for Four PPA-HCl Transdermal Systems

|  | PPA-N7 | PPA-N1 | PPA-N2 | PPA-N5 |
|---|---|---|---|---|
| PPA-HCl | 0.75 g | 0.75 g | 0.75 g | 0.75 g |
|  | (8.5%) | (8.2%) | (8.1%) | (8.1%) |
| NaOH | 0 | 0.165 g | 0.195 g | 0.23 g |
|  |  | (1.8%) | (2.1%) | (2.5%) |
| DI water | 1.1 g | 1.265 g | 1.295 g | 1.33 g |
|  | (12.4%) | (13.8%) | (14.0%) | (14.3%) |
| Propylene glycol | 0.5 g | 0.5 g | 0.5 g | 0.5 g |
|  | (5.6%) | (5.4%) | (5.4%) | (5.4%) |
| Methylal | 1 g | 1 g | 1 g | 1 g |
|  | (11.3%) | (10.9%) | (10.8%) | (10.7%) |
| Heptane | 1.5 g | 1.5 g | 1.5 g | 1.5 g |
|  | (16.9%) | (16.3%) | (16.2%) | (16.1%) |
| PIB adhesive (30% solid) | 4 g | 4 g | 4 g | 4 g |
|  | (45.2%) | (43.6%) | (43.3%) | (43.0%) |

TABLE 8

Weight and Theoretical Weight Percent of
Each Component in the Dried Film
for Four PPA-HCl Transdermal Systems

|  | PPA-N7 | PPA-N1 | PPA-N2 | PPA-N5 |
|---|---|---|---|---|
| PPA-HCl | 0.75 g | 0.75 g | 0.75 g | 0.75 g |
|  | (30.6%) | (28.7%) | (28.4%) | (28.0%) |
| NaOH | 0 | 0.165 g | 0.195 g | 0.23 g |
|  |  | (6.3%) | (7.4%) | (8.6%) |
| PIB adhesive | 1.2 g | 1.2 g | 1.2 g | 1.2 g |
|  | (49.0%) | (45.9%) | (45.4%) | (44.8%) |
| Propylene glycol | 0.5 g | 0.5 g | 0.5 g | 0.5 g |
|  | (20.4%) | (19.1%) | (18.9%) | (18.7%) |

TABLE 9

Excess NaOH Concentration and pH of
Four PPA-HCl Transdermal Systems

|  | PPA-N7 | PPA-N1 | PPA-N2 | PPA-N5 |
|---|---|---|---|---|
| Excess NaOH Concentration |  | 0.20% | 1.33% | 2.62% |
| pH | 7.33 | 10.08 | 10.16 | 10.88 |

Even though patch #PPA-N1 contained 6.3% NaOH (Table 8), the cumulative amount of PPA-HCl that permeated across the human cadaver skin at 24 hours from this formulation (1.35 mg/cm², FIG. 3) was only slightly higher than that from the formulation without NaOH (PPA-N7, 0.56 mg/cm²). This may be due to the consumption of NaOH by the reaction between NaOH and PPA-HCl, which reduced the NaOH concentration to only 0.20% as the excess NaOH concentration shown in Table 9. This result indicated that the permeation of PPA-HCl could be enhanced with an excess NaOH concentration as low as 0.20%.

The cumulative amount of PPA-HCl across human cadaver skin at 24 hours increased from 1.35 mg/cm² to 5.99 mg/cm² when the calculated excess NaOH concentration in the dried patch was increased from 0.20% to 2.62%. The cumulative amount of PPA-HCl across human cadaver skin at 24 hours from the formulation with an excess NaOH concentration of 1.33% (PPA-N2, 5.2 mg/cm$^2$) is about 5 times higher than that from the formulation with an excess NaOH concentration of 0.20% (PPA-N1, 1.35 mg/cm$^2$).

The pH of the PPA-HCl patch increased from 10.08 to 10.88 when the calculated excess NaOH concentration in the dried patch was increased from 0.20% to 2.62%. Skin irritation could be related to the pH of the patch, which depends on the excess NaOH concentration.

EXAMPLE 4

A human skin irritation study was performed using seven transdermal systems, which are listed below.

Patch #Keto-IT1 (containing no ketoprofen, no NaOH)
Patch #Keto-IT2 (containing ketoprofen, no NaOH)
Patch #Keto-IT7
Patch #Keto-IT8
Patch #Keto-IT9
Patch #Keto-IT10
Patch containing petrolatum The patch containing petrolatum was used as a control, which was an occlusive chamber (Hilltop, Cincinnati, Ohio) containing petrolatum held in place with paper tape. The following procedures were used to prepare the systems with the exception of the system containing petrolatum. The formulations used to prepare these systems are listed in Table 10, which include weight and weight percent of each component in the formulations. The weight of sodium hydroxide was 0.6 g, 0.65 g, 0.69 g, and 0.73 g for formulation #Keto-IT7, -IT8, -IT9 and BIT10 respectively. Each formulation was coated onto a release liner and dried in an oven at 55° C. for two hours to remove water and other solvents. The dried drug-in-adhesive/release liner film was laminated to a backing film. The backing/drug-in-adhesive/release liner laminate was cut into round discs with a diameter of 2 inch. The theoretical percent weight for each ingredient after drying is listed in Table 11, which was calculated assuming all the volatile ingredients were completely removed during drying.

Ten healthy human subjects were included in the skin irritation study. Each subject wore seven patches listed above on the arms for 24 hours. An adhesive film with a diameter of ⅞ inch was applied over each system on the skin except the petrolatum patch to secure the system and to make the system occlusive for 24 hours. After 24 hours, the patches were removed and the skin was scored on a 0–4 scale. The scoring scale employed is listed below. The skin was scored again at 48 hours.

0=negative
+=equivocal reaction (0.5)
1=erythema
2=erythema and induration
3=erythema, induration and vesicles
4=bullae A skin permeation study was performed from formulation #Keto-IT7, -IT8, -IT9 and BIT10. Franz diffusion cells with a diffusion area of 1 cm$^2$ were used in this study. Human cadaver skin was cut to a proper size and placed on a flat surface with the stratum corneum side facing up. The release liner was peeled away from the round disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

Normal saline was used as the receiver solution. The volume of receiver solution was 8 ml. The receiver solution was collected at 24 hours and analyzed by an HPLC for the concentration of ketoprofen. The amount of ketoprofen that permeated across the human cadaver skin was calculated using the measured ketoprofen concentrations in the receiver solutions, which are listed in Table 12.

The excess NaOH concentrations for four ketoprofen systems, #Keto -IT7, -IT8, -IT9 and BIT10 were calculated as the described in Example 2 and listed in Table 12.

The pH of the patch was determined using the procedure of Example 1, and the measured pH for each ketoprofen transdermal system is also listed in Table 12.

TABLE 10

Weight and Weight Percent of Each Component (Based on Total Solution Weight) for Four Ketoprofen Transdermal Systems

|  | Keto-IT7 | Keto-IT8 | Keto-IT9 | Keto-IT10 |
|---|---|---|---|---|
| Ketoprofen | 2.4 g (14.0%) | 2.4 g (14.0%) | 2.4 g (13.9%) | 2.4 g (13.8%) |
| NaOH | 0.6 g (3.5%) | 0.65 g (3.8%) | 0.69 g (4.0%) | 0.73 g (4.2%) |
| DI water | 0.6 g (3.5%) | 0.65 g (3.8%) | 0.69 g (4.0%) | 0.73 g (4.2%) |
| PIB adhesive (30% solid) | 8 g (46.8%) | 8 g (46.5%) | 8 g (46.3%) | 8 g (46.1%) |
| Tetraglycol | 0.5 g (2.9%) | 0.5 g (2.9%) | 0.5 g (2.9%) | 0.5 g (2.9%) |
| Isopropylmyristate | 0.4 g (2.3%) | 0.4 g (2.3%) | 0.4 g (2.3%) | 0.4 g (2.3%) |
| Methyl salicylate | 0.6 g (3.5%) | 0.6 g (3.5%) | 0.6 g (3.5%) | 0.6 g (3.5%) |
| Methylal | 4 g (23.4%) | 4 g (23.3%) | 4 g (23.3%) | 4 g (23.0%) |

TABLE 11

Weight and Theoretical Weight Percent of Each Component in the Dried Film for Four Ketoprofen Transdermal Systems

|  | Keto-IT7 | Keto-IT8 | Keto-IT9 | Keto-IT10 |
|---|---|---|---|---|
| Ketoprofen | 2.4 g (34.8%) | 2.4 g (34.5%) | 2.4 g (34.3%) | 2.4 g (34.1%) |
| NaOH | 0.6 g (8.7%) | 0.65 g (9.4%) | 0.69 g (9.9%) | 0.73 g (10.4%) |
| PIB adhesive | 2.4 g (34.0%) | 2.4 g (34.5%) | 2.4 g (34.3%) | 2.4 g (34.1%) |
| Tetraglycol | 0.5 g (7.2%) | 0.5 g (7.2%) | 0.5 g (7.2%) | 0.5 g (7.1%) |
| Isopropyl-myristate | 0.4 g (5.8%) | 0.4 g (5.8%) | 0.4 g (5.7%) | 0.4 g (5.7%) |
| Methyl salicylate | 0.6 g (8.7%) | 0.6 g (8.6%) | 0.6 g (8.6%) | 0.6 g (8.5%) |

TABLE 12

Excess NaOH Concentration, Cumulative Amount of Ketoprofen across Skin at 24 Hours and pH of Four Ketoprofen Transdermal Systems

|  | Keto-IT7 | Keto-IT8 | Keto-IT9 | Keto-IT10 |
|---|---|---|---|---|
| pH | 10.06 | 10.81 | 11.04 | 11.18 |
| Excess NaOH Concentration | 3.22% | 3.92% | 4.47% | 5.01% |
| Cumulative amount across skin at 24 hours | 0.17 | 0.34 | 0.54 | 1.52 |

The cumulative amount of ketoprofen that permeated across the human cadaver skin at 24 hours increased from 0.17 mg/cm$^2$ to 1.52 mg/cm$^2$ when the calculated excess NaOH concentration in the dried patch was increased from 3.22% to 5.01%. The excess NaOH concentration and the cumulative amount of ketoprofen across skin at 24 hours and the patch pH for Keto-IT8 was 0.34 mg/cm$^2$ and 10.81 respectively, which was about the same as those for Keto-P3H18 shown in Example 2 (0.32 mg/cm$^2$, pH=10.10). However, the excess NaOH concentration for Keto-IT8 (3.92%) was higher than that for Keto-P3H18 (1.00%), which may be due to the consumption of NaOH through reactions between NaOH and components other than ketoprofen in the Keto-IT8 formulation.

The irritation scores obtained indicate that irritation from this patch was insignificant.

EXAMPLE 5

An in vitro skin permeation study was conducted using four ibuprofen transdermal gels. The formulations used to prepare these gels are listed in Table 13, which includes weight and weight percent of each component in the formulations. The weight of sodium hydroxide was 0 g, 0.115 g, 0.135 g, and 0.15 g for formulation #Ibu-GH81, -GH82, -GH83, and -GH84 respectively.

The in vitro permeation of ibuprofen through human cadaver skin from these gels was performed using Franz diffusion cells with a diffusion area of 1 cm$^2$. Human cadaver skin was cut to a proper size and clamped between the donor and receiver chambers of the diffusion cell with the stratum corneum side facing the donor solution. Three diffusion cells were used for each formulation.

Figure 4:
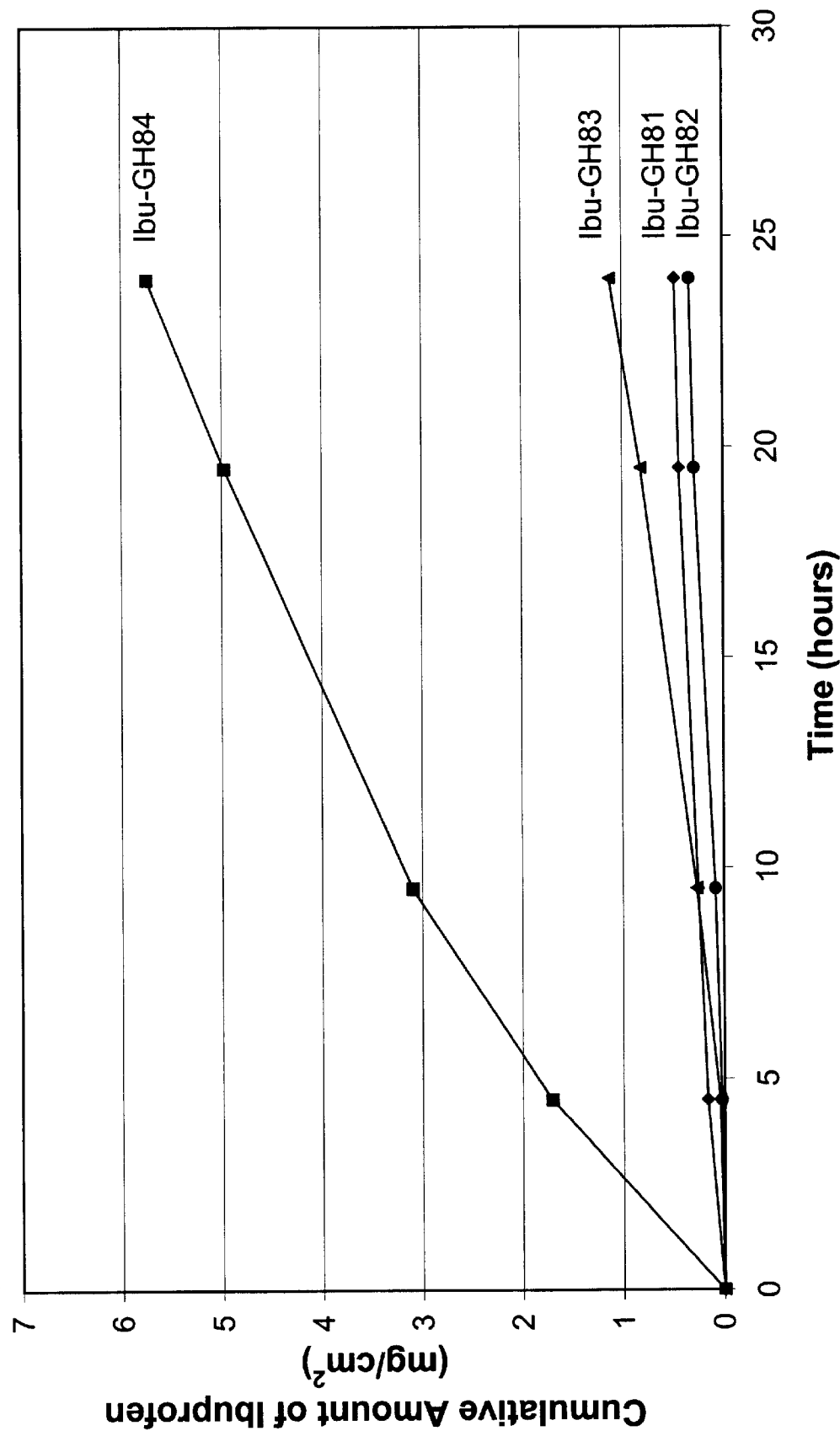
FIG. 4 is a graph illustrating the cumulative amount of ibuprofen from a gel described in Example 5.

Normal saline was used as the receiver solution. The volume of receiver solution was 8 ml. The entire receiver solution was collected and replaced with fresh saline at each time point. The receiver solution collected was analyzed by an HPLC for the concentration of ibuprofen. The cumulative amount of ibuprofen across human cadaver skin was calculated using the measured ibuprofen concentrations in the receiver solutions, which were plotted versus time and shown in FIG. 4.

The excess NaOH concentration for three ibuprofen gels, #Ibu-GH81, -GH82, -GH83, and -GH84, were calculated and listed in Table 14.

The pH of each gel was determined using the procedure of Example 1 and the results are listed in Table 14.

TABLE 13

Weight and Weight Percent of Each Component (Based on Total Solution Weight) for Four Ibuprofen Transdermal Gels

|  | Ibu-GH81 | Ibu-GH82 | Ibu-GH83 | Ibu-GH84 |
|---|---|---|---|---|
| Ibuprofen | 0.6 g (36.8%) | 0.6 g (32.3%) | 0.6 g (31.6%) | 0.6 g (31.1%) |
| NaOH | 0 | 0.115 g (6.2%) | 0.135 g (7.1%) | 0.15 g (7.8%) |
| Ethanol | 0.4 g (24.5%) | 0.4 g (21.5%) | 0.4 g (21.1%) | 0.4 g (20.7%) |
| DI Water | 0.6 g (36.8%) | 0.715 g (38.4%) | 0.735 g (38.7%) | 0.75 g (38.9%) |
| HPMCP* | 0.03 g (1.8%) | 0.03 g (1.6%) | 0.03 g (1.6%) | 0.03 g (1.6%) |

*HPMCP Hydroxypropyl methyl cellulose phthalate

TABLE 14

Excess NaOH Concentration and pH of Four Ibuprofen Transdermal Gels

|  | Ibu-GH81 | Ibu-GH82 | Ibu-GH83 | Ibu-GH84 |
|---|---|---|---|---|
| Excess NaOH Concentration |  | 0% | 0.98% | 1.74% |
| pH | 4.57 | 6.58 | 11.83 | 12.22 |

The cumulative amount of ibuprofen across human cadaver skin at 24 hours increased from 0.33 mg/cm$^2$ to 5.74 mg/cm$^2$ (FIG. 4) when the calculated excess NaOH concentration in the gel was increased from 0% to 1.74%. The cumulative amount of ibuprofen that permeated across the human cadaver skin at 24 hours from the formulation with an excess NaOH concentration of 0.98% (Ibu-GH83, 1.12 mg/cm$^2$) is about 3 times higher than that from the formulation with an excess NaOH concentration of 0% (Ibu-GH82, 0.33 mg/cm$^2$).

The pH of the ibuprofen patch (determined using the procedures of the previous examples) increased from 6.58 to 12.22 when the calculated excess NaOH concentration in the gel was increased from 0% to 1.74%. The skin irritation could be related to the pH of the gel, which depends on the excess NaOH concentration.

EXAMPLE 6

Figure 5:
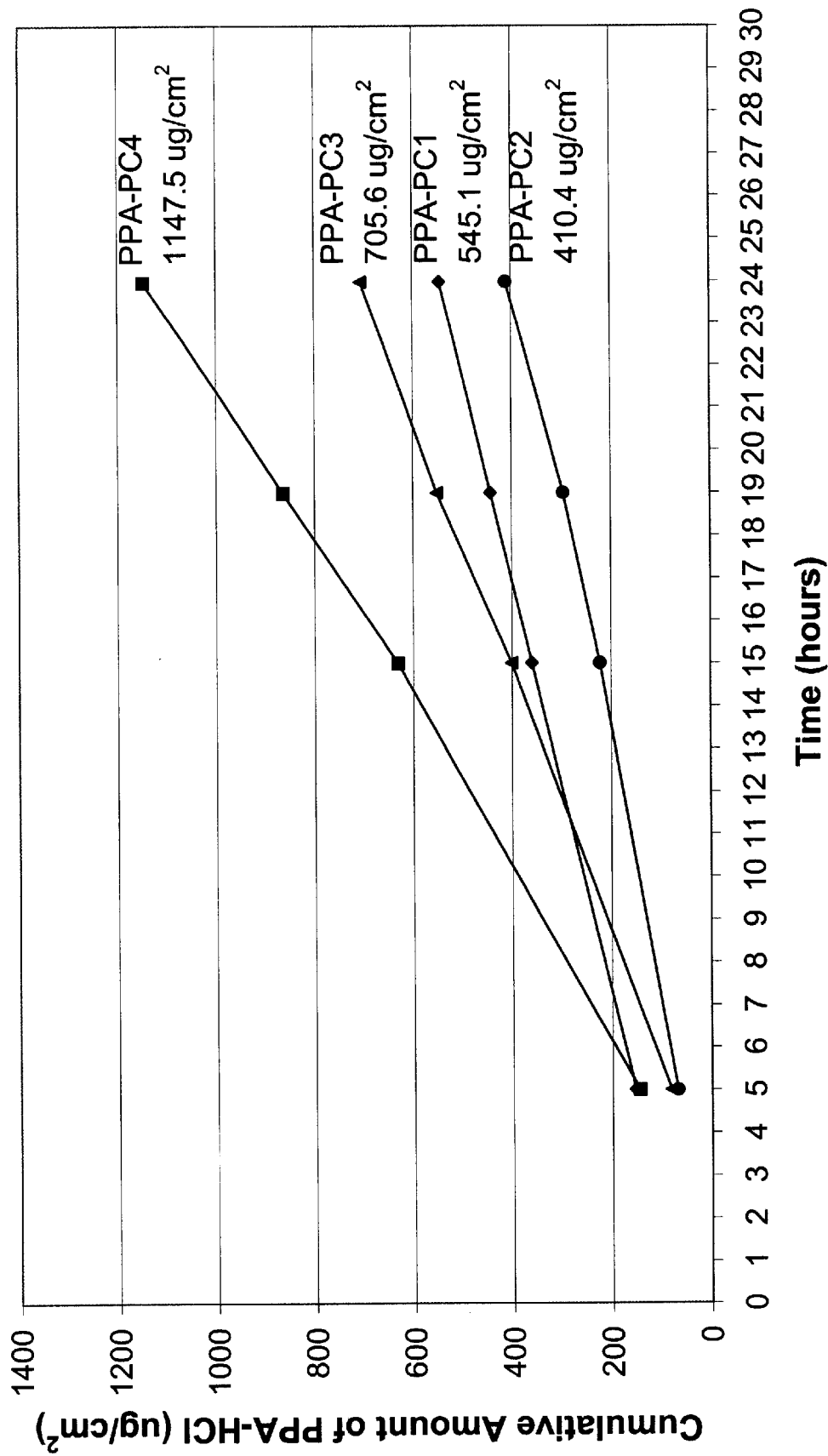
FIG. 5 is a graph illustrating the cumulative amount of phenylpropanolamine from a matrix patch as described in Example 6.

An in vitro skin permeation study was conducted using four phenylpropanolamine hydrochloride (PPA-HCl) transdermal systems. The formulations used to prepare these systems are listed in Table 15, which includes weight and weight percent of each component in the formulations. The weight of sodium carbonate (Na$_2$CO$_3$) was 0 g, 0.29 g, 0.44 g, and 0.74 g for formulations #PPA-PC1, -PC2, -PC3, and -PC4 respectively. The matrix patches were prepared and evaluated using the same procedures as set forth in Example 3. The theoretical percent weight for each ingredient after drying (calculated assuming all the volatile ingredients were completely removed during drying) is listed in Table 16. The cumulative amount of PPA-HCl across human cadaver skin was calculated using the measured PPA-HCl concentrations in the receiver solutions, which were shown in Table 17 and FIG. 5.

Since PPA-HCl is a salt of a free base, it reacts with Na$_2$CO$_3$. The concentration of Na$_2$CO$_3$ in the system after the reaction is completed depends on the amount of PPA-HCl added. The remaining sodium carbonate concentration after the reaction is completed is defined as "excess Na$_2$CO$_3$ concentration," which is calculated by the following equation.

$$[Na_2CO_3\ _{excess}] = [Na_2CO_3\ _{total}] - [Na_2CO_3\ _{needed\ for\ neutralization}]$$

The excess Na$_2$CO$_3$ for four PPA-HCl systems, #PPA-PC1, -PC2, -PC3 and -PC4 concentration were calculated and listed in Table 18.

The pH of the patch was determined using the procedure of example 1 and the results are listed in Table 18.

TABLE 15

Weight and Weight Percent of Each Component (Based on Total Solution Weight) for Four PPA-HCl Transdermal Systems

|  | PPA-PC1 | PPA-PC2 | PPA-PC3 | PPA-PC4 |
|---|---|---|---|---|
| PPA-HCl | 0.5 g (6.7%) | 0.5 g (5.7%) | 0.5 g (5.6%) | 0.5 g (5.5%) |
| $Na_2CO_3$ | 0 | 0.29 g (3.3%) | 0.44 g (5.0%) | 0.74 g (8.1%) |
| DI water | 1.0 g (13.5%) | 2.0 g (23.0%) | 2.0 g (22.6%) | 2.0 g (21.9%) |
| Methyl alcohol | 0.5 g (6.7%) | 0.5 g (5.7%) | 0.5 g (5.6%) | 0.5 g (5.5%) |
| Propylene glycol | 0.2 g (2.7%) | 0.2 g (2.3%) | 0.2 g (2.3%) | 0.2 g (2.2%) |
| HPMC | 0.01 g (0.1%) | 0.01 g (0.1%) | 0.01 g (0.1%) | 0.01 g (0.1%) |
| Heptane | 1.2 g (16.2%) | 1.2 g (13.8%) | 1.2 g (13.6%) | 1.2 g (13.1%) |
| PIB adhesive (30% solid) | 4 g (54.0%) | 4 g (46.0%) | 4 g (45.2%) | 4 g (45.2%) |

TABLE 16

Weight and Theoretical Weight Percent of Each Component in the Dried Film for Four PPA-HCl Transdermal Systems

|  | PPA-PC1 | PPA-PC2 | PPA-PC3 | PPA-PC4 |
|---|---|---|---|---|
| PPA-HCl | 0.5 g (26.2%) | 0.5 g (22.7%) | 0.5 g (21.3%) | 0.5 g (18.9%) |
| $Na_2CO_3$ | 0 | 0.29 g (13.2%) | 0.44 g (18.7%) | 0.74 g (27.9%) |
| Propylene glycol | 0.2 g (10.5%) | 0.2 g (9.1%) | 0.2 g (8.5%) | 0.2 g (7.5%) |
| HPMC | 0.01 g (0.5%) | 0.01 g (0.5%) | 0.01 g (0.4%) | 0.01 g (0.4%) |
| PIB adhesive | 1.2 g (62.8%) | 1.2 g (54.5%) | 1.2 g (51.1%) | 1.2 g (45.3%) |

TABLE 17

Cumulative Amount of PPA-HCl across human cadaver skin for PPA-HCl Transdermal Systems ($\mu g/cm^2$)

|  | PPA-PC1 | PPA-PC2 | PPA-PC3 | PPA-PC4 |
|---|---|---|---|---|
| 5 hours | 152.8 | 68.0 | 81.1 | 144.8 |
| 15 hours | 359.5 | 222.7 | 400.8 | 631.2 |
| 19 hours | 442.7 | 295.7 | 551.5 | 864.3 |
| 24 hours | 545.1 | 410.4 | 705.6 | 1147.5 |

TABLE 18

Excess $Na_2CO_3$ Concentration and pH of Four PPA-HCl Transdermal Systems

|  | PPA-PC1 | PPA-PC2 | PPA-PC3 | PPA-PC4 |
|---|---|---|---|---|
| Excess $Na_2CO_3$ Concentration | — | 0.4% | 6.7% | 16.7% |
| pH | 6.54 | 9.81 | 9.86 | 10.17 |

Even though patch #PPA-PC2 contained 13.2% $Na_2CO_3$ (Table 16), the cumulative amount of PPA-HCl that permeated across the human cadaver skin at 24 hours (410.4 $\mu g/cm^2$, Table 17) was lower than that from the formulation without $Na_2CO_3$ (PPA-PC1, 545.1 $\mu g/cm^2$). This may be due to the consumption of $Na_2CO_3$ by the reaction between $Na_2CO_3$ and PPA-HCl, which reduced the $Na_2CO_3$ concentration to only 0.4% as the excess $Na_2CO_3$ concentration (Table 18).

When the calculated excess $Na_2CO_3$ concentration in the dried patch was further increased from 0.4% to 16.7%, the cumulative amount of PPA-HCl that permeated across the human cadaver skin at 24 hours was increased from 410.4 to 1147.5 $\mu g/cm^2$. This result indicated that the permeation of PPA-HCl could be enhanced by $Na_2CO_3$, even though the required excess $Na_2CO_3$ concentration is higher than that of NaOH. Greater amounts of $Na_2CO_3$ may be necessary because it is a weaker base compared to NaOH and the molecular weight of $Na_2CO_3$ is higher than that of NaOH.

The pH of the PPA-HCl patch measured using the procedures listed above increased from 9.81 to 10.17 when the calculated excess $Na_2CO_3$ concentration in the dried patch was increased from 0.4% to 16.7%.

EXAMPLE 7

Figure 6:
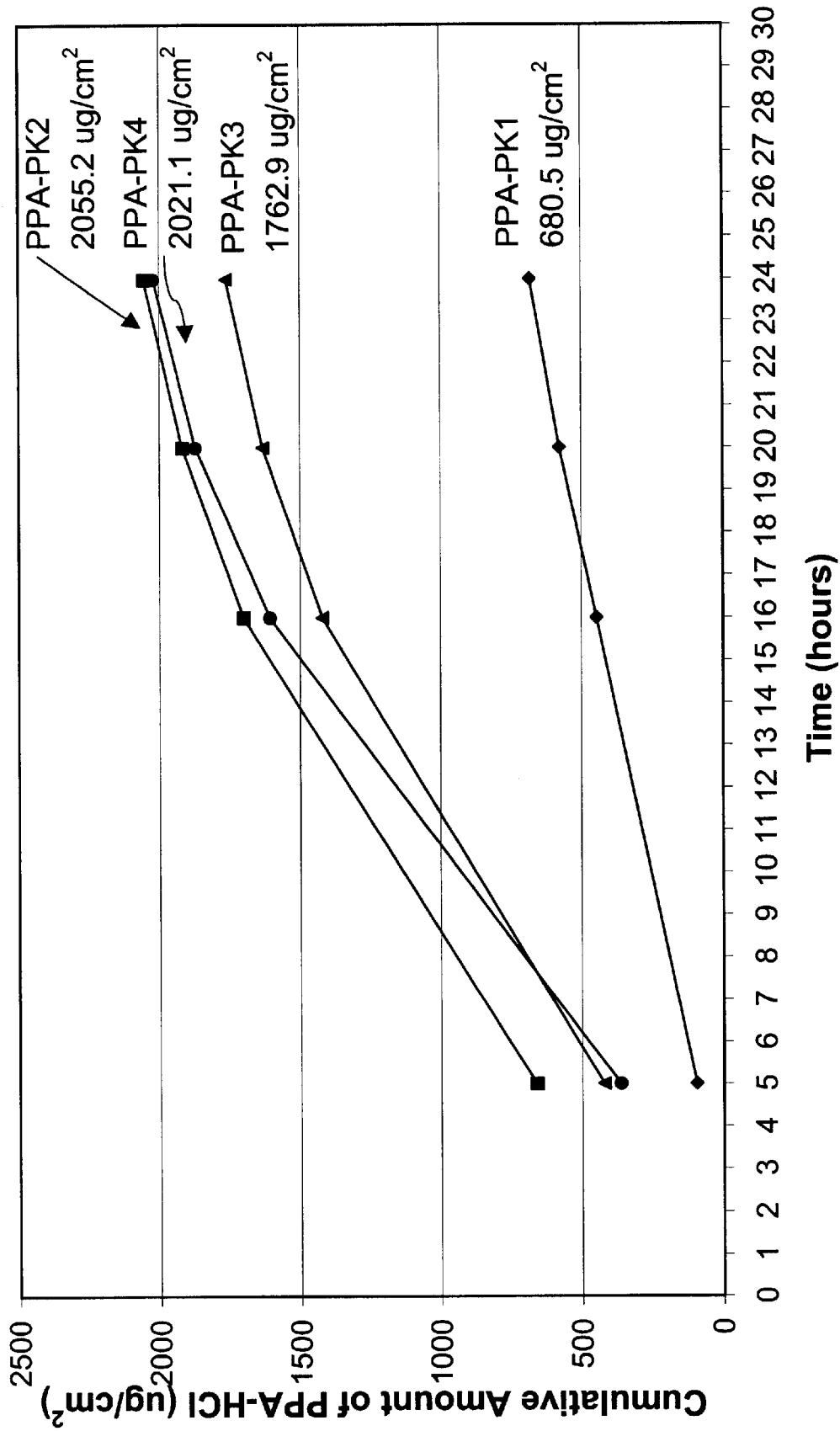
FIG. 6 is a graph illustrating the cumulative amount of phenylpropanolamine from a matrix patch as described in Example 7.

An in vitro skin permeation study was conducted using four phenylpropanolamine hydrochloride (PPA-HCl) transdermal systems. The formulations used to prepare these systems are listed in Table 19, which includes weight and weight percent of each component in the formulations. The weight of potassium phosphate, tribasic ($K_3PO_4$) was 0 g, 0.57 g, 0.6 g, and 0.66 g for formulation #PPA-PK1, -PK2, -PK3, and -PK4 respectively. The matrix patches were prepared and evaluated using the same procedures as set forth in Example 3. The theoretical percent weight for each ingredient after drying (calculated assuming all the volatile ingredients were completely removed during drying) is listed in Table 20. The cumulative amount of PPA-HCl across human cadaver skin was calculated using the measured PPA-HCl concentrations in the receiver solutions, which were shown in Table 21 and FIG. 6.

Since PPA-HCl is a salt of a free base, it reacts with $K_3PO_4$. The concentration of $K_3PO_4$ in the system after the reaction is completed depends on the amount of PPA-HCl added. The remaining $K_3PO4$ concentration after the reaction is completed is defined as "excess $K_3PO4$ concentration," which is calculated by the following equation.

$$[K_3PO_4\ _{excess}] = [K_3PO_4\ _{total}] - [K_3PO_4\ _{needed\ for\ neutralization}]$$

The excess $K_3PO_4$ concentration for four PPA-HCl systems, #PPA-PK1, -PK2, -PK3 and -PK4 were calculated and listed in Table 8.

The pH of the patch was determined using the procedure of Example 1 and the results are listed in Table 22.

TABLE 19

Weight and Weight Percent of Each Component (Based on Total Solution Weight) for Four PPA-HCl Transdermal Systems

|  | PPA-PK1 | PPA-PK2 | PPA-PK3 | PPA-PK4 |
|---|---|---|---|---|
| PPA-HCl | 0.5 g (6.6%) | 0.5 g (6.1%) | 0.5 g (6.1%) | 0.5 g (6.1%) |
| $K_3PO_4$ | 0 | 0.57 g (7.0%) | 0.6 g (7.3%) | 0.66 g (8.0%) |
| DI water | 1.0 g (13.2%) | 1.0 g (12.2%) | 1.0 g (12.2%) | 1.0 g (12.1%) |
| Propylene glycol | 0.5 g (6.6%) | 0.5 g (6.1%) | 0.5 g (6.1%) | 0.5 g (6.1%) |
| Methyl alcohol | 0.5 g (6.6%) | 0.5 g (6.1%) | 0.5 g (6.1%) | 0.5 g (6.1%) |
| PIB adhesive (30% solid) | 4 g (52.6%) | 4 g (49.0%) | 4 g (48.8%) | 4 g (48.4%) |
| HPMC | 0.1 g (1.3%) | 0.1 g (1.2%) | 0.1 g (1.2%) | 0.1 g (1.2%) |
| Heptane | 1 g (13.2%) | 1 g (12.2%) | 1 g (12.2%) | 1 g (12.1%) |

TABLE 20

Weight and Theoretical Weight Percent of Each Component in the Dried Film for Four PPA-HCl Transdermal Systems

|  | PPA-PK1 | PPA-PK2 | PPA-PK3 | PPA-PK4 |
|---|---|---|---|---|
| PPA-HCl | 0.5 g (21.7%) | 0.5 g (17.4%) | 0.5 g (17.2%) | 0.5 g (16.9%) |
| $K_3PO_4$ | 0 | 0.57 g (19.9%) | 0.6 g (20.7%) | 0.66 g (22.3%) |
| Propylene glycol | 0.5 g (21.7%) | 0.5 g (17.4%) | 0.5 g (17.2%) | 0.5 g (16.9%) |
| PIB adhesive | 1.2 g (52.2%) | 1.2 g (41.8%) | 1.2 g (41.4%) | 1.2 g (40.5%) |
| HPMC | 0.1 g (4.3%) | 0.1 g (3.5%) | 0.1 g (3.4%) | 0.1 g (3.4%) |

TABLE 21

Cumulative Amount of PPA-HCl across human cadaver skin for PPA-HCl Transdermal Systems ($\mu g/cm^2$)

|  | PPA-PK1 | PPA-PK2 | PPA-PK3 | PPA-PK4 |
|---|---|---|---|---|
| 5 hours | 94.7 | 660.0 | 421.6 | 362.9 |
| 16 hours | 445.9 | 1701.3 | 1420.3 | 1607.5 |
| 20 hours | 576.8 | 1919.2 | 1633.1 | 1872.5 |
| 24 hours | 680.5 | 2055.2 | 1762.9 | 2021.1 |

TABLE 22

Excess $K_3PO_4$ Concentration and pH of Four PPA-HCl Transdermal Systems

|  | PPA-PK1 | PPA-PK2 | PPA-PK3 | PPA-PK4 |
|---|---|---|---|---|
| Excess $K_3PO_4$ Concentration | — | 0.2% | 1.2% | 3.2% |
| pH | 6.75 | 9.68 | 9.62 | 10.08 |

The cumulative amount of PPA-HCl that permeated across the human cadaver skin at 24 hours for PPA-PK2 (2055.2 $\mu g/cm^2$, Table 21) with a calculated excess $K_3PO_4$ concentration of 0.2% was three times higher than that from the formulation without $K_3PO_4$ (PPA-PK1, 680.5 $\mu g/cm^2$). This result indicated that the permeation of PPA-HCl could be enhanced with an excess $K_3PO_4$ concentration as low as 0.2%.

The cumulative amount of PPA-HCl across human cadaver skin at 24 hours remained about the same when the excess $K_3PO_4$ concentration in the dried patch was increased from 0.2% to 3.2% (Tables 21 and 22).

The pH of the PPA-HCl patch measured using the procedures listed above increased from 6.75 to 9.68 when the $K_3PO_4$ concentration in the dried patch was increased from 0% to 19.9% (or 0.2% excess $K_3PO_4$ concentration, Tables 20 and 22). However, the pH of the PPA-HCl patch remained about the same when the excess $K_3PO_4$ concentration in the dried patch was further increased from 0.2% to 3.2% (Table 22).

EXAMPLE 8

Figure 7:
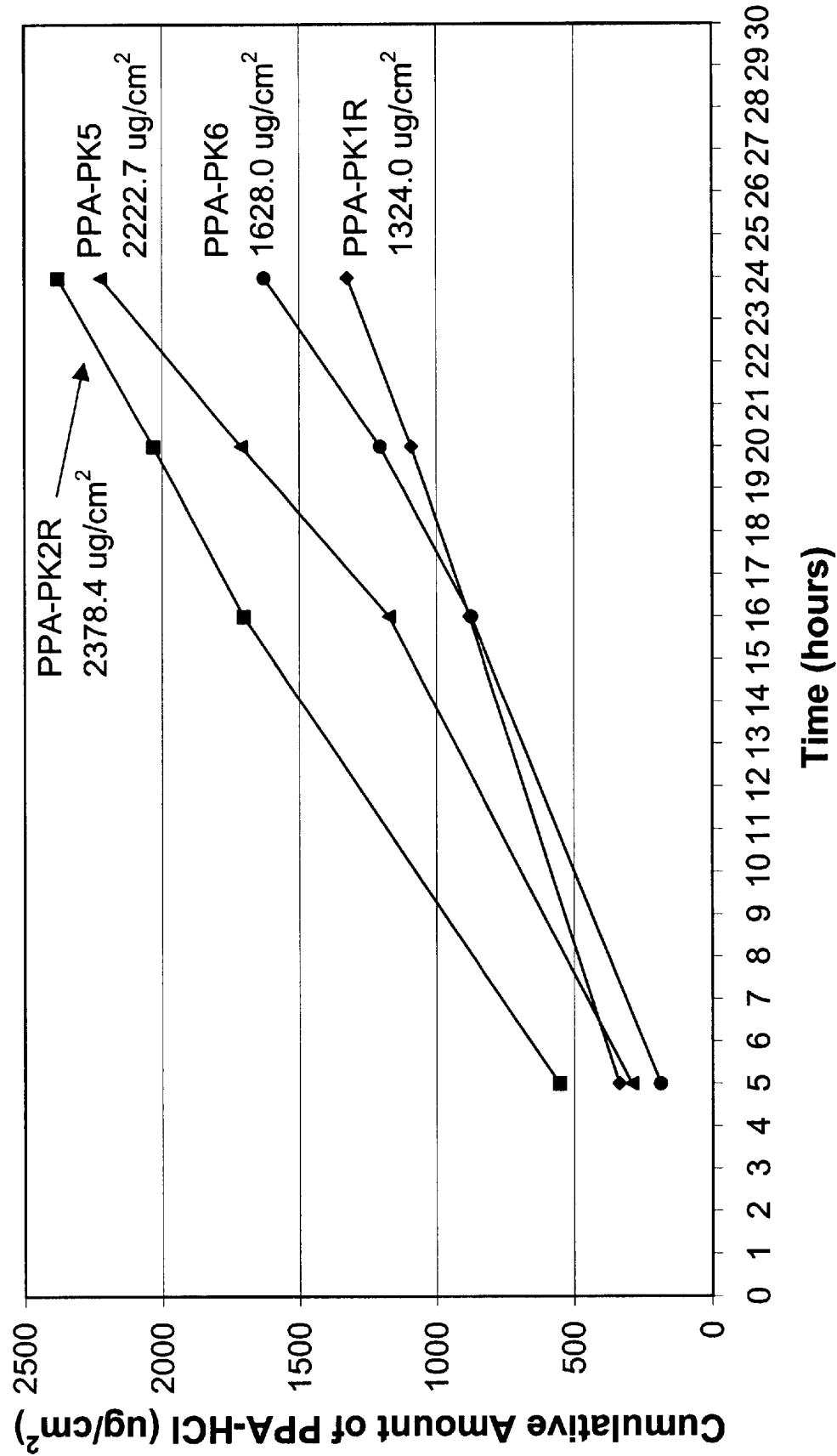
FIG. 7 is a graph illustrating the cumulative amount of phenylpropanolamine from a matrix patch as described in Example 8.

An in vitro skin permeation study was conducted using four phenylpropanolamine hydrochloride (PPA-HCl) transdermal systems. The formulations used to prepare these systems are listed in Table 23, which includes weight and weight percent of each component in the formulations. The weight of potassium phosphate, tribasic ($K_3PO_4$) was 0 g, 0.57 g, 0.73 g, and 1.05 g for formulation #PPA-PK1R, -PK2R, -PK5, and -PK6 respectively. The matrix patches were prepared and evaluated using the same procedures as set forth in Example 3. The theoretical percent weight for each ingredient after drying (calculated assuming all the volatile ingredients were completely removed during drying) is listed in Table 24. The cumulative amount of PPA-HCl across human cadaver skin was calculated using the measured PPA-HCl concentrations in the receiver solutions, which were shown in Table 25 and FIG. 7.

The excess $K_3PO_4$ concentration for four PPA-HCl systems, #PPA-PK1R, -PK2R, -PK5 and -PK6 were calculated using the procedure of Example 7 and the results are listed in Table 26.

The pH of each patch was determined using the procedure of Example 1 and the results are listed in Table 26.

TABLE 23

Weight and Weight Percent of Each Component (Based on Total Solution Weight) for Four PPA-HCl Transdermal Systems

|  | PPA-PK1R | PPA-PK2R | PPA-PK5 | PPA-PK6 |
|---|---|---|---|---|
| PPA-HCl | 0.5 g (6.9%) | 0.5 g (6.4%) | 0.5 g (6.3%) | 0.5 g (6.1%) |
| $K_3PO_4$ | 0 | 0.57 g (7.3%) | 0.73 g (9.2%) | 1.05 g (12.7%) |
| DI water | 1.0 g (13.9%) | 1.0 g (12.9%) | 1.0 g (12.6%) | 1.0 g (12.1%) |
| Methyl alcohol | 0.5 g (6.9%) | 0.5 g (6.4%) | 0.5 g (6.3%) | 0.5 g (6.1%) |
| Propylene glycol | 0.2 g (2.8%) | 0.2 g (2.6%) | 0.2 g (2.5%) | 0.2 g (2.4%) |
| HPMC | 0.01 g (0.1%) | 0.01 g (0.1%) | 0.01 g (0.1%) | 0.01 g (0.1%) |
| Heptane | 1 g (13.9%) | 1 g (12.9%) | 1 g (12.6%) | 1 g (12.1%) |
| PIB adhesive (30% solid) | 4 g (55.5%) | 4 g (51.4%) | 4 g (50.4%) | 4 g (48.4%) |

TABLE 24

Weight and Theoretical Weight Percent of Each Component in the Dried Film for Four PPA-HCl Transdermal Systems

|  | PPA-PK1R | PPA-PK2R | PPA-PK5 | PPA-PK6 |
|---|---|---|---|---|
| PPA-HCl | 0.5 g (26.2%) | 0.5 g (20.2%) | 0.5 g (18.9%) | 0.5 g (16.5%) |
| $K_3PO_4$ | 0 | 0.57 g (23.6%) | 0.73 g (27.7%) | 1.05 g (35.5%) |
| Propylene glycol | 0.2 g (10.5%) | 0.2 g (8.1%) | 0.2 g (7.6%) | 0.2 g (6.8%) |
| HPMC | 0.01 g (0.5%) | 0.01 g (0.4%) | 0.01 g (0.4%) | 0.01 g (0.3%) |
| PIB adhesive | 1.2 g (62.8%) | 1.2 g (48.4%) | 1.2 g (45.5%) | 1.2 g (40.5%) |

TABLE 25

Cumulative Amount of PPA-HCl across human cadaver skin for PPA-HCl Transdermal Systems ($\mu g/cm^2$)

|  | PPA-PK1R | PPA-PK2R | PPA-PK5 | PPA-PK6 |
|---|---|---|---|---|
| 5 hours | 336.8 | 553.1 | 291.5 | 186.7 |
| 16 hours | 879.5 | 1702.4 | 1172.5 | 873.1 |
| 20 hours | 1091.2 | 2031.2 | 1711.5 | 1204.3 |
| 24 hours | 1324.0 | 2378.4 | 2222.7 | 1628.0 |

TABLE 26

Excess $K_3PO_4$ Concentration and pH of Four PPA-HCl Transdermal Systems

|  | PPA-PK1R | PPA-PK2R | PPA-PK5 | PPA-PK6 |
|---|---|---|---|---|
| Excess $K_3PO_4$ Concentration |  | 0.2% | 6.2% | 16.4% |
| pH | 7 | 9.72 | 10.17 | 10.44 |

The cumulative amount of PPA-HCl that permeated across the human cadaver skin at 24 hours for PPA-PK2R (2378.4 $\mu g/cm^2$, Table 25) with a calculated excess $K_3PO_4$ concentration of 0.2% was about two times higher than that from the formulation without $K_3PO_4$ (PPA-PK1R, 1324.0 $\mu g/cm^2$). This result indicated that the permeation of PPA-HCl is enhanced with an excess $K_3PO_4$ concentration as low as 0.2%.

The cumulative amount of PPA-HCl across human cadaver skin at 24 hours remained about the same when the excess $K_3PO_4$ concentration in the dried patch was increased from 0.2% to 6.2% (Tables 25 and 26). When the excess $K_3PO_4$ concentration in the dried patch was further increased from 6.2% to 16.4% (Table 26), the cumulative amount of PPA-HCl across human cadaver skin at 24 hours decreased from 2222.7 to 1628.0 $\mu g/cm^2$. This decrease in flux may be because the high concentration of $K_3PO_4$ made the adhesive matrix more hydrophobic and the amount of $K_3PO_4$ that could be dissolved by the small amount of water on the top of the skin was reduced.

The pH of the PPA-HCl patch measured using the procedures listed above increased from 7 to 9.72 when the $K_3PO_4$ concentration in the dried patch was increased from 0% to 23% (or 0.2% excess $K_3PO4$ concentration, Tables 24 and 26). The pH of the PPA-HCl patch increased from 9.72 to 10.44 when the excess $K_3PO_4$ concentration in the dried patch was further increased from 0.2% to 16.4% (Table 26).

EXAMPLE 9

Figure 8:
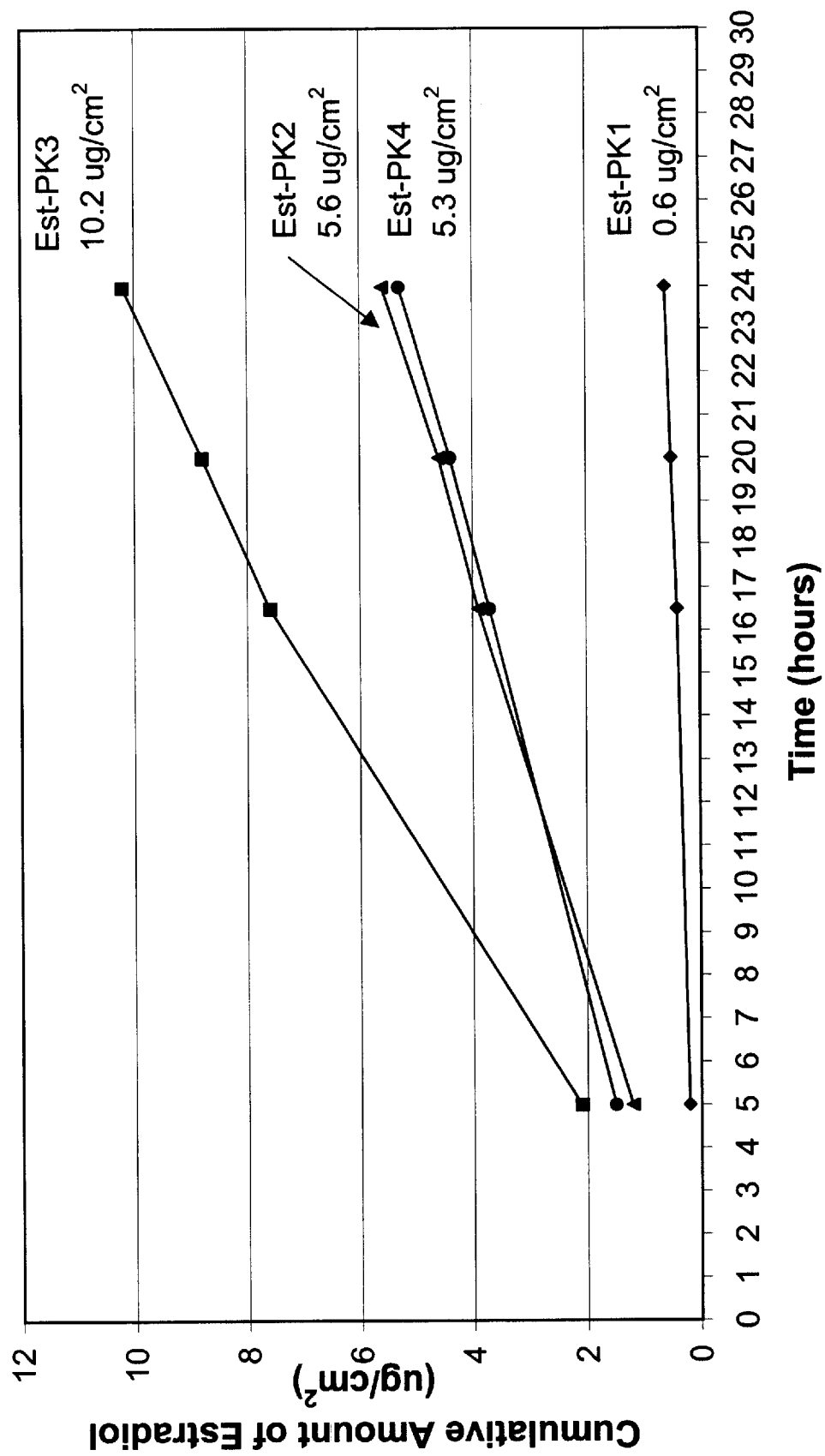
FIG. 8 is a graph illustrating the cumulative amount of estradiol from a matrix patch as described in Example 9.

An in vitro skin permeation study was conducted using four estradiol transdermal systems. The formulations used to prepare these systems are listed in Table 27, which includes weight and weight percent of each component in the formulations. The weight of potassium phosphate, tribasic ($K_3PO_4$) was 0 g, 0.1 g, 0.3 g, and 0.48 g for formulation #Est-PK1, -PK2, -PK3, and -PK4 respectively. The matrix patches were prepared and evaluated using the same procedures as set forth in Example 1. The theoretical percent weight for each ingredient after drying (calculated assuming all the volatile ingredients were completely removed during drying) is listed in Table 28. The cumulative amount of estradiol across human cadaver skin was calculated using the measured estradiol concentrations in the receiver solutions, which were shown in Table 29 and FIG. 8.

Since estradiol is not expected to react with $K_3PO_4$, the $K_3PO_4$ concentration listed in Table 28 equals the excess $K_3PO_4$ concentration.

The pH of each patch was determined using the procedure of Example 1 and the results are listed in Table 30.

TABLE 27

Weight and Weight Percent of Each Component (Based on Total Solution Weight) for Four Estradiol Transdermal Systems

|  | Est-PK1 | Est-PK2 | Est-PK3 | Est-PK4 |
|---|---|---|---|---|
| Estradiol | 0.03 g (0.5%) | 0.03 g (0.5%) | 0.03 g (0.5%) | 0.03 g (0.4%) |
| Methyl alcohol | 0.5 g (8.0%) | 0.5 g (7.8%) | 0.5 g (7.6%) | 0.5 g (7.4%) |
| $K_3PO_4$ | 0 | 0.1 g (1.6%) | 0.3 g (4.6%) | 0.48 g (7.1%) |
| DI water | 0.5 g (8.0%) | 0.5 g (7.8%) | 0.5 g (7.6%) | 0.5 g (7.4%) |
| Propylene glycol | 0.25 g (4.0%) | 0.25 g (3.9%) | 0.25 g (3.8%) | 0.25 g (3.7%) |
| PIB adhesive (30% solid) | 4 g (63.7%) | 4 g (62.7%) | 4 g (60.8%) | 4 g (59.2%) |
| Heptane | 1 g (15.9%) | 1 g (15.7%) | 1 g (15.2%) | 1 g (14.8%) |

TABLE 28

Weight and Theoretical Weight Percent of Each Component in the Dried Film for Four Estradiol Transdermal Systems

|  | Est-PK1 | Est-PK2 | Est-PK3 | Est-PK4 |
|---|---|---|---|---|
| Estradiol | 0.03 g (2.0%) | 0.03 g (1.9%) | 0.03 g (1.7%) | 0.03 g (1.5%) |
| K3PO4 | 0 | 0.1 g (6.3%) | 0.3 g (16.9%) | 0.48 g (24.5%) |
| Propylene glycol | 0.25 g (16.9%) | 0.25 g (15.8%) | 0.25 g (14.0%) | 0.25 g (12.8%) |
| PIB adhesive | 1.2 g (81.1%) | 1.2 g (76.0%) | 1.2 g (67.4%) | 1.2 g (61.2%) |

TABLE 29

Cumulative Amount of Estradiol across human cadaver skin for Estradiol Transdermal Systems ($\mu g/cm^2$)

|  | Est-PK1 | Est-PK2 | Est-PK3 | Est-PK4 |
|---|---|---|---|---|
| 5 hours | 0.2 | 1.2 | 2.1 | 1.5 |
| 16.5 hours | 0.4 | 3.9 | 7.6 | 3.7 |
| 20 hours | 0.5 | 4.6 | 8.8 | 4.4 |
| 24 hours | 0.6 | 5.6 | 10.2 | 5.3 |

TABLE 30

Excess $K_3PO_4$ Concentration and pH of Four Estradiol Transdermal Systems

|  | Est-PK1 | Est-PK2 | Est-PK3 | Est-PK4 |
|---|---|---|---|---|
| Excess $K_3PO_4$ Concentration | 0% | 6.3% | 16.9% | 24.5% |
| pH | 6.4 | 8.89 | 10.83 | 9.87 |

The cumulative amount of estradiol that permeated across the human cadaver skin at 24 hours for Est-PK2 (5.6 $\mu g/cm^2$, Table 9) with a calculated excess $K_3PO_4$ concentration of 6.3% was about nine times higher than that from the formulation without $K_3PO_4$ (Est-PK 1, 0.6 $\mu g/cm^2$). This result indicated that the permeation of estradiol is enhanced by $K_3PO_4$. The cumulative amount of estradiol across human cadaver skin at 24 hours increased from 5.6 to 10.2 when the excess $K_3PO_4$ concentration in the dried patch was increased from 6.3% to 16.9% (Tables 29 and 30). When the excess $K_3PO_4$ concentration in the dried patch was further increased from 16.9% to 24.5% (Table 30), the cumulative amount of estradiol across human cadaver skin at 24 hours decreased from 10.2 to 5.3 µg/cm². This decrease in flux may be because the high concentration of $K_3PO_4$ made the adhesive matrix more hydrophobic and the amount of $K_3PO_4$ that could be dissolved by the small amount of water on the top of the skin was reduced.

The pH of the estradiol patch measured using the procedures listed above increased from 6.4 to 10.83 when the $K_3PO_4$ concentration in the dried patch was increased from 0% to 16.9%. However, the pH of the estradiol patch decreased from 10.83 to 9.87 when the $K_3PO_4$ concentration in the dried patch was further increased from 16.9% to 24.5%.

EXAMPLE 10

Figure 9:
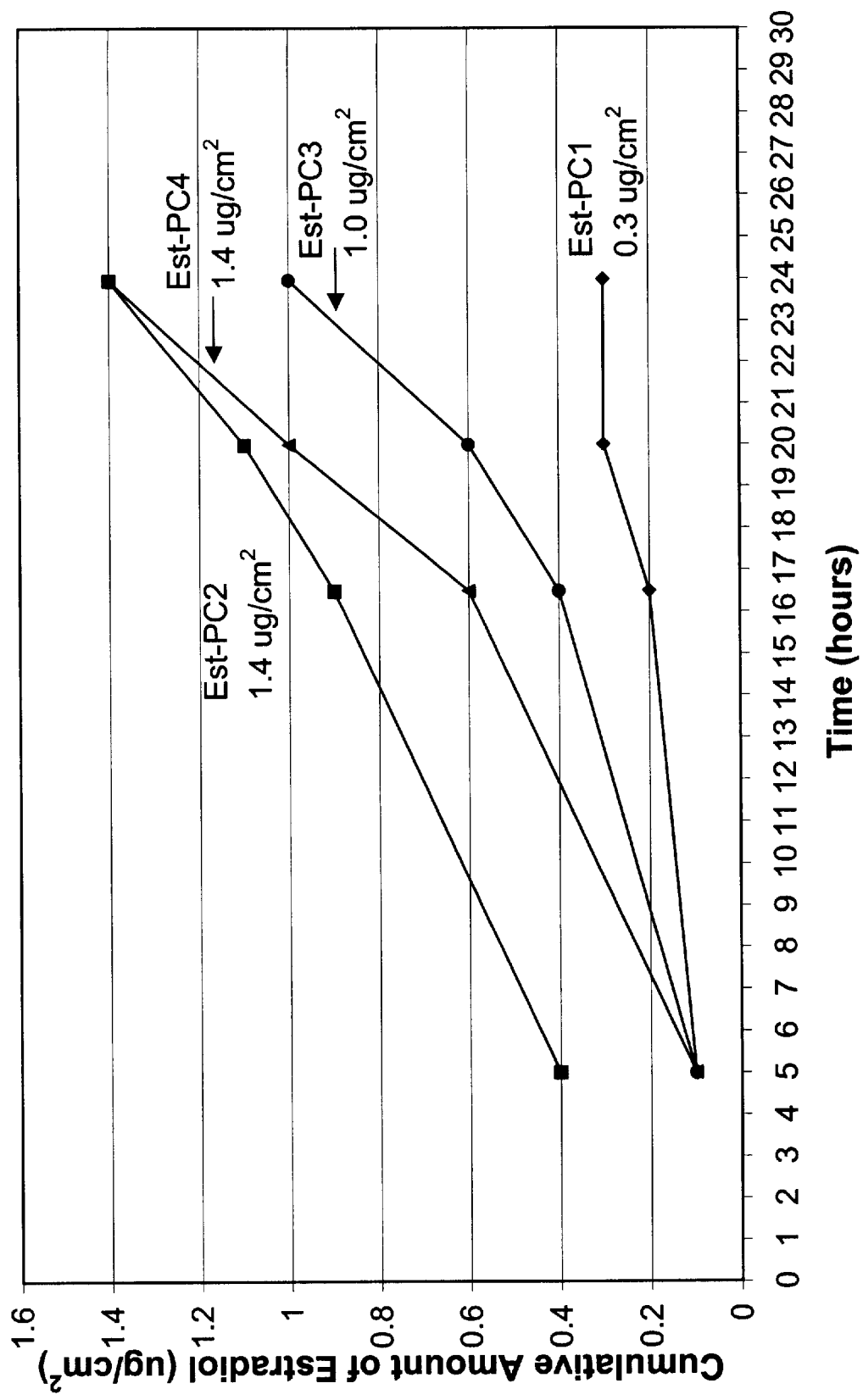
FIG. 9 is a graph illustrating the cumulative amount of estradiol from a matrix patch as described in Example 10.
Figure 10:
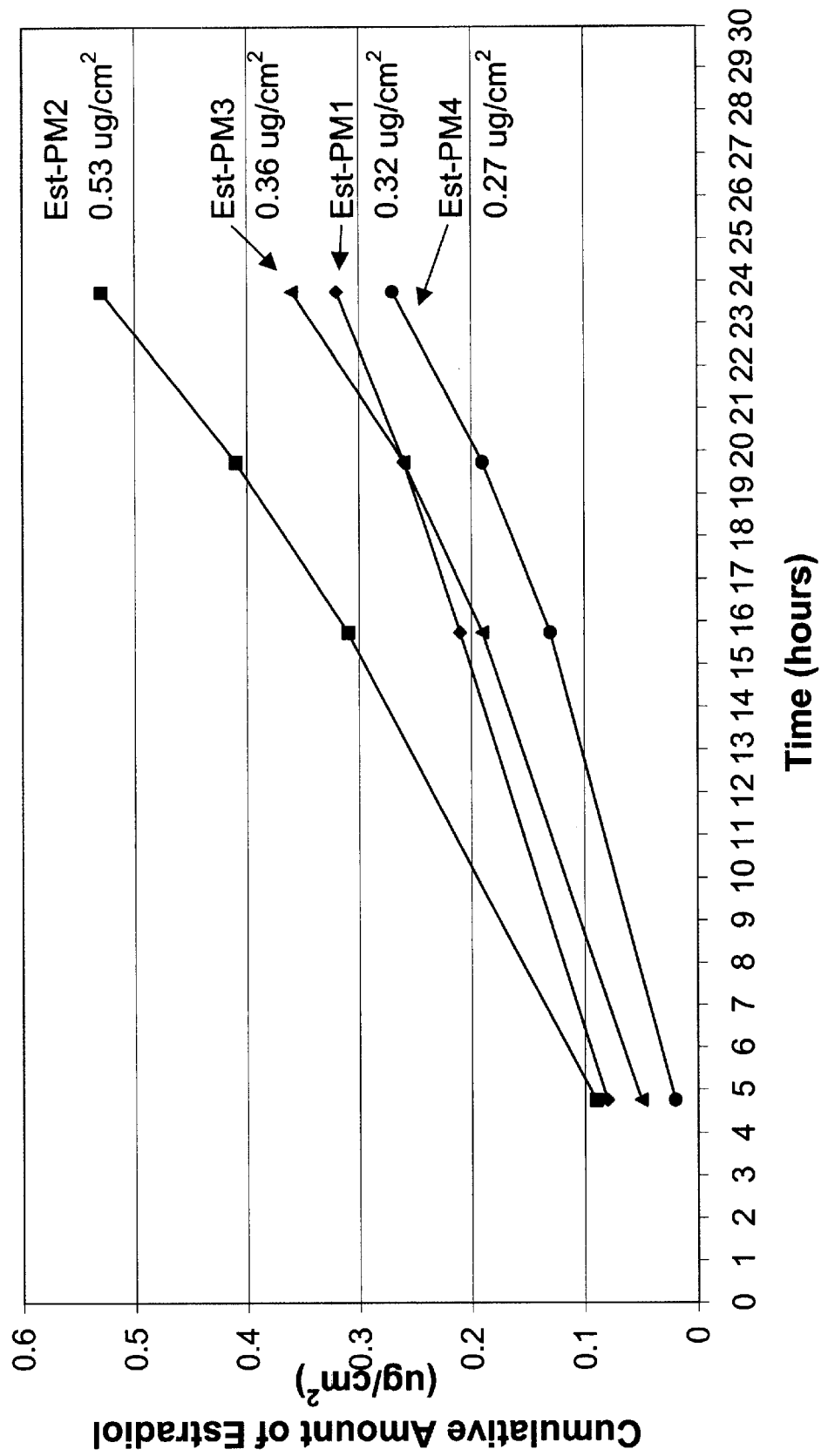
FIG. 10 is a graph illustrating the cumulative amount of estradiol from a matrix patch as described in Example 11.

An in vitro skin permeation study was conducted using four estradiol transdermal systems. The formulations used to prepare these systems are listed in Table 31, which includes weight and weight percent of each component in the formulations. The weight of sodium carbonate ($Na_2CO_3$) was 0 g, 0.11 g, 0.3 g, and 0.45 g for formulation #Est-PC1, -PC2, -PC3, and -PC4 respectively. The matrix patches were prepared and evaluated using the same procedures as set forth in Example 1. The theoretical percent weight for each ingredient after drying (calculated assuming all the volatile ingredients were completely removed during drying) is listed in Table 32. The cumulative amount of estradiol across human cadaver skin was calculated using the measured estradiol concentrations in the receiver solutions, which were shown in Table 33 and FIG. 9.

Since estradiol is not expected to react with $Na_2CO_3$, the $Na_2CO_3$ concentration listed in Table 32 equals the excess $Na_2CO_3$ concentration.

The pH of each patch was determined using the procedure of Example 1 and the results are listed in Table 34.

TABLE 31

Weight and Weight Percent of Each Component (Based on Total Solution Weight) for Four Estradiol Transdermal Systems

|  | Est-PC1 | Est-PC2 | Est-PC3 | Est-PC4 |
| --- | --- | --- | --- | --- |
| Estradiol | 0.03 g | 0.03 g | 0.03 g | 0.03 g |
|  | (0.5%) | (0.4%) | (0.4%) | (0.4%) |
| $Na_2CO_3$ | 0 | 0.11 g | 0.3 g | 0.45 g |
|  |  | (1.6%) | (4.1%) | (6.1%) |
| DI water | 0.5 g | 1.2 g | 1.2 g | 1.2 g |
|  | (8.0%) | (16.9%) | (16.5%) | (16.2%) |
| Methyl alcohol | 0.5 g | 0.5 g | 0.5 g | 0.5 g |
|  | (8.0%) | (7.1%) | (6.9%) | (6.7%) |
| PIB adhesive (30% solid) | 4 g | 4 g | 4 g | 4 g |
|  | (63.7%) | (56.4%) | (55.0%) | (53.8%) |
| Propylene glycol | 0.25 g | 0.25 g | 0.25 g | 0.25 g |
|  | (4.0%) | (3.5%) | (3.4%) | (3.4%) |
| Heptane | 1 g | 1 g | 1 g | 1 g |
|  | (15.9%) | (14.1%) | (13.7%) | (13.5%) |

TABLE 32

Weight and Theoretical Weight Percent of Each Component in the Dried Film for Four Estradiol Transdermal Systems

|  | Est-PC1 | Est-PC2 | Est-PC3 | Est-PC4 |
| --- | --- | --- | --- | --- |
| Estradiol | 0.03 g | 0.03 g | 0.03 g | 0.03 g |
|  | (2.0%) | (1.9%) | (1.7%) | (1.6%) |
| $Na_2CO_3$ | 0 | 0.11 g | 0.3 g | 0.45 g |
|  |  | (6.9%) | (16.9%) | (23.3%) |
| PIB adhesive | 1.2 g | 1.2 g | 1.2 g | 1.2 g |
|  | (81.1%) | (75.5%) | (67.4%) | (62.2%) |
| Propylene glycol | 0.25 g | 0.25 g | 0.25 g | 0.25 g |
|  | (16.9%) | (15.7%) | (14.0%) | (13.0%) |

TABLE 33

Cumulative Amount of Estradiol Across Human Cadaver Skin for Estradiol Transdermal Systems (µg/cm²)

|  | Est-PC1 | Est-PC2 | Est-PC3 | Est-PC4 |
| --- | --- | --- | --- | --- |
| 5 hours | 0.1 | 0.4 | 0.1 | 0.1 |
| 16.5 hours | 0.2 | 0.9 | 0.4 | 0.6 |
| 20 hours | 0.3 | 1.1 | 0.6 | 1.0 |
| 24 hours | 0.3 | 1.4 | 1.0 | 1.4 |

TABLE 34

Excess $Na_2CO_3$ Concentration and pH of Four Estradiol Transdermal Systems

|  | Est-PC1 | Est-PC2 | Est-PC3 | Est-PC4 |
| --- | --- | --- | --- | --- |
| Excess $Na_2CO_3$ Concentration | 0% | 6.9% | 16.9% | 23.3% |
| pH | 7.48 | 9.87 | 10.51 | 10.49 |

The cumulative amount of estradiol that permeated across the human cadaver skin at 24 hours for Est-PC2 (1.4 µg/cm², Table 33) with a calculated excess $Na_2CO_3$ concentration of 6.9% was about four times higher than that from the formulation without $Na_2CO_3$ (Est-PC1, 0.3 µg/cm²). This result indicated that $Na_2CO_3$ could enhance the permeation of estradiol.

The cumulative amount of estradiol across human cadaver skin at 24 hours remained about the same when the excess $Na_2CO_3$ concentration in the dried patch was increased from 6.9% to 23.3% (Tables 33 and 34). This behavior may be because the amount of $Na_2CO_3$ that could be dissolved by the small amount of water on the top of the skin remained about the same for Est-PC2, Est-PC3 and Est-PC4.

The pH of the estradiol patch measured using the procedures listed above increased from 7.48 to 10.51 when the $Na_2CO_3$ concentration in the dried patch was increased from 0% to 16.9%. However, when the $Na_2CO_3$ concentration in the dried patch was further increased from 16.9% to 23.3%, the pH of the estradiol patch remained about the same.

EXAMPLE 11

Figure 11:
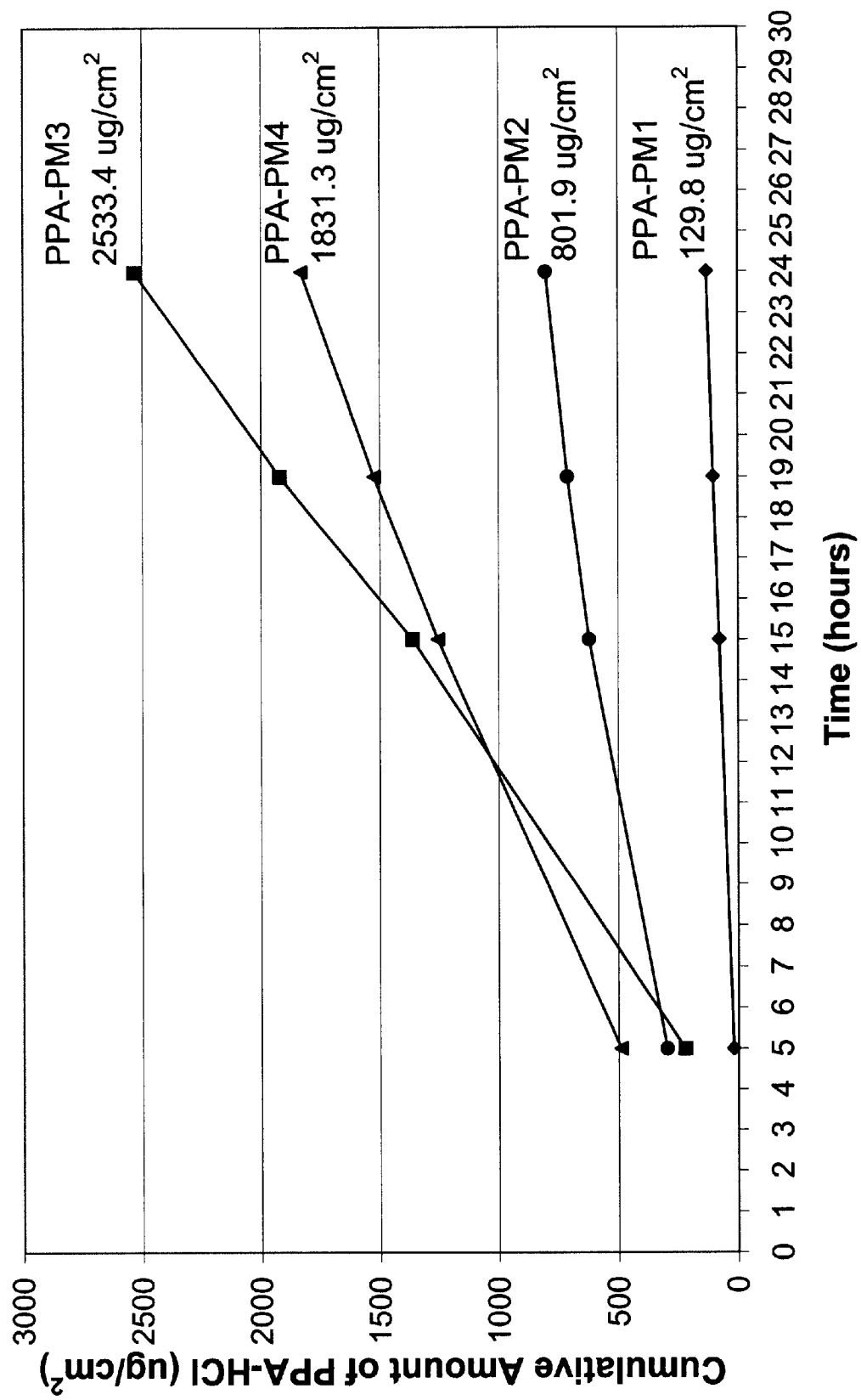
FIG. 11 is a graph illustrating the cumulative amount of phenylpropanolamine from a matrix patch as described in Example 12.

An in vitro skin permeation study was conducted using four estradiol transdermal systems. The formulations used to prepare these systems are listed in Table 35, which includes weight and weight percent of each component in the formulations. The weight of magnesium oxide (MgO) was 0 g, 0.11 g, 0.3 g and 0.45 g for formulation #Est-PM1, -PM2,-PM3 and -PM4 respectively. The matrix patches were prepared and evaluated using the same procedures as set forth in Example 1. The theoretical percent weight for each ingredient after drying (calculated assuming all the volatile ingredients were completely removed during drying) is listed in Table 36. The cumulative amount of estradiol across human cadaver skin was calculated using the measured estradiol concentrations in the receiver solutions, which were shown in Table 37 and FIG. 11.

Since estradiol is not expected to react with MgO, the MgO concentration listed in Table 36 equals the excess MgO concentration.

The pH of each patch was determined using the procedure of Example 1 and the results are listed in Table 38.

TABLE 35

Weight and Weight Percent of Each Component (Based on Total Solution Weight) for Four Estradiol Transdermal Systems

|  | Est-PM1 | Est-PM2 | Est-PM3 | Est-PM4 |
| --- | --- | --- | --- | --- |
| Estradiol | 0.03 g (0.5%) | 0.03 g (0.4%) | 0.03 g (0.4%) | 0.03 g (0.4%) |
| MgO | 0 | 0.11 g (1.6%) | 0.3 g (4.1%) | 0.45 g (6.1%) |
| DI water | 0.5 g (8.0%) | 1.2 g (16.9%) | 1.2 g (16.5%) | 1.2 g (16.2%) |
| Methyl alcohol | 0.5 g (8.0%) | 0.5 g (7.1%) | 0.5 g (6.9%) | 0.5 g (6.7%) |
| PIB adhesive (30% solid) | 4 g (63.7%) | 4 g (56.4%) | 4 g (55.0%) | 4 g (53.8%) |
| Propylene glycol | 0.25 g (4.0%) | 0.25 g (3.5%) | 0.25 g (3.4%) | 0.25 g (3.4%) |
| Heptane | 1 g (15.9%) | 1 g (14.1%) | 1 g (13.7%) | 1 g (13.5%) |

TABLE 36

Weight and Theoretical Weight Percent of Each Component in the Dried Film for Four Estradiol Transdermal Systems

|  | Est-PM1 | Est-PM2 | Est-PM3 | Est-PM4 |
| --- | --- | --- | --- | --- |
| Estradiol | 0.03 g (2.0%) | 0.03 g (1.9%) | 0.03 g (1.7%) | 0.03 g (1.6%) |
| MgO | 0 | 0.11 g (6.9%) | 0.3 g (16.9%) | 0.45 g (23.3%) |
| PIB adhesive | 1.2 g (81.1%) | 1.2 g (75.5%) | 1.2 g (67.4%) | 1.2 g (62.2%) |
| Propylene glycol | 0.25 g (16.9%) | 0.25 g (15.7%) | 0.25 g (14.0%) | 0.25 g (13.0%) |

TABLE 37

Cumulative Amount of Estradiol Across Human Cadaver Skin for Estradiol Transdermal Systems ($\mu g/cm^2$)

|  | Est-PM1 | Est-PM2 | Est-PM3 | Est-PM4 |
| --- | --- | --- | --- | --- |
| 4.75 hours | 0.08 | 0.09 | 0.05 | 0.02 |
| 15.75 hours | 0.21 | 0.31 | 0.19 | 0.13 |
| 19.75 hours | 0.26 | 0.41 | 0.26 | 0.19 |
| 23.75 hours | 0.32 | 0.53 | 0.36 | 0.27 |

TABLE 38

Excess MgO Concentration and pH of Four Estradiol Transdermal Systems

|  | Est-PM1 | Est-PM2 | Est-PM3 | Est-PM4 |
| --- | --- | --- | --- | --- |
| Excess MgO Concentration | 0% | 6.9% | 16.9% | 23.3% |
| pH | 7.48 | 8.95 | 9.66 | 10.28 |

The cumulative amount of estradiol that permeated across the human cadaver skin at 24 hours for Est-PM2 (0.53 $\mu g/cm^2$, Table 37) with a calculated excess MgO concentration of 6.9% was slightly higher than that from the formulation without $K_3PO_4$ (Est-PM1, 0.32 $\mu g/cm^2$). This result indicated that MgO enhances the permeation of estradiol.

The cumulative amount of estradiol across human cadaver skin at 24 hours decreased from 0.53 to 0.27 $\mu g/cm^2$ when the excess MgO concentration in the dried patch was increased from 6.9% to 23.3% (Tables 23 and 24). This behavior may be because the high concentration of MgO made the adhesive matrix more hydrophobic and the amount of MgO that could be dissolved by the small amount of water on the top of the skin was reduced.

The pH of the estradiol patch measured using the procedures listed above increased from 7.48 to 10.28 when the MgO concentration in the dried patch was increased from 0% to 23.3%.

EXAMPLE 12

An in vitro skin permeation study was conducted using four phenylpropanolamine hydrochloride (PPA-HCl) transdermal systems. The formulations used to prepare these systems are listed in Table 39, which includes weight and weight percent of each component in the formulations. The weight of magnesium oxide (MgO) was 0 g, 0.11 g, 0.26 g and 0.50 g for formulation #PPA-PM1, -PM2, -PM3, and -PM4 respectively. The matrix patches were prepared and evaluated using the same procedures as set forth in Example 3. The theoretical percent weight for each ingredient after drying (calculated assuming all the volatile ingredients were completely removed during drying) is listed in Table 40. The cumulative amount of PPA-HCl across human cadaver skin was calculated using the measured PPA-HCl concentrations in the receiver solutions, which were shown in Table 41 and FIG. 11.

Since PPA-HCl is a salt of a free base, it reacts with MgO. The concentration of MgO in the system after the reaction is completed depends on the amount of PPA-HCl added. The remaining MgO concentration after the reaction is completed is defined as "excess MgO concentration," which is calculated by the following equation.

$$[MgO_{excess}] = [MgO_{total}] - [MgO_{needed\ for\ neutralization}]$$

The excess MgO concentration for four PPA-HCl systems, #PPA-PM1, -PM2, -PM3 and -PM4 were calculated and listed in Table 42.

The pH of the patch was determined using the procedure of Example 1 and the results are listed in Table 42.

TABLE 39

Weight and Weight Percent of Each Component (Based on Total Solution Weight) for Four PPA-HCl Transdermal Systems

|  | PPA-PM1 | PPA-PM2 | PPA-PM3 | PPA-PM4 |
| --- | --- | --- | --- | --- |
| PPA-HCl | 0.5 g (6.9%) | 0.5 g (6.0%) | 0.5 g (5.9%) | 0.5 g (5.7%) |
| MgO | 0 | 0.11 g (1.3%) | 0.26 g (3.1%) | 0.50 g (5.7%) |
| DI water | 1.0 g (13.9%) | 2.0 g (24.0%) | 2.0 g (23.6%) | 2.0 g (22.9%) |
| Methyl alcohol | 0.5 g (6.9%) | 0.5 g (6.0%) | 0.5 g (5.9%) | 0.5 g (5.7%) |
| Propylene glycol | 0.2 g (2.8%) | 0.2 g (2.4%) | 0.2 g (2.4%) | 0.2 g (2.3%) |

TABLE 39-continued

Weight and Weight Percent of Each Component (Based on Total Solution Weight) for Four PPA-HCl Transdermal Systems

|  | PPA-PM1 | PPA-PM2 | PPA-PM3 | PPA-PM4 |
| --- | --- | --- | --- | --- |
| HPMC | 0.02 g (0.3%) | 0.02 g (0.2%) | 0.02 g (0.2%) | 0.02 g (0.2%) |
| PIB adhesive (30% solid) | 14 g (55.4%) | 4 g (48.0%) | 4 g (47.2%) | 4 g (45.9%) |
| Heptane | 1.0 g (13.9%) | 1.0 g (12.0%) | 1.0 g (11.8%) | 1.0 g (11.5%) |

TABLE 40

Weight and Theoretical Weight Percent of Each Component in the Dried Film for Four PPA-HCl Transdermal Systems

|  | PPA-PM1 | PPA-PM2 | PPA-PM3 | PPA-PM4 |
| --- | --- | --- | --- | --- |
| PPA-HCl | 0.5 g (26.0%) | 0.5 g (24.6%) | 0.5 g (22.9%) | 0.5 g (20.7%) |
| MgO | 0 | 0.11 g (5.4%) | 0.26 g (11.9%) | 0.50 g (20.7%) |
| Propylene glycol | 0.2 g (10.4%) | 0.2 g (9.9%) | 0.2 g (9.2%) | 0.2 g (8.3%) |
| HPMC | 0.02 g (1.0%) | 0.02 g (1.0%) | 0.02 g (0.9%) | 0.02 g (0.8%) |
| PIB adhesive | 1.2 g (62.5%) | 1.2 g (59.1%) | 1.2 g (55.0%) | 1.2 g (49.6%) |

TABLE 41

Cumulative Amount of PPA-HCl Across Human Cadaver Skin for PPA-HCl Transdermal Systems ($\mu g/cm^2$)

|  | PPA-PM1 | PPA-PM2 | PPA-PM3 | PPA-PM4 |
| --- | --- | --- | --- | --- |
| 5 hours | 18.7 | 296.8 | 222.1 | 489.4 |
| 15 hours | 77.8 | 621.5 | 1362.9 | 1255.2 |
| 19 hours | 102.7 | 711.4 | 1920.9 | 1524.9 |
| 24 hours | 129.8 | 801.9 | 2533.4 | 1831.3 |

TABLE 42

Excess MgO Concentration and pH of Four PPA-HCl Transdermal Systems

|  | PPA-PM1 | PPA-PM2 | PPA-PM3 | PPA-PM4 |
| --- | --- | --- | --- | --- |
| Excess MgO Concentration |  | 0.1% | 7.0% | 16.2% |
| pH | 7.89 | 9.60 | 10.09 | 10.10 |

The cumulative amount of PPA-HCl that permeated across the human cadaver skin at 24 hours for PPA-PM2 (801.9 $\mu g/cm^2$, Table 41) with a calculated excess MgO concentration of 0.1% was about six times higher than that from the formulation without MgO (PPA-PM1, 129.8 $\mu g/cm^2$). This result indicated that the permeation of PPA-HCl is enhanced with an excess MgO concentration as low as 0.1%.

The cumulative amount of PPA-HCl across human cadaver skin at 24 hours increased from 801.9 to 2533.4 $\mu g/cm^2$ when the excess MgO concentration in the dried patch was increased from 0.1% to 7.0% (Tables 41 and 42). When the excess MgO concentration in the dried patch was further increased from 7.0% to 16.2% (Table 42), the cumulative amount of PPA-HCl across human cadaver skin at 24 hours decreased from 2533.4 to 1831.3 $\mu g/cm^2$. This decrease in flux may be because the high concentration of MgO made the adhesive matrix more hydrophobic and the amount of MgO that could be dissolved by the small amount of water on the top of the skin was reduced.

The pH of the PPA-HCl patch measured using the procedures listed above increased from 7.89 to 9.60 when the MgO concentration in the dried patch was increased from 0% to 5.4% (or 0.1% excess MgO concentration, Tables 40 and 42). The pH of the PPA-HCl remained about the same when the excess MgO concentration in the dried patch was further increased from 0.1% to 16.2% (Table 42).

EXAMPLE 13

An in vitro skin permeation study was conducted using three leuprolide solutions. The formulations used to prepare these systems are listed in Table 43, which include weight and weight percent of each ingredient in the formulations. The weight of sodium hydroxide was 0 g, 0.0125 g, and 0.0275 g for formulation #Leu-S1, #Leu-S2 and #Leu-S3, respectively. Each formulation was stirred until the solution was uniform.

The in-vitro permeation of each leuprolide solution through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The skin was clamped between the donor and receiver chambers of the diffusion cell, and the stratum corneum was allowed to dry. The leuprolide solution was applied to the stratum corneum using a micro-pipette. Each formulation was applied in a 25 $\mu l$ dosage and a 50 $\mu l$ dosage for a total of 6 test groups. The receiver chamber was sealed to the atmosphere using para-film wrap so that it was spill-proof and airtight. Three diffusion cells were used for each test group for a total of 18 cells.

The cells were filled with deionized (DI) water for a receiver solution. The DI water had been degased to remove air bubbles. The receiver solution was completely withdrawn and replaced with fresh DI water at each time point. Samples of the receiver solution were taken and analyzed by HPLC (high pressure liquid chromatography) to determine the leuprolide concentration. The cumulative amount of leuprolide across human cadaver skin (Table 44) was calculated using the measured leuprolide concentrations in the receiver solutions for each time point.

TABLE 43

Weight and Weight Percent of Components (Based on Total Solution Weight) for Three Leuprolide Transdermal Systems

|  | Leu-S1 | Leu-S2* | Leu-S3* |
| --- | --- | --- | --- |
| Leuprolide | 0.003 g (0.4%) | $6.4 \times 10^{-4}$ g (0.18%) | $6.4 \times 10^{-4}$ g (0.16%) |
| DI water | 0.45 g (64.0%) | 0.28 g (80.9%) | 0.33 g (80.3%) |
| NaOH | 0 g (0.0%) | 0.0125 g (3.6%) | 0.0275 g (6.7%) |
| Propylene Glycol | 0.25 g (35.6%) | 0.053 g (15.3%) | 0.053 g (13.0%) |

*Solutions Leu:S2 and Leu-3 were prepared using 0.15 g of Leu-S1, then adding the correct amount of NaOH and DI water. Percentages may not add up to 100% due to rounding.

TABLE 44

Cumulative Amount of Leuprolide Permeated Across Human Cadaver Skin From a 25 µl and a 50 µl Solution Containing NaOH at 5-hour and 24-hour Time Points ($\mu g/cm^2$)

| | Leu-S1<br>25 µl | Leu-S2<br>25 µl | Leu-S3<br>25 µl | Leu-S1<br>50 µl | Leu-S2<br>50 µl | Leu-S3<br>50 µl |
|---|---|---|---|---|---|---|
| 5 hours | 0.38 | 0.52 | 0.58 | 0.32 | 0.62 | 0.3 |
| 24 hours | 0.52 | 3.21 | 4.43 | 0.32 | 8.58 | 10.8 |

The cumulative amount of leuprolide across human cadaver skin for the 25 µl dosage at 24 hours increased from 0.52 $\mu g/cm^2$ to 4.43 $\mu g/cm^2$ when the calculated sodium hydroxide concentration in the dried patch was increased from 0% to 6.7%. The cumulative amount of leuprolide across human cadaver skin for the 50 µl dosage at 24 hours increased from 0.32 $\mu g/cm^2$ to 10.8 $\mu g/cm^2$ when the calculated sodium hydroxide concentration in the leuprolide solution was increased from 0% to 6.7%. The cumulative amount of leuprolide across human cadaver skin at 24 hours from the 50 µl dosage group containing 3.6% NaOH (Leu-S2) was 8.58 $\mu g/cm^2$, which was about 27 times higher than that from the formulation without NaOH (0.32 $\mu g/cm^2$, #Leu-S1).

EXAMPLE 14

The in-vitro permeation of oxytocin through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The skin was clamped between the donor and receiver chambers of the diffusion cell. Eighteen diffusion cells were used in this study. A 2% NaOH aqueous solution (50 µl) was introduced to the donor chambers of nine cells (cells #1 to 9) and a 4% NaOH aqueous solution (50 µl) was introduced to the donor chambers of the other nine cells (cells #10 to 18). Once the NaOH solution is applied, the donor chamber was covered with parafilm.

After 5 hours, the NaOH solution was washed away from the skin for 3 cells (cells #1 to 3) that were treated with 2% NaOH solution and 3 cells (cells #10 to 12) that were treated with 4% NaOH solution. After 10 hours, the NaOH solution was washed away from the skin for 3 cells (cells #4 to 6) that were treated with 2% NaOH solution and 3 cells (cells #13 to 15) that were treated with 4% NaOH solution. After 24 hours, the NaOH solution was washed away from the skin for 3 cells (cells #7 to 9) that were treated with 2% NaOH solution and 3 cells (cells #16 to 18) that were treated with 4% NaOH solution. To wash away the NaOH solution, the receiving fluid was removed and replaced with fresh DI water. This was done twice. DI water was added to the donor chamber to dilute the NaOH solution and then the donor solution was removed. This was repeated several times.

After the NaOH solution was washed away from the skin, the solution in the donor chamber was completely removed and replaced by 50 µl of an oxytocin solution. The formulation of the oxytocin solution is listed in Table 45. Once the oxytocin solution is applied, the donor chamber was covered with parafilm.

The cells were filled with DI water as a receiver solution. The DI water had been degased to remove air bubbles. The receiver solution was completely withdrawn and replaced with fresh DI water at each time point. The samples taken were analyzed by HPLC for the concentration of oxytocin in the receiver solution. The cumulative amount of oxytocin across human cadaver skin was calculated using the measured oxytocin concentrations in the receiver solutions for each time point, which were listed in Table 46.

TABLE 45

Formulation for the Oxytocin Solution

| Oxytocin | 0.005 g |
|---|---|
| DI water | 0.6 g |
| Propylene Glycol | 0.6 g |

TABLE 46

Cumulative Amount of Oxytocin Permeated Across Human Cadaver Skin From an Oxytocin Solution ($\mu g/cm^2$)

| | Skin pretreated by 4% NaOH for 5 hr | Skin pretreated by 4% NaOH for 15 hr | Skin pretreated by 4% NaOH for 24 hr |
|---|---|---|---|
| 5 hours | 118.95 | 202.28 | 193.82 |
| 15 hours | 200.66 | 222.45 | 232.72 |
| 24 hours | 225.52 | 231.58 | 236.80 |

EXAMPLE 15

The in-vitro permeation of oxytocin through human cadaver skin was performed using Franz-type diffusion cells with a diffusion area of 1 $cm^2$. The volume of receiver solution was 8 ml. Human cadaver skin was cut to a proper size and placed on a flat surface with the stratum corneum side facing up. The skin was clamped between the donor and receiver chambers of the diffusion cell. Eighteen diffusion cells were used in this study. A 0.25% NaOH aqueous solution (50 µl) was introduced to the donor chambers of nine cells (cells #1 to 9) and A 1.0% NaOH aqueous solution (50 µl) was introduced to the donor chambers of the other nine cells (cells #10 to 18). Once the NaOH solution is applied, the donor chamber was covered with parafilm.

After 5 hours, the NaOH solution was washed away from the skin for 3 cells (cells #1 to 3) that were treated with 0.5% NaOH solution and 3 cells (cells #10 to 12) that were treated with 1.0% NaOH solution. After 11 hours, the NaOH solution was washed away from the skin for 3 cells (cells #4 to 6) that were treated with 0.25% NaOH solution and 3 cells (cells #13 to 15) that were treated with 1.0% NaOH solution. After 24 hours, the NaOH solution was washed away from the skin for 3 cells (cells #7 to 9) that were treated with 0.25% NaOH solution and 3 cells (cells #16 to 18) that were treated with 1.0% NaOH solution. To wash away the NaOH solution, the receiving fluid was removed and replaced with fresh DI water. This was done twice. DI water was added to the donor chamber to dilute the NaOH solution and then the donor solution was removed. This was repeated several times until the pH of donor solution was less than 8.

After the NaOH solution was washed away from the skin, the solution in the donor chamber was completely removed and replaced by 50 µl of an oxytocin solution. The formulation of the oxytocin solution is listed in Table 47. Once the oxytocin solution is applied, the donor chamber was covered with parafilm.

The cells were filled with DI water as a receiver solution. The DI water has been degased to remove air bubbles. The receiver solution was completely withdrawn and replaced with fresh DI water at each time point. The samples taken were analyzed by an HPLC for the concentration of oxytocin in the receiver solution. The cumulative amount of oxytocin across human cadaver skin was calculated using the measured oxytocin concentrations in the receiver solutions for each time point, which were listed in Table 48.

TABLE 47

Formulation for the Oxytocin Solution

| | |
|---|---|
| Oxytocin | 0.005 g |
| DI water | 0.6 g |
| Propylene Glycol | 0.6 g |

TABLE 48

Cumulative Amount of Oxytocin Permeated Across Human Cadaver Skin From an Oxytocin Solution ($\mu g/cm^2$)

| | Skin pretreated by 1.0% NaOH for 5 hr | Skin pretreated by 1.0% NaOH for 11 hr | Skin pretreated by 1.0% NaOH for 24 hr |
|---|---|---|---|
| 4.25 hours | 0.45 | 53.42 | 13.23 |
| 14.75 hours | 0.97 | 67.97 | 21.06 |
| 24 hours | 0.97 | 75.36 | 30.97 |

EXAMPLE 16

An in-vitro skin permeation study was conducted using four diclofenac sodium transdermal systems. The formulations used to prepare these systems are listed in Table 49, which include weight and weight percent of each ingredient in the formulations. The weight of sodium hydroxide (NaOH) was 0 g, 0.035 g, 0.05 g, and 0.1 g for formulation #Diclo-P10, -P11, -P12, and -P13 respectively. Each formulation was coated on a release liner and dried in an oven at 55EC for two hours to remove water and other solvents. The dried drug-in-adhesive/release liner film was laminated to a backing film. The backing/drug-in-adhesive/release liner laminate was then cut into round discs with a diameter of 11/16 inch. The theoretical percent weight for each ingredient after drying (calculated assuming all the volatile ingredients were completely removed during drying) is listed in Table 50.

The in-vitro permeation of diclofenac sodium through human cadaver skin from these discs was performed using Franz-type diffusion cells with a diffusion area of 1 $cm^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

Figure 12:
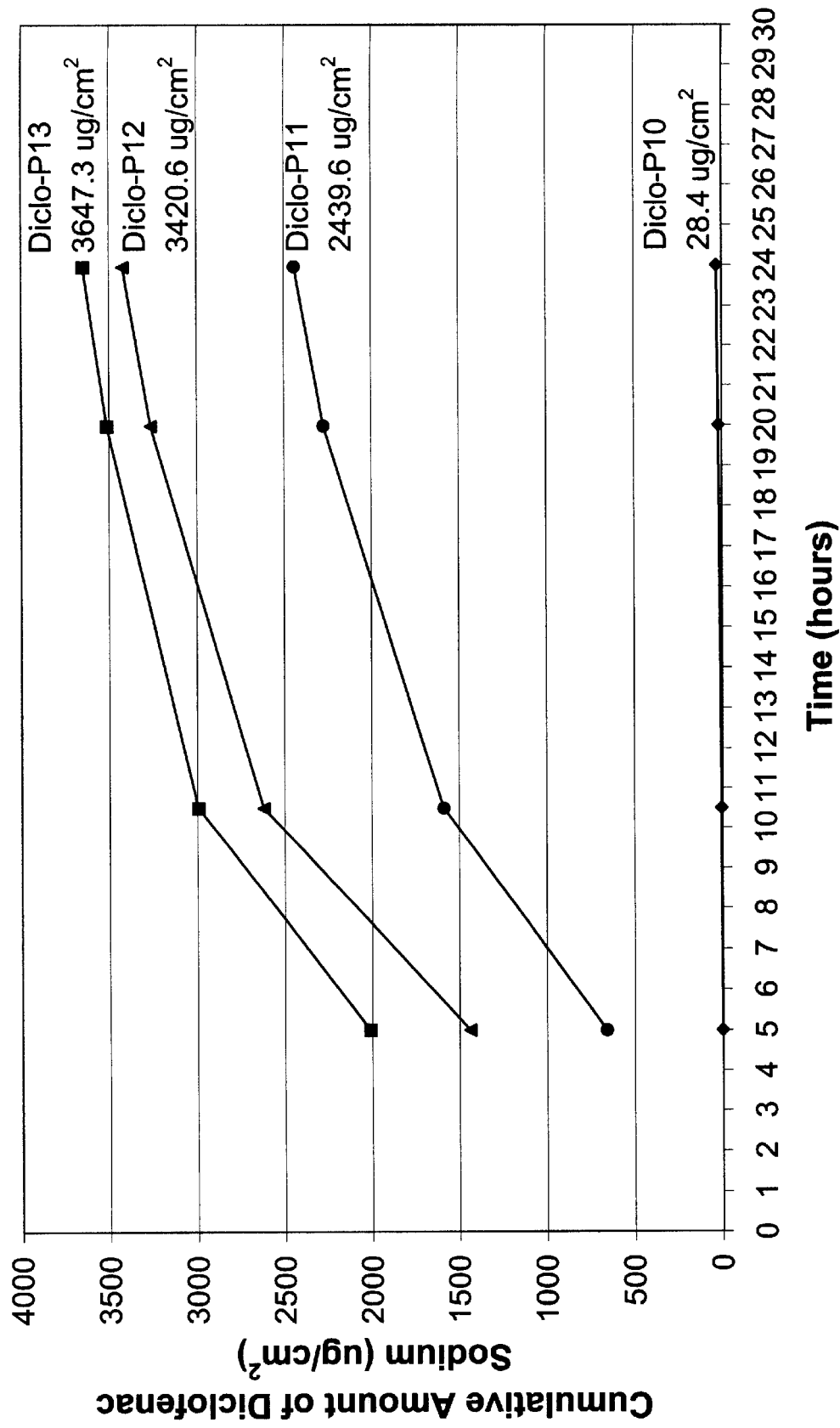
FIG. 12 is a graph illustrating the cumulative amount of diclofenac from a matrix patch as described in Example 16.

The cells were filled with 10% ethanol/90% water solution. The receiver solution was completely withdrawn and replaced with fresh ethanol/water solution at each time point. The samples taken were analyzed by an HPLC for the concentration of diclofenac sodium in the receiver solution. The cumulative amount of diclofenac sodium across human cadaver skin was calculated using the measured diclofenac sodium concentrations in the receiver solutions, which were shown in Table 51 and FIG. 12.

Since diclofenac sodium is not expected to react with NaOH, the NaOH concentration listed in Table 50 equals the excess NaOH concentration.

The pH of the patch was determined using the following procedures. A 2.5 $cm^2$ circular patch was punched out. Ten ml purified water was pipetted into a glass vial, and a stir bar was added, the liner was removed from patch and placed in the vial along with the patch. The vial was then placed on a stir plate and the water/patch/liner mixture was stirred for 5 minutes, at which point the liner was removed from the vial and discard. The vial was again placed on a stir plate and stirring continued for an additional 18 hours. After 18 hours, the stir bar was removed from vial and the pH of the solution determined using a calibrated pH meter.

The measured pHs for the diclofenac sodium transdermal systems are listed in Table 52.

TABLE 49

Weight and Weight Percent of Each Component (Based on Total Solution Weight) for Four Diclofenac Sodium Transdermal Systems

| | Diclo-P10 | Diclo-P11 | Diclo-P12 | Diclo-P13 |
|---|---|---|---|---|
| Diclofenac sodium | 0.6 g (9.2%) | 0.6 g (9.1%) | 0.6 g (9.0%) | 0.6 g (9.0%) |
| Propylene glycol | 0.9 g (13.9%) | 0.9 g (13.7%) | 0.9 g (13.6%) | 0.9 g (13.4%) |
| NaOH | 0 | 0.035 g (0.5%) | 0.05 g (0.8%) | 0.1 g (1.5%) |
| PIB adhesive (30% solid) | 4 g (61.5%) | 4 g (60.9%) | 4 g (60.6%) | 4 g (59.7%) |
| Heptane | 1 g (15.4%) | 1 g (15.2%) | 1 g (15.2%) | 1 g (14.9%) |
| DI water | 0 | 0.035 g (0.5%) | 0.05 g (0.8%) | 0.1 g (1.5%) |

TABLE 50

Weight and Theoretical Weight Percent of Component in the Dried Film for Four Diclofenac Sodium Transdermal Systems

| | Diclo-P10 | Diclo-P11 | Diclo-P12 | Diclo-P13 |
|---|---|---|---|---|
| Diclofenac sodium | 0.6 g (22.2%) | 0.6 g (21.9%) | 0.6 g (21.8%) | 0.6 g (21.4%) |
| Propylene glycol | 0.9 g (33.3%) | 0.9 g (32.9%) | 0.9 g (32.7%) | 0.9 g (32.1%) |
| NaOH | 0 | 0.035 g (1.3%) | 0.05 g (1.8%) | 0.1 g (3.6%) |
| PIB adhesive (30% solid) | 1.2 g (44.4%) | 1.2 g (43.9%) | 1.2 g (43.6%) | 1.2 g (42.9%) |

TABLE 51

Cumulative Amount of PPA-HCl across human cadaver skin for Diclofenac Sodium Transdermal Systems ($\mu g/cm^2$)

| | Diclo-P10 | Diclo-P11 | Diclo-P12 | Diclo-P13 |
|---|---|---|---|---|
| 5 hours | 0.5 | 659.0 | 1437.8 | 2010.5 |
| 10.5 hours | 4.7 | 1587.6 | 2619.3 | 2992.9 |
| 20 hours | 18.8 | 2273.7 | 3263.0 | 3513.1 |
| 24 hours | 28.4 | 2439.6 | 3420.6 | 3647.3 |

TABLE 52

Excess NaOH Concentration and pH of
Four Diclofenac Sodium Transdermal Systems

|  | Diclo-P10 | Diclo-P11 | Diclo-P12 | Diclo P13 |
|---|---|---|---|---|
| Excess NaOH Concentration (wt %) | 0 | 1.3 | 1.8 | 3.6 |
| pH | 7.17 | 10.59 | 10.72 | 11.28 |

The cumulative amount of diclofenic sodium across human cadaver skin at 24 hours increased from 28.4 µg/cm² to 3647.3 µg/cm² when the calculated excess NaOH concentration in the dried patch was increased from 0% to 3.6%. The cumulative amount of diclofenac sodium across human cadaver skin at 24 hours from the system containing 1.3% NaOH (Diclo-P11) was 2439.6 µg/cm², which was about 85 times higher than that from the formulation without NaOH (28.4 µg/cm², #Diclo-P10).

The pH of the diclofenac sodium patch measured using the procedures listed above increased from 7.17 to 11.28 when the calculated excess NaOH concentration in the dried patch was increased from 0% to 3.6%.

EXAMPLE 17

An in-vitro skin permeation study was conducted using four diclofenac sodium transdermal gels. The formulations used to prepare these gels are listed in Table 53, which include weight and weight percent of each ingredient in the formulations. The weight of sodium hydroxide (NaOH) was 0 g, 0.02 g, 0.03 g, and 0.05 g for formulation #Diclo-DG25, -DG27, -DG28, and -DG29 respectively.

The in-vitro permeation of diclofenac sodium through human cadaver skin from these gels was performed using Franz-type diffusion cells with a diffusion area of 1 cm². Human cadaver skin was cut to desired size and clamped between the donor and receiver chambers of the diffusion cell with the stratum corneum side facing the donor solution. Three diffusion cells were used for each formulation.

Figure 13:
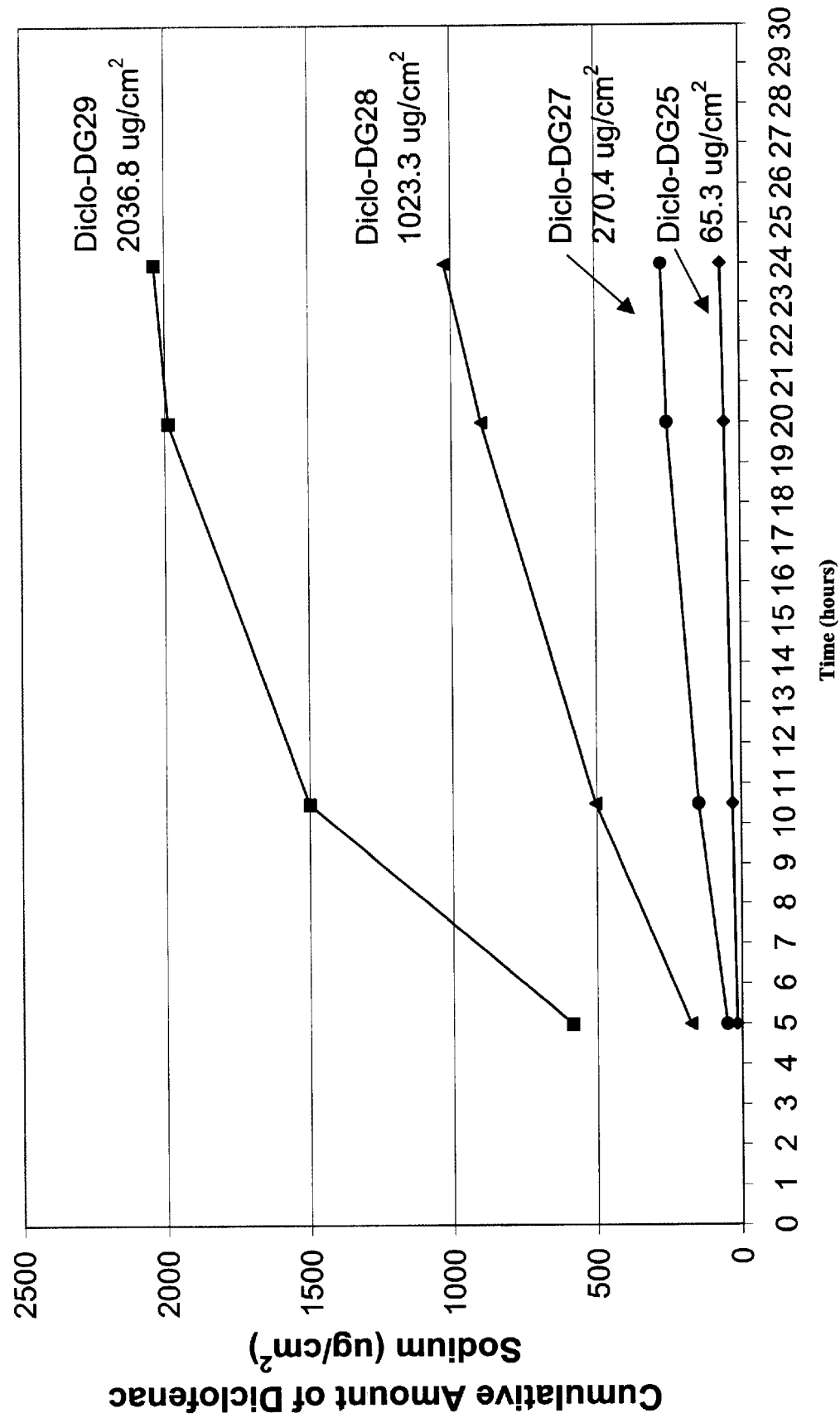
FIG. 13 is a graph illustrating the cumulative amount of diclofenac from a gel as described in Example 17.

10% ethanol/90% water solution was used as the receiver solution. The volume of receiver solution was 8 ml. The receiver solution was collected and replaced with fresh ethanol/water solution at each time point. The receiver solution collected was analyzed by an HPLC for the concentration of diclofenac sodium. The cumulative amount of diclofenac sodium across human cadaver skin was calculated using the measured diclofenac sodium concentrations in the receiver solutions, which were shown in Table 54 and FIG. 13.

Since diclofenac sodium is not expected to react with NaOH, the NaOH concentration listed in Table 53 equals the excess NaOH concentration.

TABLE 53

Weight and Weight Percent of Each Component
(Based on Total Solution Weight)
for Four Diclofenac Sodium Transdermal Gels

|  | Diclo-DG25 | Diclo-DG27 | Diclo-DG28 | Diclo DG29 |
|---|---|---|---|---|
| Diclofenac sodium | 0.3 g (14.1%) | 0.3 g (13.8%) | 0.3 g (13.7%) | 0.3 g (13.50%) |
| Propylene glycol | 0.6 g (28.2%) | 0.6 g (27.6%) | 0.6 g (27.4%) | 0.6 g (26.9%) |
| Ethyl alcohol | 1 g (46.9%) | 1 g (46.1%) | 1 g (45.7%) | 1 g (44.8%) |
| DI water | 0.2 g (9.4%) | 0.22 g (10.1%) | 0.23 g (10.5%) | 0.25 g (11.2%) |
| HPMC | 0.03 g (1.4%) | 0.03 g (1.4%) | 00.3 g (1.4%) | 0.03 g (1.3%) |
| NaOH | 0 | 0.02 g (0.9%) | 0.03 g (1.4%) | 0.05 g (2.2%) |

TABLE 54

Cumulative Amount of PPA-HCl across
human cadaver skin for Diclofenac Sodium
Transdermal Gels (µg/cm²)

|  | Diclo-DG25 | Diclo-DG27 | Diclo-DG28 | Diclo-DG29 |
|---|---|---|---|---|
| 5 hours | 16.8 | 50.6 | 175.9 | 585.2 |
| 10.5 hours | 29.8 | 147.5 | 503.5 | 1499.8 |
| 20 hours | 53.4 | 252.3 | 896.4 | 1988.1 |
| 24 hours | 65.3 | 270.4 | 1023.3 | 2036.8 |

TABLE 55

Excess NaOH Concentration of
Four Diclofenac Sodium Transdermal Gels

|  | Diclo-DG25 | Diclo-DG27 | Diclo-DG28 | Diclo-DG29 |
|---|---|---|---|---|
| Excess NaOH Concentration (wt %) | 0 | 0.9 | 1.4 | 2.2 |

The cumulative amount of diclofenac sodium across human cadaver skin at 24 hours increased from 65.3 µg/cm² to 2036.8 µg/cm² when the calculated excess NaOH concentration in the gel was increased from 0% to 2.2% (Table 55). The cumulative amount of diclofenac sodium across human cadaver skin at 24 hours from the gel containing 0% NaOH (Diclo-DG27) was 270.4 µg/cm², which was about 4 times higher than that from the formulation without NaOH (65.3 µg/cm², #Diclo-DG25).

EXAMPLE 18

An in-vitro skin permeation study was conducted using four testosterone transdermal systems. The formulations used to prepare these systems are listed in Table 56, which include weight and weight percent of each component in the formulations. The weight of sodium hydroxide (NaOH) was 0 g, 0.02 g, 0.04 g, and 0.075 g for formulation #Test-P91, -P92, -P93, and -P94 respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of 11/16 inch. The theoretical percent weight for each ingredient after drying (calculated assuming all the volatile ingredients were completely removed during drying) is listed in Table 57.

The in-vitro permeation of testosterone through human cadaver skin from these discs was performed using Franz-type diffusion cells with a diffusion area of 1 cm$^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with 10% ethanol/90% water solution. The receiver solution was completely withdrawn and replaced with fresh ethanol/water solution at each time point. The samples taken were analyzed by an HPLC for the concentration of testosterone in the receiver solution. The cumulative amount of testosterone across human cadaver skin was calculated using the measured testosterone concentrations in the receiver solutions, which were shown in Table 58 and FIG. 14.

Since testosterone is not expected to react with NaOH, the NaOH concentration listed in Table 57 equals the excess NaOH concentration.

The pH of the patch was determined using the following procedures. A 2.5 cm$^2$ circular patch was punched out. Ten ml of purified water was pipetted into a glass vial, and a stir bar was added, the liner was removed from patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours.

After 18 hours, the stir bar was removed from vial and the pH of the solution determined using a calibrated pH meter. The measured pHs for the testosterone transdermal systems are listed in Table 59.

TABLE 56

Weight and Weight Percent of Each Component (Based on Total Solution Weight) for Four Testosterone Transdermal Systems

|  | Test-P91 | Test-P92 | Test-P93 | Test-P94 |
|---|---|---|---|---|
| Testosterone | 0.3 g (4.8%) | 0.3 g (4.7%) | 0.3 g (4.7%) | 0.3 g (4.7%) |
| Ethyl alcohol | 0.5 g (7.9%) | 0.5 g (7.9%) | 0.5 g (7.8%) | 0.5 g (7.8%) |
| Propylene glycol | 0.5 g (7.9%) | 0.5 g (7.9%) | 0.5 g (7.8%) | 0.5 g (7.8%) |
| NaOH | 0 | 0.02 g (0.3%) | 0.04 g (0.6%) | 0.075 g (1.2%) |
| DI water | 0 | 0.02 g (0.3%) | 0.04 g (0.6%) | 0.075 g (1.2%) |
| PIB adhesive (30% solid) | 4 g (63.5%) | 4 g (63.1%) | 4 g (62.7%) | 4 g (62.0%) |
| Heptane | 1 g (15.9%) | 1 g (15.8%) | 1 g (15.7%) | 1 g (15.5%) |

TABLE 57

Weight and Theoretical Weight Percent of Each Ingredient in the Dried Film for Four Testosterone Transdermal Systems

|  | Test-P91 | Test-P92 | Test-P93 | Test-P94 |
|---|---|---|---|---|
| Testosterone | 0.3 g (15.0%) | 0.3 g (14.9%) | 0.3 g (14.7%) | 0.3 g (14.5%) |
| Propylene glycol | 0.5 g (25.0%) | 0.5 g (24.8%) | 0.5 g (24.5%) | 0.5 g (24.1%) |
| NaOH | 0 | 0.02 g (1.0%) | 0.04 g (2.0%) | 0.075 g (3.6%) |
| PIB adhesive | 1.2 g (60.0%) | 1.2 g (59.4%) | 1.2 g (58.8%) | 1.2 g (57.8%) |

TABLE 58

Cumulative Amount of Testosterone across human cadaver skin for Testosterone Transdermal Systems ($\mu g/cm^2$)

|  | Test-P91 | Test-P92 | Test-P93 | Test-P94 |
|---|---|---|---|---|
| 5 hours | 1.9 | 7.3 | 36.1 | 76.1 |
| 16.25 hours | 4.3 | 28.5 | 78.0 | 147.8 |
| 20 hours | 5.3 | 36.6 | 89.5 | 168.8 |
| 25 hours | 7.4 | 49.9 | 108.0 | 199.4 |

TABLE 59

Excess NaOH Concentration and pH of Four Testosterone Transdermal Systems

|  | Test-P91 | Test-P92 | Test-P93 | Test-P94 |
|---|---|---|---|---|
| Excess NaOH Concentration (wt %) | 0 | 1.0 | 2.0 | 3.6 |
| pH | 7.14 | 9.17 | 10.04 | 10.32 |

The cumulative amount of testosterone across human cadaver skin at 24 hours increased from 7.4 $\mu g/cm^2$ to 199.4 $\mu g/cm^2$ when the calculated excess NaOH concentration in the dried patch was increased from 0% to 3.6%. The cumulative amount of testosterone across human cadaver skin at 24 hours from the system containing 1.0% NaOH (Test-P92) was 49.9 mg/cm$^2$, which was about six times higher than that from the formulation without NaOH (7.4 $\mu g/cm^2$, #Test-P91). This result indicated that the permeation of testosterone could be enhanced with an excess NaOH concentration as low as 1.0%.

The pH of the testosterone patch measured using the procedures listed above increased from 7.14 to 10.32 when the calculated excess NaOH concentration in the dried patch was increased from 0% to 3.6%.

EXAMPLE 19

An in-vitro skin permeation study was conducted using three oxybutynin HCl transdermal systems. The formulations used to prepare these systems are listed in Table 60, which include weight and weight percent of each ingredient in the formulations. The weight of sodium hydroxide (NaOH) was 0.15 g, 0.25 g, and 0.35 g for formulation #Oxy-P1, -P2, and -P3 respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of $^{11}/_{16}$ inch. The theoretical percent weight for each ingredient after drying (calculated assuming all the volatile ingredients were completely removed during drying) is listed in Table 61.

The in-vitro permeation of oxybutynin HCl through human cadaver skin from these discs was performed using Franz-type diffusion cells with a diffusion area of 1 cm$^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Three diffusion cells were used for each formulation.

The cells were filled with 10% ethanol/90% water solution. The receiver solution was completely withdrawn and replaced with fresh ethanol/water solution at each time point. The samples taken were analyzed by an HPLC for the concentration of oxybutynin HCl in the receiver solution. The cumulative amount of oxybutynin HCl across human cadaver skin was calculated using the measured oxybutynin HCl concentrations in the receiver solutions, which were shown in Table 62.

TABLE 60

Weight and Weight Percent of Each Component (Based on Total Solution Weight) for Three Oxybutynin HCl Transdermal Systems

|  | Oxy-P1 | Oxy-P2 | Oxy-P3 |
| --- | --- | --- | --- |
| Oxybutynin HCl | 0.5 g (6.5%) | 0.5 g (6.3%) | 0.5 g (6.2%) |
| DI water | 0.65 g (8.4%) | 0.75 g (9.5%) | 0.85 g (10.5%) |
| NaOH | 0.15 g (1.9%) | 0.25 g (3.2%) | 0.35 g (4.3%) |
| Propylene glycol | 0.3 g (3.9%) | 0.3 g (3.8%) | 0.3 g (3.7%) |
| Triton X100 | 0.1 g (1.3%) | 0.1 g (1.3%) | 0.1 g (1.2%) |
| PIB adhesive (30% solid) | 4 g (51.9%) | 4 g (50.6%) | 4 g (49.4%) |
| Methylal | 1 g (13.0%) | 1 g (12.7%) | 1 g (12.3%) |
| Heptane | 1 g (13.0%) | 1 g (12.7%) | 1 g (12.3%) |

TABLE 61

Weight and Theoretical Weight Percent of Each Ingredient in the Dried Film for Three Oxybutynin HCl Transdermal Systems

|  | Oxy-P1 | Oxy-P2 | Oxy-P3 |
| --- | --- | --- | --- |
| Oxybutynin HCl | 0.5 g (15.4%) | 0.5 g (14.9%) | 0.5 g (14.5%) |
| NaOH | 0.15 g (4.6%) | 0.25 g (7.5%) | 0.35 g (10.1%) |
| Propylene glycol | 0.3 g (9.2%) | 0.3 g (9.0%) | 0.3 g (8.7%) |
| Triton X100 | 0.1 g (3.1%) | 0.1 g (3.0%) | 0.1 g (2.9%) |
| PIB adhesive | 1.2 g (36.9%) | 1.2 g (35.8%) | 1.2 g (34.8%) |
| Methylal | 1 g (30.8%) | 1 g (29.9%) | 1 g (29.0%) |

TABLE 62

Cumulative Amount of Oxybutynin HCl across human cadaver skin for Oxybutynin HCl Transdermal Systems ($\mu g/cm^2$)

|  | Oxy-P1 | Oxy-P2 | Oxy-P3 |
| --- | --- | --- | --- |
| 5 hours | 691.0 | 2108.7 | 1399.5 |
| 10.5 hours | 1259.4 | 2615.9 | 1865.9 |
| 24 hours | 1747.7 | 2853.5 | 2322.8 |

The cumulative amount of diclofenac sodium across human cadaver skin at 24 hours ranged from 1747.7 $\mu g/cm^2$ to 2322.8 $\mu g/cm^2$ when the NaOH concentration in the dried patch was increased from 4.6% to 10.1%.

EXAMPLE 20

An in-vitro skin permeation study was conducted using four diclofenac sodium transdermal systems. The formulations used to prepare these systems are listed in Table 63, which include weight and weight percent of each ingredient in the formulations. The weight of sodium hydroxide (NaOH) was 0 g, 0.01 g, 0.02 g, and 0.05 g for formulation #Diclo-P64, -P86, -P65, and -P87 respectively. Each formulation was coated on a release liner and dried in an oven at 55° C. for two hours to remove water and other solvents. The dried drug-in-adhesive/release liner film was laminated to a backing film. The backing/drug-in-adhesive/release liner laminate was then cut into round discs with a diameter of 11/16 inch. The theoretical percent weight for each ingredient after drying (calculated assuming all the volatile ingredients were completely removed during drying) is listed in Table 64.

The in-vitro permeation of diclofenac sodium through human cadaver skin from these discs was performed using Franz-type diffusion cells with a diffusion area of 1 cm$^2$. The volume of receiver solution was 8 ml. Human cadaver skin was cut to desired size and placed on a flat surface with the stratum corneum side facing up. The release liner was peeled away from the disc laminate. The backing/drug-in-adhesive film was placed and pressed on the skin with the adhesive side facing the stratum corneum. The skin/adhesive/backing laminate was clamped between the donor and receiver chambers of the diffusion cell with the skin side facing the receiver solution. Twelve diffusion cells were used for each formulation.

The cells were filled with 10% ethanol/90% water solution. At each time point, the pH at the interface between skin and the patch for three diffusion cells was measured by removing the receiving fluid, removing the clamp and the donor chamber, gently teasing the patch away from the skin with tweezers, leaving the skin on the receiver chamber, measuring the pH of the solution on the skin by placing the microelectrode directly onto the skin surface. The measured pHs at the skin/patch interface were listed in Table 65. For all other cells, the receiving fluid was completely withdrawn and replaced with fresh ethanol/water solution. The samples taken were analyzed by an HPLC for the concentration of diclofenac sodium in the receiver solution. The pHs of the receiver solutions taken were measured by a pH meter. The cumulative amount of diclofenac sodium across human cadaver skin was calculated using the measured diclofenac sodium concentrations in the receiver solutions, which were shown in Table 66. The pHs of the receiver solutions were listed in Table 67.

Since diclofenac sodium is not expected to react with NaOH, the NaOH concentration listed in Table 64 equals the excess NaOH concentration.

The pH of the patch was determined using the following procedures. A 2.5 cm$^2$ circular patch was punched out. Ten ml of purified water was pipetted into a glass vial, and a stir bar was added, the liner was removed from the patch and placed in the vial along with the patch. The vial was then placed on a stir plate and the water/patch/liner mixture was stirred for 5 minutes, at which point the liner was removed from the vial and discarded. The vial was again placed on a stir plate and stirring continued for an additional 18 hours. After 18 hours, the stir bar was removed from the vial and the pH of the solution determined using a calibrated pH meter. The measured pHs for the diclofenac sodium transdermal systems are listed in Table 68.

TABLE 63

Weight and Weight Percent of Each Ingredient (Based on Total Solution Weight) for Four Diclofenac Sodium Transdermal Systems

|  | Diclo-P64 | Diclo-P86 | Diclo-P65 | Diclo-P87 |
| --- | --- | --- | --- | --- |
| Diclofenac sodium | 0.6 g (9.2%) | 0.6 g (9.2%) | 0.9 g (9.2%) | 0.6 g (9.1%) |
| Propylene glycol | 0.9 g (13.8%) | 0.9 g (13.8%) | 0.9 g (13.8%) | 0.9 g (13.6%) |
| NaOH | 0 | 0.01 g (0.2%) | 0.02 g (0.3%) | 0.05 g (0.8%) |
| PIB adhesive (30% solid) | 4 g (61.5%) | 4 g (61.3%) | 4 g (61.2%) | 4 g (60.6%) |
| Heptane | 1 g (15.4%) | 1 g (15.3%) | 1 g (15.3%) | 1 g (15.2%) |
| DI water | 0 | 0.01 g (0.2%) | 0.02 g (0.3%) | 0.05 g (0.8%) |

TABLE 64

Weight and Theoretical Weight Percent of Each Ingredient in the Dried Film for Four Diclofenac Sodium Transdermal Systems

|  | Diclo-P64 | Diclo-P86 | Diclo-P65 | Diclo-P87 |
| --- | --- | --- | --- | --- |
| Diclofenac sodium | 0.6 g (22.2%) | 0.6 g (22.1%) | 0.9 g (22.1%) | 0.6 g (21.8%) |
| Propylene glycol | 0.9 g (33.3%) | 0.9 g (33.2%) | 0.9 g (33.1%) | 0.9 g (32.7%) |
| NaOH | 0 | 0.01 g (0.4%) | 0.02 g (0.7%) | 0.05 g (1.8%) |
| PIB adhesive | 1.2 g (44.4%) | 1.2 g (44.3%) | 1.2 g (44.1%) | 1.2 g (43.6%) |

TABLE 65 pHs at the Interface between Skin and Patch at Various Time Points for Diclofenac Sodium Transdermal Systems

|  | Diclo-P64 | Diclo-P86 | Diclo-P65 | Diclo-P87 |
| --- | --- | --- | --- | --- |
| 3 hours | * | 11.0 | * | 10.3 |
| 6 hours | * | 11.0 | 11.2 | 9.8 |
| 10 hours | 8.5 | 10.9 | 10.7 | 10.2 |
| 24 hours | * | 9.7 | 10.1 | 9.4 |

*Cannot be measured because there was not enough solution at the interface

TABLE 66

Cumulative Amount of Diclofenac Sodium across human cadaver skin for Diclofenac Sodium Transdermal Systems ($\mu g/cm^2$)

|  | Diclo-P64 | Diclo-P86 | Diclo-P65 | Diclo-P87 |
| --- | --- | --- | --- | --- |
| 3 hours | 7.5 | 1.5 | 33.4 | 257.7 |
| 6 hours | 39.6 | 18.3 | 269.3 | 793.3 |
| 10 hours | 63.2 | 49.3 | 654.4 | 1652.2 |
| 24 hours | 34.6 | 227.7 | 1733.8 | 3257.7 |

TABLE 67 pHs of Receiver Solutions at Various Time Points for Diclofenac Sodium Transdermal Systems

|  | Diclo-P64 | Diclo-P86 | Diclo-P65 | Diclo-P87 |
| --- | --- | --- | --- | --- |
| 3 hours | 8.1 | 8.0 | 9.3 | 10.8 |
| 6 hours | 7.4 | 7.9 | 7.7 | 10.0 |
| 10 hours | 7.0 | 7.6 | 7.3 | 7.7 |
| 24 hours | 7.0 | 8.9 | 7.5 | 9.6 |

TABLE 68

Excess NaOH Concentration and pH of Four Diclofenac Sodium Transdermal Systems

|  | Diclo-P64 | Diclo-P86 | Diclo-P65 | Diclo-P87 |
| --- | --- | --- | --- | --- |
| Excess NaOH Concentration (wt %) | 0 | 0.4 | 0.7 | 1.8 |
| PH | 7.40 | 8.99 | 10.71 | 10.38 |

The cumulative amount of diclofenac sodium across human cadaver skin at 24 hours increased from 34.6 $\mu g/cm^2$ to 3257.7 $\mu g/cm^2$ (Table 69) when the calculated excess NaOH concentration in the dried patch was increased from 0% to 1.8% (Table 64). The cumulative amount of diclofenac sodium across human cadaver skin at 24 hours from the system containing 0.4% NaOH (Diclo-P86) was 227.7 $\mu g/cm^2$, which was about six times higher than that from the formulation without NaOH (34.6 $\mu g/cm^2$, #Diclo-P64). This result indicated that the permeation of diclofenac sodium across human skin could be enhanced by a NaOH concentration as low as 0.4%.

The pHs at the interface between skin and the patch were about the same as shown in Table 67, even though the concentration of NaOH was increased from 0.4% to 1.8%. It was noticed that the less the amount of solution at the interface, the higher the NaOH concentration. It was difficult to measure the pH of interface between skin and patch for the formulations without NaOH or with a low NaOH concentration because there was not enough solution on the top of the skin.

Since the pH measurement for the interface between the skin and patch may be difficult for low NaOH concentrations, the pHs of the receiver solutions were measured at various time points. The pHs of receiver solutions listed in Table 67 indicated that the pHs depend on the time interval between sampling, the NaOH concentration in the patch and the time point. The pHs at the 3-hour time point increased from 8.0 to 10.8 when the NaOH concentration in the patch was increased from 0.4% to 1.8%.

The pH of the diclofenac sodium patch measured using the procedures listed above increased from 7.40 to 10.38 when the calculated excess NaOH concentration in the dried patch was increased from 0% to 1.8% (Table 68).

What is claimed is:

1. A method for enhancing the flux of a drug through a body surface, comprising administering the drug to a localized region of a human patient's body surface in combination with a hydroxide-releasing agent, the hydroxide-releasing agent being present in an amount effective to enhance the flux of the drug through the localized region of the body surface without causing damage thereto, and effective to provide a pH in the range of approximately 8.5 to 13.0 at the localized region of the body surface, during drug administration, wherein the drug and hydroxide-releasing agent are present in a formulation and the amount of hydroxide-releasing agent in the formulation applied to the body surface is the total of (a) the amount required to neutralize any acidic species in the formulation plus (b) an amount equal to approximately 0.5 wt. % to 25.0 wt. % of the formulation.

2. The method of claim 1, wherein the body surface is skin.

3. The method of claim 1, wherein the body surface is mucosal tissue.

4. The method of claim 1, wherein the formulation is aqueous.

5. The method of claim 4, wherein the formulation pH is in the range of approximately 8.5 to 11.5.

6. The method of claim 4, wherein the aqueous formulation is selected from the group consisting of a cream, a gel, a lotion, and a paste.

7. The method of claim 6, wherein the formulation is a cream.

8. The method of claim 6, wherein the formulation is a gel.

9. The method of claim 1, wherein the formulation is nonaqueous.

10. The method of claim 9, wherein the formulation is an ointment.

11. The method of claim 1, wherein the hydroxide-releasing agent releases free hydroxide ions in the presence of an aqueous fluid.

12. The method of claim 1, wherein the hydroxide-releasing agent is selected from the group consisting of inorganic hydroxides, inorganic oxides, metal salts of weak acids, and mixtures thereof.

13. The method of claim 12, wherein the hydroxide-releasing agent is an inorganic hydroxide.

14. The method of claim 13, wherein the inorganic hydroxide is selected from the group consisting of ammonium hydroxide, alkali metal hydroxides, alkaline earth metal hydroxides, and mixtures thereof.

15. The method of claim 14, wherein the inorganic hydroxide is selected from the group consisting of ammonium hydroxide, sodium hydroxide, calcium hydroxide, potassium hydroxide, magnesium hydroxide, and mixtures thereof.

16. The method of claim 15, wherein the inorganic hydroxide is sodium hydroxide.

17. The method of claim 15, wherein the inorganic hydroxide is potassium hydroxide.

18. The method of claim 12, wherein the hydroxide-releasing agent is an inorganic oxide.

19. The method of claim 18, wherein the inorganic oxide is selected from the group consisting of magnesium oxide, calcium oxide, and mixtures thereof.

20. The method of claim 17, wherein the hydroxide-releasing agent is a metal salt of a weak acid.

21. The method of claim 20, wherein the hydroxide-releasing agent is selected from the group consisting of sodium acetate, sodium carbonate, tribasic sodium phosphate, dibasic sodium phosphate, sodium borate, potassium carbonate, potassium acetate, dibasic potassium phosphate, tribasic potassium phosphate, sodium metaborate, and mixtures thereof.

22. The method of claim 13, wherein the amount of inorganic hydroxide in the formulation is the total of (a) the amount required to neutralize any acidic species in the formulation plus (b) an amount equal to approximately 0.5 wt. % to 4.0 wt. % of the formulation.

23. The method of claim 22, wherein the amount of inorganic hydroxide in the formulation is the total of (a) the amount required to neutralize any acidic species in the formulation plus (b) an amount equal to approximately 0.5 wt. % to 3.0 wt. % of the formulation.

24. The method of claim 23, wherein the amount of inorganic hydroxide in the formulation is the total of (a) the amount required to neutralize any acidic species in the formulation plus (b) an amount equal to approximately 0.75 wt. % to 2.0 wt. % of the formulation.

25. The method of claim 24, wherein the amount of inorganic hydroxide in the formulation is the total of (a) the amount required to neutralize any acidic species in the formulation plus (b) an amount equal to approximately 1.0 wt. % of the formulation.

26. The method of claim 22, wherein the drug is an acid addition salt of a basic compound, and the amount in (a) is the amount required to neutralize the acid addition salt and any other acidic species in the formulation.

27. The method of claim 22, wherein the drug is an acidic drug in the form of a free acid, and the amount in (a) is the amount required to neutralize the acidic drug and any other acidic species in the formulation.

28. The method of claim 22, wherein the drug is a basic drug in the form of a free base.

29. The method of claim 22, wherein the drug is a basic addition salt of an acidic compound.

30. The method of claim 22, wherein the drug is nonionizable.

31. The method of claim 18, wherein the formulation contains up to approximately 25 wt. % of the hydroxide-releasing agent.

32. The method of claim 31, wherein the formulation contains up to approximately 20 wt. % of the hydroxide-releasing agent.

33. The method of claim 20, wherein the formulation contains up to approximately 25 wt. % of the hydroxide-releasing agent.

34. The method of claim 33, wherein the formulation contains up to approximately 20 wt. % of the hydroxide-releasing agent.

35. The method of claim 1, wherein the drug and hydroxide-releasing agent are administered by applying a drug delivery device to the localized region of the patient's body surface thereby forming a body surface-delivery device interface, the device comprising the drug and the hydroxide-releasing agent, and having an outer backing layer that serves as the outer surface of the device during use.

36. The method of claim 35, wherein the drug and hydroxide-releasing agent are present in an adhesive, gel or liquid formulation contained within the device.

37. The method of claim 35, wherein the outer backing layer is occlusive.

38. The method of claim 1, wherein the drug is administered in combination with an additional permeation enhancer.

39. The method of claim 1, wherein the drug is locally acting and administration is topical.

40. The method of claim 1, wherein the drug is systemically acting and administration is transdermal.

41. The method of claim 1, wherein the drug and the hydroxide-releasing agent are administered without any additional permeation enhancer.

* * * * *

UNITED STATES PATENT AND TRADEMARK OFFICE
CERTIFICATE OF CORRECTION

| | | |
|---|---|---|
| PATENT NO. | : 6,586,000 B2 | Page 1 of 1 |
| DATED | : July 1, 2003 | |
| INVENTOR(S) | : Eric C. Luo et al. | |

It is certified that error appears in the above-identified patent and that said Letters Patent is hereby corrected as shown below:

<u>Column 61,</u>
Line 56, please delete "17" and insert -- 12 --

Signed and Sealed this

Sixteenth Day of December, 2003

JAMES E. ROGAN
*Director of the United States Patent and Trademark Office*